(12) United States Patent
Klar et al.

(10) Patent No.: US 7,001,916 B1
(45) Date of Patent: *Feb. 21, 2006

(54) EPOTHILON DERIVATIVES, METHOD FOR THE PRODUCTION AND THE USE THEREOF AS PHARMACEUTICALS

(75) Inventors: Ulrich Klar, Belin (DE); Werner Skuballa, Berlin (DE); Bernd Buchmann, Hohen Neuendorf (DE); Wolfgang Schwede, Berlin (DE); Michael Schirner, Berlin (DE)

(73) Assignee: Schering, AG, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/913,163

(22) PCT Filed: Feb. 11, 2000

(86) PCT No.: PCT/EP00/01104

§ 371 (c)(1),
(2), (4) Date: Dec. 7, 2001

(87) PCT Pub. No.: WO00/47584

PCT Pub. Date: Aug. 17, 2000

Related U.S. Application Data

(63) Continuation-in-part of application No. PCT/EP00/01104, filed on Feb. 11, 2000.

(30) Foreign Application Priority Data

Feb. 11, 1999 (DE) .................. 199 07 480
Nov. 4, 1999 (DE) .................. 199 54 229

(51) Int. Cl.
*A61K 31/335* (2006.01)
*C07D 277/30* (2006.01)

(52) U.S. Cl. .................. 514/365; 548/204; 548/217
(58) Field of Classification Search .................. 548/204, 548/217; 514/365
See application file for complete search history.

(56) References Cited

U.S. PATENT DOCUMENTS

| 5,469,145 A | 11/1995 | Johnson |
| 6,043,372 A | 3/2000 | Schinzer et al. |
| 6,156,905 A | 12/2000 | Schinzer et al. |
| 6,730,699 B1 | 5/2004 | Li et al. |
| 2002/0058817 A1* | 5/2002 | Danishefsky et al. |
| 2004/0012735 A1 | 1/2004 | Sato et al. |
| 2004/0019088 A1* | 1/2004 | Hoffman et al. |

FOREIGN PATENT DOCUMENTS

| DE | 4138042 | 5/1993 |
| DE | 19636343 | 10/1997 |
| DE | 19701758 | 7/1998 |
| WO | WO 9719086 | 5/1997 |
| WO | WO 98/08849 | 3/1998 |
| WO | WO 98/25929 | 6/1998 |
| WO | WO 99/01124 | 1/1999 |
| WO | WO 99/02514 | 1/1999 |
| WO | WO 99/07692 | 2/1999 |
| WO | WO 99/67253 | 12/1999 |
| WO | 2001066154 | * 9/2001 |
| WO | WO 01/66154 | 9/2001 |
| WO | 2004012735 | * 2/2004 |
| WO | WO 2004015088 | 2/2004 |

OTHER PUBLICATIONS

Ca 127:268036, "Water soluble paclitaxel prodrugs", Li et al., U.S. Patent 6730699.
Ca 140:176348, "Transposon-based transformation system encoding a transposase and uses for mutagenesis", Julien et al., WO 2004015088.
W. Clarke Still et al.: Tetradedron Letters, Bd. 21, 1980, Seiten 103-4, XP002095727.
K. A. Parker et al.: Journal of Organic Chemistry, Bd. 52, Nr. 19, 1987, Seiten 4369-77, XP002095726.
K. Tamao et al.: Journal of the Chemical Society, Chemical Communications, 1988, Seiten 795-7, XP002095725.
D. Schinzer et al.: Chemistry—A European Journal, Bd. 2, Nr. 11, 1996, Seiten 1477-82, XP002095724 in der Anmeldung erwaehnt.
K. C. Nicolaou et al.: Angewandte Chemie, Bd. 109, Nr. 19, 1997, Seiten 2181-7, XP002095723 in der Anmeldung erwaehnt.
K. C. Nicolaou et al.: Journal of the American Chemical Society, Bd. 119, Nr. 34, 1997, Seiten 7974-91, XP002095719 in der Anmeldung erwaehnt.

(Continued)

Primary Examiner—Celia Chang
(74) Attorney, Agent, or Firm—Millen, White, Zelano & Branigan, P.C.

(57) ABSTRACT

Disclosed are epothilone compounds of formula I,

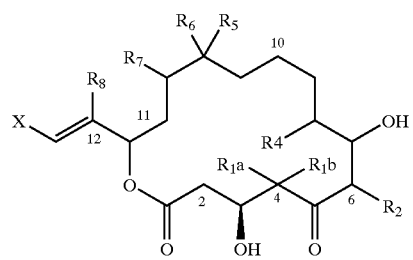

which are useful as pharmaceutical compounds for treating, for example, malignant tumors and chronic inflammatory diseases and are useful in anti-angiogenesis therapy.

20 Claims, No Drawings

OTHER PUBLICATIONS

Ca Reference 132:293587, "The Olefin Metathesis Approach to Epothilone A and its Analogs", Nicolau et al., p. 674, No. 22, Year 2000.

Nicolau et al., "Total Synthesis of Oxazole-and Cyclopropane-Cotaining Epothilone B Analogues by the Macrolactonization Approach", pp. 1971-1986, Chem. Eur. J., vol. 3, No. 12, 1997.

U.S. Appl. No. 09/485,292.

U.S. Appl. No. 09/979,939.

Zhen Yang et al.: Angewandte Chemie, Bd. 109, Nr. 1/2, 1997, Seiten 170-2, XP002095722 in der Anmeldung erwaehnt.

K. C. Nicolaou et al.: Nature, Bd. 387, Nr. 6630, 15. Mai 1997, Seiten 268-72, XP002095721 in der Anmeldung erwaehnt.

D. Schinzer et al.: Angewandte Chemie, Bd. 109, Nr. 5, 1997, Seiten 543-4, XP002095720 in der Anmeldung erwaehnt.

K. C. Nicolaou: Journal of the American Chemical Society, Bd. 119, Nr. 34, 1997, Seiten 7960-73, XP002064442 in der Anmeldung erwaehnt.

K.C. Nicolaou et al.: "Designed Epothilones: Combinatorial Synthesis, Tubulin Assembly Properties, And Cytotoxic Action Against Taxol.Resistant Tumor Cells" Angewandte Chemie. International Edition, DE. Verlag Chemie. Weinheim, vol. 36, No. 19, 1997, pp. 2097-2103, XP00206441.

K.C. Nicolaou et al.: "Chemical Biology of Epothilone" Angewandte Chemie, International Edition, De. Verlag Chemie. Weinheim, vol. 37, No. 15, Aug. 1998 pp. 2014-2045, XP002131418.

K.C. Nicolaou et al.: "Total Synthesis of Oxazole- and Cyclopropane-Containing Epothilone A Analogues by the Olefin Metathesis Approach"—Chem Eur. J. 1997, 3, No. 12, pp. 1957-1970.

* cited by examiner

EPOTHILON DERIVATIVES, METHOD FOR THE PRODUCTION AND THE USE THEREOF AS PHARMACEUTICALS

Höfle et al. describe the cytotoxic action of the natural substances epothilone A (R=hydrogen) and epothilone B (R=methyl)

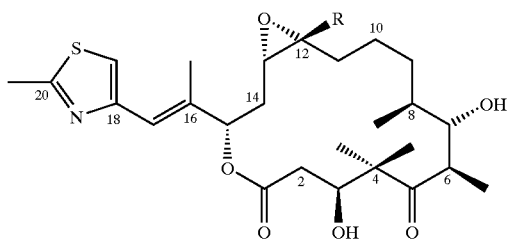

Epothilone A (R=H), Epothilone B (R=CH$_3$ in, e.g., Angew. Chem. [Applied Chem.], 1996, 108, 1671–1673. Because of their in-vitro selectivity for breast cell lines and intestinal cell lines and their significantly higher activity against P-glycoprotein-forming multiresistant tumor lines in comparison to taxol as well as their physical properties that are superior to those of taxol, e.g., a water solubility that is higher by a factor of 30, this novel structural class is especially advantageous for the development of a pharmaceutical agent for treating malignant tumors.

The natural substances are not sufficiently stable either chemically or metabolically for the development of pharmaceutical agents. To eliminate these drawbacks, modifications to the natural substance are necessary. Such modifications are possible only with a total-synthesis approach and require synthesis strategies that make possible a broad modification of the natural substance. The purpose of the structural changes is also to increase the therapeutic range. This can be done by improving the selectivity of the action and/or increasing the active strength and/or reducing undesirable toxic side-effects, as they are described in Proc. Natl. Acad. Sci. USA 1998, 95, 9642–9647.

The total synthesis of epothilone A is described by Schinzer et al. in Chem. Eur. J. 1996, 2, No. 11, 1477–1482 and in Angew. Chem. 1997, 109, No. 5, pp. 543–544). Epothilone derivatives were already described by Höfle et al. in WO 97/19086. These derivatives were produced starting from natural epothilone A or B.

Another synthesis of epothilone and epothilone derivatives was described by Nicolaou et al. in Angew. Chem. 1997, 109, No. 1/2, pp. 170–172. The synthesis of epothilone A and B and several epothilone analogs was described in Nature, Vol. 387, 1997, pp. 268–272; and the synthesis of epothilone A and its derivatives was described in J. Am. Chem. Soc., Vol. 119, No. 34, 1997, pp. 7960–7973 as well as the synthesis of epothilone A and B and several epothilone analogs in J. Am. Chem. Soc., Vol. 119, No. 34, 1997, pp. 7974–7991 also by Nicolaou et al.

Nicolaou et al. also describe in Angew. Chem. 1997, 109, No. 19, pp. 2181–2187 the production of epothilone A analogs using combinatory solid-phase synthesis. Several epothilone B analogs are also described there.

The object of this invention consists in making available new epothilone derivatives, which are both chemically and metabolically stable enough for the development of pharmaceutical agents and which are superior to natural derivatives in terms of their therapeutic range, their selectivity of action and/or undesirable toxic side-effects and/or their active strength.

This invention describes the new epothilone derivatives of general formula I,

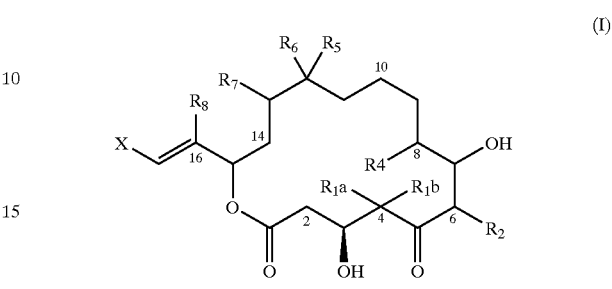

in which
$R^4$ means hydrogen, $C_1$–$C_{10}$ alkyl, aryl, $C_7$–$C_{20}$ aralkyl,
$R^5$ means hydrogen, $C_1$–$C_{10}$ alkyl, aryl, $C_7$–$C_{20}$ aralkyl,
$R^6$, $R^7$ each mean a hydrogen atom, together an additional bond or an oxygen atom,
$R^8$ means a methyl group or hydrogen,
and at the same time, $R^{1a}$ and $R^{1b}$ together stand for a trimethylene group, $R^2$ stands for a phenyl or benzyl radical, and X stands for a 2-pyridyl, 2-methyl-4-thiazolyl or 2-methyl-4-oxazolyl radical or
at the same time $R^{1a}$ and $R^{1b}$ together stand for a trimethylene group, $R^2$ stands for a methyl, ethyl or propyl group and X stands for a 2-pyridyl, 2-methyl-4-thiazolyl or 2-methyl-4-oxazolyl radical or
at the same time $R^{1a}$ and $R^{1b}$ in each case stand for a methyl group, $R^2$ stands for a methyl, ethyl or propyl radical, and X stands for a 2-pyridyl, 2-methyl-4-thiazolyl or 2-methyl-4-oxazolyl radical,
whereby the nitrogen atom and/or the sulfur atom in X can be present in oxidized form, and whereby, if $R^2$ and $R^8$ in each case mean a methyl radical, X can be only one 2-pyridyl radical that is optionally oxidized on the nitrogen atom, including all possible stereoisomers as well as their mixtures.

Substituents in the compounds of general formula I:
As alkyl groups $R^4$ and $R^5$, straight-chain or branched-chain alkyl groups with 1–20 carbon atoms can be considered, such as, for example, methyl, ethyl, propyl, isopropyl, butyl, isobutyl, tert-butyl, pentyl, isopentyl, neopentyl, heptyl, hexyl, and decyl.

Alkyl groups $R^4$ and $R^5$ can be perfluorinated or substituted by 1–5 halogen atoms, hydroxy groups, $C_1$–$C_4$ alkoxy groups, $C_6$–$C_{12}$ aryl groups (which can be substituted by 1–3 halogen atoms).

As aryl radicals $R^4$ and $R^5$, substituted and unsubstituted carbocyclic or heterocyclic radicals with one or more heteroatoms, such as, e.g., phenyl, naphthyl, furyl, thienyl, pyridyl, pyrazolyl, pyrimidinyl, oxazolyl, pyridazinyl, pyrazinyl, quinolyl, thiazolyl, which can be substituted in one or more places by halogen, OH, O-alkyl, $CO_2H$, $CO_2$-alkyl, —$NH_2$, —$NO_2$, —$N_3$, —CN, $C_1$–$C_{20}$alkyl, $C_1$–$C_{20}$ acyl, $C_1$–$C_{20}$ acyloxy-groups, are suitable. Heteroatoms in the heteroaryl radicals can be oxidized; thus, for example, the thiazole ring can be present in the form of N-oxide.

The nitrogen atom in the 2-pyridyl radical, 2-methyl-4-thiazolyl radical or 2-methyl-4-oxazolyl radical standing for X can also be present in the form of the N-oxide.

The aralkyl groups in $R^4$ and $R^5$ can contain in the ring up to 14 C atoms, preferably 6 to 10, and in the alkyl chain 1 to 8, preferably 1 to 4 atoms. As aralkyl radicals, for example, benzyl, phenylethyl, naphthylmethyl, naphthylethyl, furylmethyl, thienylethyl, and pyridylpropyl are suitable. The rings can be substituted in one or more places by halogen, OH, O-alkyl, $CO_2H$, $CO_2$-alkyl, $-NO_2$, $-N_3$, $-CN$, $C_1-C_{20}$ alkyl, $C_1-C_{20}$ acyl, $C_1-C_{20}$ acyloxy groups.

The representation of the new epothilone derivatives is based on the linkage of three partial fragments A, B and C (DE 197 51 200.3, date of application Nov. 13, 1997 as well as the corresponding PCT/EP98/05064). The interfaces are as indicated in general formula I' (Y and Z=oxygen).

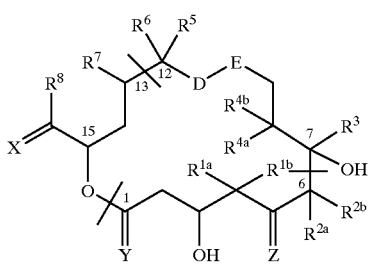

A means a C1–C6 fragment (epothilone numbering system) of general formula

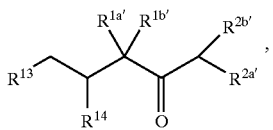

in which $R^{1a'}$, $R^{1b'}$ are the same or different and mean hydrogen, $C_1-C_{10}$ alkyl, aryl, $C_7-C_{20}$ aralkyl, or together a $-(CH_2)_m$ group with m=2, 3, 4 or 5, $R^{2a'}$, $R^{2b'}$ are the same or different and mean hydrogen, $C_1-C_{20}$ alkyl, aryl, $C_7-C_{20}$ aralkyl or together a $-(CH_2)_n$ group with n=2, 3, 4 or 5, $R^{13}$ means $CH_2OR^{13a}$, $CH_2-Hal$, CHO, $CO_2R^{13b}$, COHal, $R^{14}$ means hydrogen, $OR^{14a}$, Hal, $OSO_2R^{14b}$, $R^{13a}$, $R^{14a}$ mean hydrogen, $SO_2$-alkyl, $SO_2$-aryl, $SO_2$-aralkyl or together a $-(CH_2)_o$ group or together a $CR^{15a}R^{15b}$ group, $R^{13b}$, $R^{14b}$ mean hydrogen, $C_1-C_{20}$ alkyl, aryl, $C_7-C_{20}$ aralkyl, $R^{15a}$, $R^{15b}$ are the same or different and mean hydrogen, $C_1-C_{10}$ alkyl, aryl, $C_7-C_{20}$ aralkyl or together a $-(CH_2)_q$ group, Hal means halogen, o means 2 to 4, q means 3 to 6, including all stereoisomers as well as their mixtures, and free hydroxyl groups can be etherified or esterified in $R^{13}$ and $R^{14}$, free carbonyl groups can be ketalized in A and $R^{13}$, converted into an enol ether or reduced, and free acid groups in A can be converted into their salts with bases.

B stands for a C7–C12 fragment (epothilone numbering system) of general formula

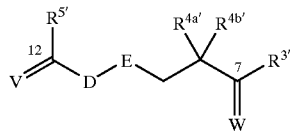

in which $R^{3'}$ means hydrogen, $C_1-C_{10}$ alkyl, aryl, $C_7-C_{20}$ aralkyl, $R^{4a'}$, $R^{4b'}$ are the same or different and mean hydrogen, $C_1-C_{10}$ alkyl, aryl, $C_7-C_{20}$ aralkyl or together a $-(CH_2)_p$ group with p=2, 3, 4 or 5, $R^{5'}$ means hydrogen, $C_1-C_{10}$ alkyl, aryl, $C_7-C_{20}$ aralkyl, D-E means a group

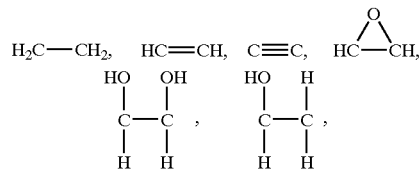

V means an oxygen atom, two alkoxy groups $OR^{17}$, a $C_2-C_{10}$ alkylene-60, ω-dioxy group, which can be straight-chain or branched or $H/OR^{16}$, W means an oxygen atom, two alkoxy groups $OR^{19}$, a $C_2-C_{10}$ alkylene-α, ω-dioxy group, which can be straight-chain or branched or $H/OR^{18}$, $R^{16}$, $R^{18}$, independently of one another, mean hydrogen or a protective group $PG^1$ $R^{17}$, $R^{19}$, independently of one another, mean $C_1-C_{20}$ alkyl.

C stands for a C13–C16 fragment (epothilone numbering system) of general formula

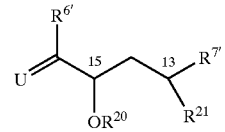

in which $R^{8'}$ means hydrogen, $C_1-C_{20}$ alkyl, aryl, $C_7-C_{20}$ aralkyl, which can all be substituted, and $R^{7'}$ means a hydrogen atom, $R^{20}$ means a hydrogen atom or a protective group $PG^2$, $R^{21}$ means a hydroxy group, halogen, a protected hydroxy group $OPG^3$, a phosphonium halide radical $PPh_3^{+Hal-}$ (Ph= phenyl; Hal=F, Cl, Br, I), a phosphonate radical $P(O)(OQ)_2$ (Q=$C_1-C_{10}$ alkyl or phenyl) or a phosphine oxide radical $P(O)Ph_2$ (Ph=phenyl), U means an oxygen atom, two alkoxy groups $OR^{23}$, a $C_2-C_{10}$ alkylene-α, ω-dioxy group, which can be straight-chain or branched, $H/OR^9$ or a grouping $CR^{10}R^{11}$, whereby
$R^{23}$ stands for a $C_1$–$C_{20}$ alkyl radical,
$R^9$ stands for hydrogen or a protective group $PG^3$,
$R^{10}$, $R^{11}$ are the same or different and stand for hydrogen, a $C_1$–$C_{20}$ alkyl, aryl, $C_7$–$C_{20}$ aralkyl radical or $R^{10}$ and $R^{11}$ together with the methylene carbon atom commonly stand for a 5- to 7-membered carbocyclic ring.

Substituents in partial fragments A, B, C:

As alkyl groups $R^{1a'}$, $R^{1b'}$, $R^{2a'}$, $R^{2b'}$, $R^{3'}$, $R^{4'}$, $R^{5'}$, $R^{8'}$, $R^9$, $R^{10}$, $R^{11}$, $R^{12}$, $R^{13b}$, $R^{14b}$, $R^{15a}$, $R^{15b}$, $R^{17}$ and $R^{23}$, straight-chain or branched-chain alkyl groups with 1–20 carbon atoms can be considered, such as, for example, methyl, ethyl, propyl, isopropyl, butyl, isobutyl, tert-butyl, pentyl, isopentyl, neopentyl, heptyl, hexyl, decyl.

Alkyl groups $R^{1a'}$, $R^{1b'}$, $R^{2a'}$, $R^{2b'}$, $R^{3'}$, $R^{4'}$, $R^{5'}$, $R^{8'}$, $R^9$, $R^{10}$, $R^{11}$, $R^{12}$, $R^{13b}$, $R^{14b}$, $R^{15a}$, $R^{15b}$, $R^{17}$ and $R^{23}$ can be perfluorinated or substituted by 1–5 halogen atoms, hydroxy groups, $C_1$–$C_4$ alkoxy groups, $C_6$–$C_{12}$ aryl groups (which can be substituted by 1–3 halogen atoms).

As aryl radicals $R^{1a'}$, $R^{1b'}$, $R^{2a'}$, $R^{2b'}$, $R^{3'}$, $R^{4'}$, $R^{5'}$, $R^{8'}$, $R^9$, $R^{10}$, $R^{11}$, $R^{12}$, $R^{13b}$, $R^{14b}$, $R^{15a}$ and $R^{15b}$, substituted and unsubstituted carbocyclic or heterocyclic radicals with one or more heteroatoms, such as, e.g., phenyl, naphthyl, furyl, thienyl, pyridyl, pyrazolyl, pyrimidinyl, oxazolyl, pyridazinyl, pyrazinyl, quinolyl, thiazolyl, which can be substituted in one or more places by halogen, OH, O-alkyl, $CO_2H$, $CO_2$-alkyl, —$NH_2$, —$NO_2$, —$N_3$, —CN, $C_1$–$C_{20}$ alkyl, $C_1$–$C_{20}$ acyl, $C_1$–$C_{20}$ acyloxy groups, are suitable. Heteroatoms in the heteroaryl radicals can be oxidized; thus, for example, the thiazole ring can be present in the form of N-oxide.

The aralkyl groups in $R^{1a'}$, $R^{1b'}$, $R^{2a'}$, $R^{2b'}$, $R^{3'}$, $R^{4'}$, $R^{5'}$, $R^{8'}$, $R^9$, $R^{10}$, $R^{11}$, $R^{12}$, $R^{13b}$, $R^{14b}$, $R^{15a}$ and $R^{15b}$ can contain in the ring up to 14 C atoms, preferably 6 to 10, and in the alkyl chain 1 to 8, preferably 1 to 4 atoms. As aralkyl radicals, for example, benzyl, phenylethyl, naphthylmethyl, naphthylethyl, furylmethyl, thienylethyl, and pyridylpropyl are suitable. The rings can be substituted in one or more places by halogen, OH, O-alkyl, $CO_2H$, $CO_2$-alkyl, —$NO_2$, —$N_3$—CN, $C_1$–$C_{20}$ alkyl, $C_1$–$C_{20}$ acyl, $C_1$–$C_{20}$ acyloxy groups.

As representatives of protective groups PG, alkyl- and/or aryl-substituted silyl, $C_1$–$C_{20}$ alkyl, $C_4$–$C_7$ cycloalkyl, which in addition to the ring can contain an oxygen atom, aryl, $C_7$–$C_{20}$ aralkyl, $C_1$–$C_{20}$ acyl and aroyl can be mentioned.

As alkyl, silyl and acyl radicals for protective groups PG, the radicals that are known to one skilled in the art are suitable. Preferred are alkyl or silyl radicals that can be easily cleaved from the corresponding alkyl and silyl ethers, such as, for example, the methoxymethyl, methoxyethyl, ethoxyethyl, tetrahydropyranyl, tetrahydrofuranyl, trimethylsilyl, triethylsilyl, tert-butyldimethylsilyl, tertbutyldiphenylsilyl, tribenzylsilyl, triisopropylsilyl, benzyl, para-nitrobenzyl, para-methoxybenzyl radical as well as alkylsulfonyl and arylsulfonyl radicals. As acyl radicals, e.g., formyl, acetyl, propionyl, isopropionyl, pivalyl, butyryl or benzoyl, which can be substituted with amino and/or hydroxy groups, are suitable.

Acyl groups $PG^x$ or $PG^z$ in $R^9$ and $R^{12}$ can contain 1 to 20 carbon atoms, whereby formyl, acetyl, propionyl, isopropionyl and pivalyl groups are preferred.

Index m in the alkylene group that is formed from $R^{1a}$ and $R^{1b}$ preferably stands for 2, 3 or 4.

The $C_2$–$C_{10}$ alkylene-α, ω-dioxy group that is possible for X is preferably an ethyleneketal or neopentylketal group.

This invention provides for, for example, the following variants of the compounds of general formula I:

Compounds of formula I, in which $R^8$ is a hydrogen atom;
Compounds of formula I, in which $R^8$ is a methyl group;
Compounds of formula I, in which $R^8$ is a hydrogen atom, and $R^2$ is an ethyl group;
Compounds of formula I, in which $R^8$ means a hydrogen atom, and $R^{1a}$ and $R^{1b}$ together mean a trimethylene group;
Compounds of formula I, in which $R^8$ means a hydrogen atom, and $R^{1a}$ and $R^{1b}$ together mean a trimethylene group;
Compounds of formula I, in which $R^8$ means a methyl group, and $R^{1a}$ and $R^{1b}$ together mean a trimethylene group and X means a 2-pyridyl radical;
Compounds of formula I, in which $R^8$ means a hydrogen atom, and X means a 2-pyridyl radical;
Compounds of formula I, in which $R^2$ means an ethyl group, $R^{1a}$ and $R^{1b}$ together mean a trimethylene group, and X means a 2-pyridyl radical;
Compounds of formula I, in which $R^8$ means a hydrogen atom, $R^2$ means an ethyl group, and $R^{1a}$ and $R^{1b}$ together mean a trimethylene group;
Compounds of formula I, in which $R^8$ means a hydrogen atom, $R^2$ means an ethyl group, $R^{1a}$ and $R^{1b}$ together mean a trimethylene group and X means a 2-pyridyl radical.

In the case of an alkyl group, $R^4$ and $R^5$ primarily mean a methyl group.

The invention relates in particular to the compounds:

(4S,7R,8S,9S,13(E or Z),16S(E))-4,8-Dihydroxy-16-(2-(2-methyl-4-thiazolyl)ethenyl)-1-oxa-5,5,7,9,13-pentamethyl -cyclohexadec-13-ene-2,6-dione (1(S or R),3S(E),7S,10R,11S,12S,16R)-7,11-Dihydroxy-3-(2-(2-methyl-4-thiazolyl)ethenyl)-8,8,10,12,16-pentamethyl-4,17-dioxabicyclo[14.1.0]heptadeca-5,9-dione (1(R or S),3S(E),7S,10R,11S,12S,16S)-7,11-Dihydroxy-3-(2-(2-methyl-4-thiazolyl)ethenyl)-8,8,10,12,16-pentamethyl-4,17-dioxabicyclo[14.1.0]heptadeca-5,9-dione 4S,7R,8S,9S,13(E or Z),16S(E))-4,8-Dihydroxy-7-ethyl-16-(2-(2-methyl-4-thiazolyl)ethenyl)-1-oxa-5,5,9,13-tetramethyl -cyclohexadec-13-ene-2,6-dione (1(S or R),3S(E),7S,10R,11S,12S,16R)-7,11-Dihydroxy-10-ethyl-3-(2-(2-methyl-4-thiazolyl)ethenyl)-8,8,12,16-tetramethyl -4,17-dioxabicyclo[14.1.0]heptadeca-5,9-dione (1(R or S),3S(E),7S,10R,11S,12S,16S)-7,11-Dihydroxy-10-ethyl-3-(2-(2-methyl-4-thiazolyl)ethenyl)-8,8,12,16-tetramethyl -4,17-dioxabicyclo[14.10]heptadeca-5,9-dione (4S,7R,8S,9S,13(E or Z),16S(E))-4,8-Dihydroxy-16-(1-methyl -2-(2-pyridyl)ethenyl)-1-oxa-5,5-(1,3-trimethylene)-7,9,13-trimethyl-cyclohexadec-13-ene-2,6-dione (1(S or R),3S(E),7S,10R,11S,12S,16R)-7,11-Dihydroxy-3-(1-methyl-2-(2-pyridyl)ethenyl)-8,8-(1,3-trimethylene)-10,12,16-trimethyl-4,17-dioxabicyclo[14.1.0]heptadeca-5,9-dione (1(R or S), 3S(E),7S,10R,11S,12S,16S)-7,11-Dihydroxy-3-(1-methyl-2-(2-pyridyl)ethenyl)-8,8-(1,3-trimethylene)-10,12,16-trimethyl-4,17-dioxabicyclo[14.1.0]heptadeca-5,9-dione (4S,7R,8S,9S,13(E or Z),16S(E))-4,8-Dihydroxy-16-(2-(2-methyl-4-thiazolyl)ethenyl)-1-oxa-5,5-(1,3-trimethylene)-7,9,13-trimethyl-cyclohexadec-13-ene-2,6-dione (1(S or R),3S(E),7S,10R,11S,12S,16R)-7,11-Dihydroxy-3-(2-(2-methyl-4-thiazolyl)ethenyl)-8,8-(1,3-trimethylene)-10,12,16-trimethyl-4,17-dioxabicyclo[14.1.0]heptadeca-5,9-dione (1(R or S),3S(E),7S,10R,11S,12S,16S)-7,11-Dihydroxy-3-(2-(2-methyl-4-thiazolyl)ethenyl)-8,8-(1,3-trimethylene)-10,12,16-trimethyl-4,17-dioxabicyclo[14.1.0]heptadeca-5,9-dione (4S,7R,8S,9S,13(E or Z),16S(E))-4,8-Dihydroxy-16-(2-(2-pyridyl)ethenyl)-1-oxa-5,5,7,9,13-pentamethyl-cyclohexadec-13-ene-2,6-dione (1(S or R),3S(E),7S,10R,11S,12S,16R)-7,11-Dihydroxy-3-(2-(2-pyridyl)ethenyl)-8,8,10,12,16-pentamethyl-4,17-dioxabicyclo[14.1.0]heptadeca-5,9-dione (1(R or S),3S(E),7S,10R,11S,12S,16S)-7,11-Dihydroxy-3-(2-(2-pyridyl)ethenyl)-8,8,10,12,16-pentamethyl-4,17-dioxabicyclo[14.1.0]heptadeca-5,9-dione (4S,7R,8S,9S,13(E or Z),16S(E)))-4,8-Dihydroxy-7-ethyl-16-(1-methyl-2-(2-pyridyl)ethenyl)-1-oxa-5,5,-(1,3-trimethylene) -9,13-dimethyl-cyclohexadec-13-ene-2,6-dione (1(S or R),3S(E),7S,10R,11S,12S,16R)-7,11-Dihydroxy-10-ethyl-3-(1-methyl-2-(2-pyridyl)ethenyl)-8,8-(1,3-trimethylene) -12,16-dimethyl-4,17-dioxabicyclo[14.1.0]heptadeca-5,9-dione (1(R or S),3S(E),7S,10R,11S,12S,16S)-7,11-Dihydroxy-10-ethyl-3-(1-methyl-2-(2-pyridyl)ethenyl)-8,8-(1,3-trimethylene) -12,16-dimethyl-4,17-dioxabicyclo[14.1.0]heptadeca-5,9-dione (4S,7R,8S,9S,13(E or Z),16S(E))-4,8-Dihydroxy-7-ethyl-16-(2-(2-methyl-4-thiazolyl)ethenyl)-1-oxa-5,5,-(1,3-trimethylene)-9,13-dimethyl-cyclohexadec-13-ene-2,6-dione (1(S or R),3S(E),7S,10R,11S,12S,16R)-7,11-Dihydroxy-10-ethyl-3-(2-(2-methyl-4-thiazolyl)ethenyl)-8,8-(1,3-trimethylene) -12,16-dimethyl-4,17-dioxabicyclo[14.1.0]heptadeca-5,9-dione (1(R or S),3S(E),7S,10R,11S,12S,16S)-7,11-Dihydroxy-10-ethyl-3-(2-(2-methyl-4-thiazolyl)ethenyl)-8,8-(1,3-trimethylene) -12,16-dimethyl-4,17-dioxabicyclo[14.1.0]heptadeca-5,9-dione (4S,7R,8S,9S,13(E or Z),16S(E))-4,8-Dihydroxy-7-ethyl-16-(2-(2-pyridyl)ethenyl) -1-oxa-5,5,9,13-tetramethyl-cyclohexadec-13-ene -2,6-dione (1(S or R),3S(E),7S,10R,11S,12S,16R)-7,11-Dihydroxy-10-ethyl-3-(2-(2-pyridyl)ethenyl)-8,8,12,16-tetramethyl-4,17-dioxabicyclo[14.1.0]heptadeca-5,9-dione (1(R or S),3S(E),7S,10R,11S,12S,16S)-7,11-Dihydroxy-10-ethyl-3-(2-(2-pyridyl)ethenyl)-8,8,12,16-tetramethyl-4,17-dioxabicyclo[14.1.0]heptadeca-5,9-dione (4S,7R,8S,9S,13(E or Z),16S(E))-4,8-Dihydroxy-7-ethyl-16-(2-(2-pyridyl)ethenyl)-1-oxa-5,5-(1,3-trimethylene)-9,13-dimethyl -cyclohexadec-13-ene-2,6-dione (1(S or R),3S(E),7S,10R,11S,12S,16R)-7,11-Dihydroxy-10-ethyl-3-(2-(2-pyridyl)ethenyl)-8,8-(1,3-trimethylene)-12,16-dimethyl-4,17-dioxabicyclo[14.1.0]heptadeca-5,9-dione (1(R or S),3S(E),7S,10R,11S,12S,16S)-7,11-Dihydroxy-10-ethyl-3-(2-(2-pyridyl)ethenyl)-8,8-(1,3-trimethylene)-12,16-dimethyl-4,17-dioxabicyclo[14.1.0]heptadeca-5,9-dione (4S,7R,8S,9S,13Z,16S(E))-4,8-Dihydroxy-16-(1-methyl-2-(2-pyridyl)ethenyl)-1-oxa-7-propyl-5,5,9,13-tetramethyl -cyclohexadec-13-ene-2,6-dione (1S,3S(E),7S,10R,11S,12S,16R)-10-Propyl-7,11-dihydroxy-3-(1-methyl-2-(2-N-oxidopyridyl)ethenyl)-8,8,12,16-tetramethyl-4,17-dioxabicyclo[14.1.0]heptadeca-5,9-dione (1R,3S(E),7S,10R,11S,12S,16S)-10-Propyl-7,11-dihydroxy-3-(1-methyl-2-(2-N-oxidopyridyl)ethenyl)-8,8,12,16-tetramethyl-4,17-dioxabicyclo[14.1.0]heptadeca-5,9-dione (1S,3S(E),7S,10R,11S,12S,16R)-10-Propyl-7,11-dihydroxy-3-(1-methyl-2-(2-pyridyl)ethenyl)-8,8,12,16-tetramethyl-4,17-dioxabicyclo[14.1.0]heptadeca-5,9-dione (1R,3S(E),7S,10R,11S,12S,16S)-10-Propyl-7,11-dihydroxy-3-(1-methyl-2-(2-pyridyl)ethenyl)-8,8,12,16-tetramethyl-4,17-dioxabicyclo[14.1.0]heptadecane-5,9-dione (4S,7R,8S,9S,13E,16S(E))-4,8-Dihydroxy-16-(1-methyl-2-(2-pyridyl)ethenyl)-1-oxa-7-propyl-5,5,9,13-tetramethyl -cyclohexadec-13-ene-2,6-dione (1R,3S(E),7S,10R,11S,12S,16R)-10-Propyl-7,11-dihydroxy-3-(1-methyl-2-(2-N-oxidopyridyl) ethenyl)-8,8,12,16-tetramethyl-4,17-dioxabicyclo[14.1.0]heptadeca-5,9-dione (1S,3S(E),7S,10R,11S,12S,16S)-10-Propyl-7,11-dihydroxy-3-(1-methyl-2-(2-N-oxidopyridyl)ethenyl)-8,8,12,16-tetramethyl-4,17-dioxabicyclo[14.1.01]heptadeca-5,9-dione (1R,3S(E),7S,10R,11S,12S,16R)-10-Propyl-7,11-dihydroxy-3-(1-methyl-2-(2-pyridyl)ethenyl)-8,8,12,16-tetramethyl-4,17-dioxabicyclo[14.1.0]heptadeca-5,9-dione (1S,3S(E),7S,10R,11S,12S,16S)-10-Propyl-7,11-dihydroxy-3-(1-methyl-2-(2-pyridyl)ethenyl)-8,8,12,16-tetramethyl-4,17-dioxabicyclo[14.1.0]heptadeca-5,9-dione.

Representation of Partial Fragments A (DE 197 51 200.3, date of application Nov. 13, 1997 as well as the corresponding PCT/EP98/05064)

It is known that the compound of the following formula

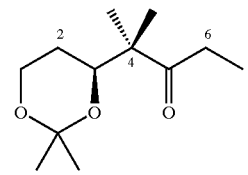

can be used for synthesis of the C1–C6 fragment (epothilone numbering system) of epothilone A (Schinzer et al., Chem. Eur. J. 1996, 2, No. 11, 1477–1482; Schinzer et al., Angew. Chem., 1997, 109, No. 5, pp. 543–544).

This synthesis has the drawback that the total yield at 10.5% being very low, the necessary introduction of chirality at C-atom 3 requires the synthesis of a costly, chemically unstable chiral adjuvant that can be used in equimolar amounts and cannot be recovered, and at about 80% the optical induction that this provides is incomplete.

For an industrially applicable synthesis, however, high yields and high optical purity are necessary.

In Angew. Chem. 1997, 109, No. 1/2, pp. 170–172, the synthesis of a (C1–C6) component with a carboxyl group at C-1, which can be used for the synthesis of epothilone or epothilone derivatives,

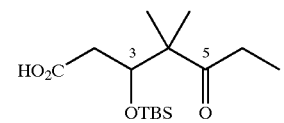

(TBS=tert-butyldimethylsilyl) is described by Nicolaou et al. The stereochemisty at C3 is controlled by the reaction with the Brown reagent allylisopinocamphenylborane (+)-Ipc$_2$B (allyl), which must be introduced into the reaction in an equimolar ratio and cannot be recovered.

The use of this component for synthesis of epothilone A and B and some epothilone analogs in Nature, Vol. 387, 1997, pp. 268–272 for the synthesis of epothilone A and its derivatives in J. Am. Chem. Soc., Vol. 119, No. 34, 1997, pp. 7960–7973 and for synthesis of epothilone A and B and some epothilone analogs in J. Am. Chem. Soc., Vol. 119, No. 34, 1997, pp. 7974–7911 is also described by Nicolaou et al.

The production of epothilone A-analogs by means of combinatory solid-phase synthesis is also described by Nicolaou et al. in Angew. Chem. 1997, 109, No. 19, pp. 2181–2187. This source also describes epothilone B-analogs. As C1–C6 components, the compounds below are used:

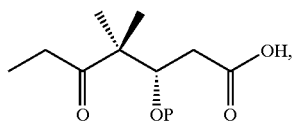

P = TBS

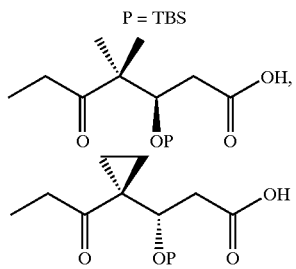

For an industrially applicable synthesis, it is advantageous if the synthesis can be performed without costly chiral auxiliary groups.

The object was therefore to find a suitable synthesis that produces high yields, produces the desired product in high optical purity and does not require costly chiral auxiliary groups.

In addition, the new synthesis should allow a broader variation of substituents in this component and thus ultimately allow the epothilone derivatives to be produced therefrom.

The partial fragments (synthesis components) of general formula A can be easily produced as starting products from a) a pantolactone of general formula IIa

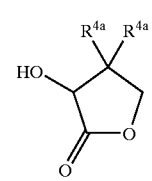

IIa in which

R$^{1a'}$, R$^{1b'}$ in each case stand for a methyl group, or b) a malonic acid dialkyl ester of general formula XXVIII

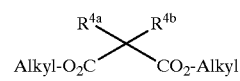

XXVIII in which

R$^{1a'}$, R$^{1b'}$ have the meaning that is indicated in general formula A, and alkyls, independently of one another, mean a C$_1$–C$_{20}$ alkyl, C$_3$–C$_{10}$ cycloalkyl or C$_4$–C$_{20}$ alkylcycloalkyl radical.

Partial fragments A, in which R$^{1a'}$=R$^{1b'}$=methyl, can be efficiently produced from inexpensive pantolactone with an optical purity of >98%.

The synthesis is described in diagram 1 below in the example of D-(−)-pantolactone. From L-(+)-pantolactone are obtained the enantiomeric compounds ent-A-II to ent-A-XIV that correspond to A-II to A-XIV, and from racemic DL-pantolactone are obtained the corresponding racemic compounds rac-A-II to rac-A-XIV:

Reaction scheme 1

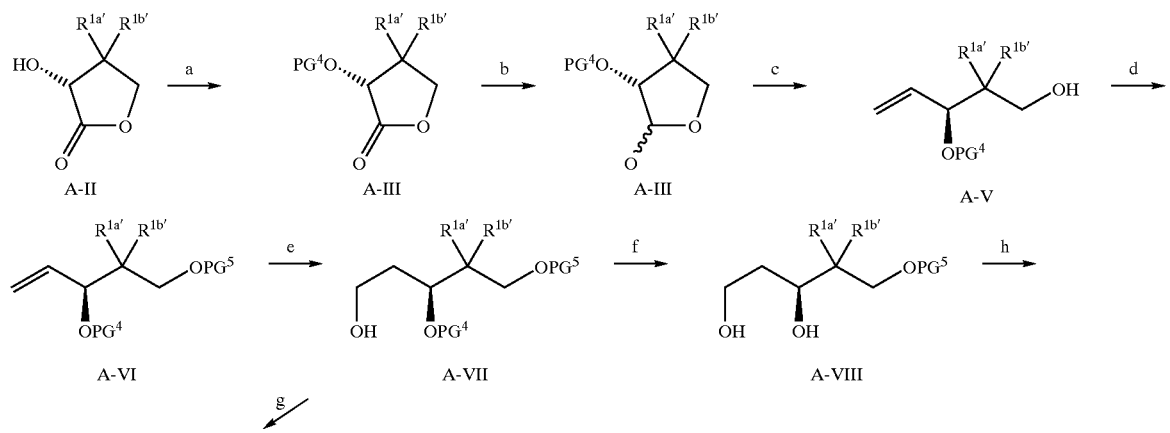

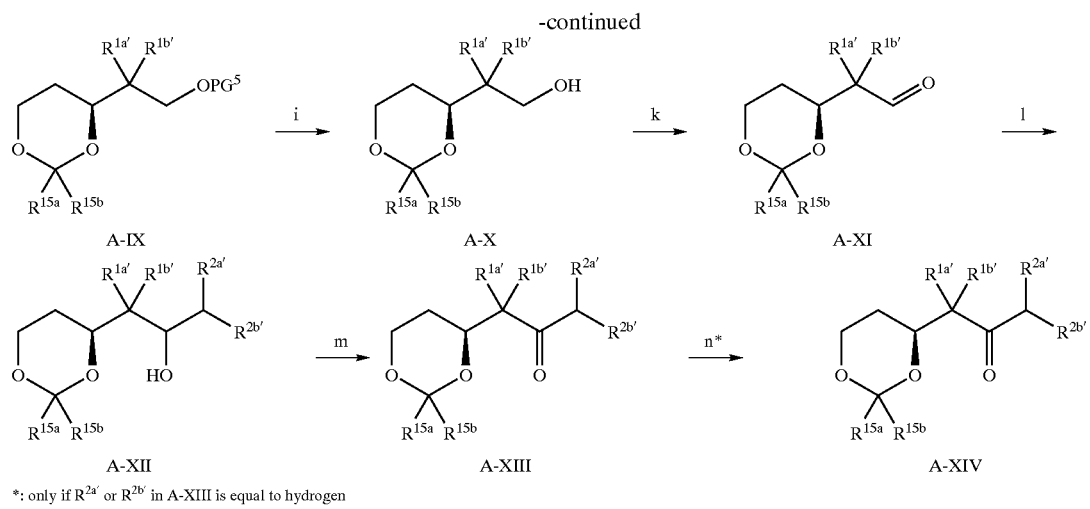

*: only if $R^{2a'}$ or $R^{2b'}$ in A-XIII is equal to hydrogen

Step a (A-II ### A-III):

The free hydroxy group of pantolactone (A-II) is protected according to the methods that are known to one skilled in the art. As protective group $PG^4$, the protective groups that are known to one skilled in the art, such as, e.g., methoxymethyl, methoxyethyl, ethoxyethyl, tetrahydropyranyl, tetrahydrofuranyl, trimethylsilyl, triethylsilyl, tert-butyldimethylsilyl, tertbutyldiphenylsilyl, tribenzylsilyl, triisopropylsilyl, benzyl, para-nitrobenzyl, para-methoxybenzyl, formyl, acetyl, propionyl, isopropionyl, pivalyl, butyryl or benzoyl radicals are suitable.

A survey is found in, e.g., "Protective Groups in Organic Synthesis" Theodora W. Green, John Wiley and Sons).

Preferred are those protective groups that can be cleaved under acidic reaction conditions, such as; e.g., methoxymethyl, tetrahydropyranyl, tetrahydrofuranyl, and trimethylsilyl radicals.

Especially preferred is the tetrahydropyranyl radical.

Step b (A-III ### A-IV):

Protected lactone A-III is reduced to lactol A-IV. As a reducing agent, aluminum hydrides that are modified in their reactivity, such as, e.g., diisobutylaluminum hydride, are suitable. The reaction is carried out in an inert solvent such as, e.g., toluene, preferably at low temperatures.

Step c (A-IV ### A-V):

Lactol A-IV is opened up to form hydroxyolefin A-V while expanding by one C atom. For this purpose, the methods that are known to one skilled in the art, such as, e.g., olefination according to Tebbe, the Wittig or Wittig/Horner reaction, the addition of an organometallic compound with dehydration, are suitable. Preferred is the Wittig reaction with use of methyltriarylphosphonium halides, such as, e.g., methyltriphenylphosphonium bromide with strong bases, such as, e.g., n-butyllithium, potassium-tert-butanolate, sodium ethanolate, and sodium hexamethyldisilazane; as a base, n-butyllithium is preferred.

Step d (A-V ### A-VI):

The free hydroxy group in A-V is protected according to the methods that are known to one skilled in the art. As protective group $PG^5$; the protective groups that are known to one skilled in the art, as were already mentioned above for $PG^4$ in step a (A-II ### A-III), are suitable.

Preferred are those protective groups that can be cleaved under the action of fluoride, such as, e.g., the trimethylsilyl, tert-butyldimethylsilyl, tert-butyldiphenylsilyl, tribenzylsilyl, and triisopropylsilyl radical.

Especially preferred is the tert-butyldimethylsilyl, the triisopropylsilyl and the tert-butyldiphenylsilyl radical.

Step e (A-VI ### A-VII):

Water is added to the double bond in A-VI in an anti-Markovnikov orientation. For this purpose, the processes that are known to one skilled in the art, such as, e.g., the reaction with boranes, their subsequent oxidation to the corresponding boric acid esters and their saponification, are suitable. As boranes, e.g., the borane-tetrahydrofuran complex, the borane-dimethyl sulfide complex, 9-borabicyclo [3.3.1]nonane in an inert solvent such as, for example, tetrahydrofuran or diethyl ether, are preferred. As an oxidizing agent, preferably hydrogen peroxide is used; for saponification of the boron esters, preferably alkali hydroxides, such as, e.g., sodium hydroxide, are used.

Step f (A-VI ### A-VII):

Protective group $PG^4$ that is introduced under step a) is now cleaved according to the processes that are known to one skilled in the art. If this is a protective group that can be cleaved acidically, then cleavage can be accomplished with dilute mineral acids in aqueous-alcoholic solutions and with the aid of catalytic amounts of acids, such as, e.g., para-toluenesulfonic acid, para-toluenesulfonic acid-pyridinium salt, camphorsulfonic acid in alcoholic solutions, preferably in ethanol or isopropanol.

Step g (A-VII ### A-IX):

Common protection of the two alcohol functions of the mono-protected 1,3-diol in A-VII is possible under acidic catalysis by direct ketalization with a carbonyl compound of general formula $R^{15a}$—CO—$R^{15b}$ or by reketalization with a ketal of general formulas $R^{15a}$—C(OC$_2$H$_5$)$_2$—$R^{15b}$, $R^{15a}$—C(OC$_2$H$_4$)$_2$—$R^{15b}$, $R^{15a}$—C(OCH$_2$C(CH$_3$)$_2$CH$_2$O)—$R^{15b}$, in which in each case $R^{15a}$ and $R^{15b}$ have the above-indicated meanings. As acids, the acids already mentioned under step f) are suitable; the use of para-toluenesulfonic acid optionally with the addition of copper(II) or cobalt(II) salts, such as, e.g., copper(II) sulfate, is preferred.

Step h (A-VIII ### A-IX):

Protection of the two alcohol functions of 1,3-diol in A-VIII is possible under acidic catalysis by direct ketalization with a carbonyl compound of general formula $R^{15a}$—CO—$R^{15b}$, or by reketalization with a ketal of general formulas $R^{15a}$—C(OC$_2$H$_5$)$_2$—$R^{15b}$, $R^{15a}$—C(OC$_2$H$_4$)$_2$—$R^{15b}$, $R^{15a}$—C(OCH$_2$C(CH$_3$)$_2$CH$_2$O)—$R^{15b}$, in which in each case $R^{15a}$ and $R^{15b}$ have the above-indicated meanings. Reketalization preferably with 2,2-dimethoxypropane is preferred. As acids, the acids that are already mentioned under step f) are suitable, and the use of camphorsulfonic acid is preferred.

Step i (A-IX ### A-X):

Protective group PG$^5$ introduced under step d) is now cleaved according to the process that is known to one skilled in the art. If this is a silyl ether, then the reaction with fluorides, such as, for example, tetrabutylammonium fluoride, hydrogen fluoride-pyridine complex, potassium fluoride or the use of dilute mineral acids, the use of catalytic amounts of acids, such as, e.g., para-toluenesulfonic acid, para-toluenesulfonic acid-pyridinium salt, camphorsulfonic acid in alcoholic solutions, preferably in ethanol or isopropanol, is suitable for the cleavage.

Step k (A-X ### A-XI):

The oxidation of the primary alcohol in A-X to aldehyde is carried-out according to the methods that are known to one skilled in the art. For example, the oxidation with pyridinium chlorochromate, pyridinium dichromate, chromium trioxide-pyridine complex, the oxidation according to Swern or related methods, e.g., with use of oxalyl chloride in dimethyl sulfoxide, the use of Dess-Martin periodinane, the use of nitrogen oxides, such as, e.g., N-methyl-morpholino-N-oxide in the presence of suitable catalysts, such as, e.g., tetrapropylammonium perruthenate in inert solvents, can be mentioned. Preferred is the oxidation according to Swern, as well as with N-methyl-morpholino-N-oxide using tetrapropylammonium perruthenate.

Step l (A-XI ### A-XII):

The reaction of aldehydes A-XI to form alcohols of formula A-XII is carried out with organometallic compounds of general formula M—CHR$^{2a'}$R$^{2b'}$, in which M stands for an alkali metal, preferably lithium or a divalent metal MX, in which X represents a halogen, and radicals $R^{2a'}$ and $R^{2b'}$ in each case have the above-mentioned meanings. As a divalent metal, magnesium and zinc are preferred; as halogen X, chlorine, bromine and iodine are preferred.

Step m (A-XII ### A-XIII):

The oxidation of the secondary alcohol in A-XII to ketone A-XIII is carried out according to the conditions that are mentioned under step k). The oxidation with N-methyl-morpholino-N-oxide with use of tetrapropylammonium perruthenate is preferred.

Step n (A-XIII ### A-XIV):

If $R^{2a'}$ in A-XIII is equal to hydrogen, the possibility exists of introducing for this purpose a second radical $R^{2a'}$, which has the above-mentioned meanings, excluding hydrogen. For this purpose, ketone in A-XIII is converted into the enolate with use of strong bases, such as, e.g., lithium diisopropylamide, and reacted with a compound of general formula X-$R^{2a'}$, in which X represents a halogen. As halogen X, chlorine, bromine and iodine are preferred.

The previously described path can also be used to synthesize C1–C6-epothilone components, which on C-1 contain a carboxylic acid or esters thereof ($R^{13}$═CO$_2$R$^{13b}$ in A).

The synthesis of component A-XXII is described in Diagram 2 below in the example of intermediate stage A-V that is derived from D-(–)-pantolactone. The enantiomer compounds ent-A-V to ent-A-XXVII corresponding to A-V to A-XXVII are obtained from L-(+)-pantolactone, and the corresponding racemic compounds rac-A-V to rac-A-XXVII are obtained from racemic DL-pantolactone:

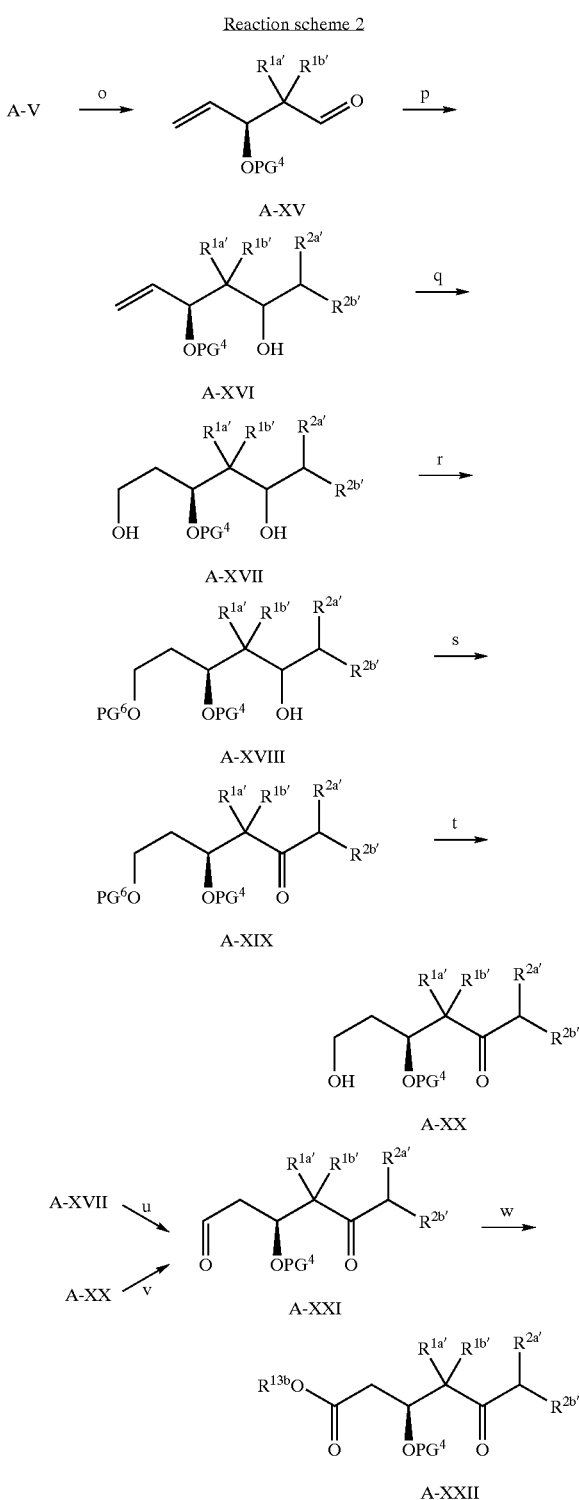

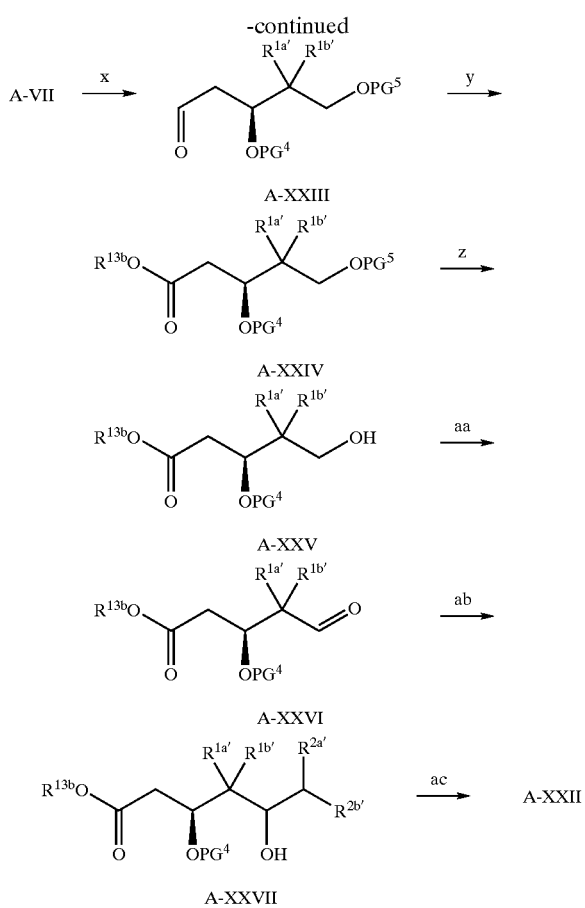

Step o (A-V ### A-XV):

The oxidation of the primary alcohol in A-V to aldehyde A-XV is carried out according to the conditions that are mentioned under step k). The oxidation process according to Swern is preferred.

Step p (A-XV ### A-XVI):

The reaction of aldehydes A-XV to form alcohols of formula A-XVI is carried out with organometallic compounds of general formula M-CHR$^{2a'}$R$^{2b'}$, in which M stands for an alkali metal, preferably lithium or a divalent metal MX, in which X represents a halogen, and radicals R$^{2a'}$ and R$^{2b'}$ in each case have the above-mentioned meanings. As a divalent metal, magnesium and zinc are preferred; as halogen X, chlorine, bromine and iodine are preferred.

Step q (A-XVI # A-XVII):

Water is added to the double bond in A-XVI in an anti-Markovnikov orientation. For this purpose, the processes that are described under e) are suitable.

Step r (A-XVII ### A-XVIII):

The free hydroxy group in A-XVII is protected according to the methods that are known to one skilled in the art. As protective group PG$^6$, the protective groups that are known to one skilled in the art, as were already mentioned above for PG$^4$ in step a (A-II ### A-III), are suitable.

Preferred are those protective groups that can be cleaved under basic or hydrogenolytic reaction conditions, such as, e.g., benzyl, para-nitrobenzyl, acetyl, propionyl, butyryl and benzoyl radicals.

Especially preferred is the benzoyl radical.

Step s (A-XVIII ### A-XIX):

The oxidation of the secondary alcohol in A-XVII to form ketone A-XIX is carried out according to the conditions that are mentioned under step k). Preferred is the oxidation with N-methyl-morpholino-N-oxide with use of tetrapropylammonium perruthenate.

Step t (A-XIX ### A-XX):

Protective group PG$^6$ in XIX is now selectively cleaved. If this is a hydrogenolytically cleavable protective group, then it is preferably hydrogenated in the presence of palladium or platinum catalysts in inert solvents, such as, for example, ethyl acetate or ethanol. If this is a basically cleavable protective group, then saponification with carbonates in alcoholic solution, such as, e.g., potassium carbonate in methanol, saponification with aqueous solutions of alkali hydroxides, such as, e.g., lithium hydroxide or sodium hydroxide, are preferably used while employing organic, water-miscible solvents, such as, e.g., methanol, ethanol, tetrahydrofuran or dioxane.

Step u (A-XVII ### A-XXI):

The oxidation of alcohols in A-XVII to form ketoaldehyde A-XXI is carried out according to the conditions that are mentioned under step k). Preferred is the oxidation with N-methylmorpholino-N-oxide with use of tetrapropylammonium perruthenate and the method according to Swern.

Step v (A-XX ### A-XXI):

The oxidation of the primary alcohol in A-XX to form ketoaldehyde A-XXI is carried out according to the conditions that are mentioned under step k). Preferred is the oxidation with N-methyl-morpholino-N-oxide with use of tetrapropylammonium perruthenate.

Step w (A-XXI ### A-XXII):

The oxidation of the aldehyde in A-XXI to form carboxylic acid A-XXII (R$^{13}$b=hydrogen) is carried out according to the methods that are known to one skilled in the art. For example, the oxidation according to Jones, the oxidation with potassium permanganate, for example in an aqueous system that consists of tert-butanol and sodium dihydrogen phosphate, the oxidation with sodium chlorite in aqueous tert-butanol optionally in the presence of a chlorine trap, such as, e.g., 2-methyl-2-butene, can be mentioned.

The oxidation of the aldehyde in A-XXI to form ester A-XXII, in which R$^{13b}$ has the above-mentioned meanings and is unequal to hydrogen, can be carried out, for example, with pyridinium dichromate and the desired alcohol HO—R$^{13b}$ in an inert solvent, such as, e.g., dimethylformamide.

Step x (A-VII ### A-XXIII):

The oxidation of the primary alcohol in A-VII to form aldehyde A-XXIII is carried out according to the conditions that are mentioned under step k). Preferred is the oxidation with N-methyl-morpholino-N-oxide with use of tetrapropylammonium perruthenate as well as the method according to Swern.

Step y (A-XXIII ### A-XXIV):

The oxidation of aldehyde A-XXIII to form carboxylic acid or its esters A-XXIV is carried out according to the conditions already described under w).

Step z (A-XXIV ### A-XXV):

Protective group PG$^5$ that is introduced under step d) is cleaved as described under step i.

Step aa (A-XXV ### A-XXVI):

The oxidation of the primary alcohol in A-XXV to form aldehyde A-XXVI is carried out according to the conditions that are mentioned under step k). Preferred is the oxidation with N-methyl-morpholino-N-oxide with use of tetrapropylammonium perruthenate as well as the method according to Swern.

Step ab (A-XXVI ### A-XXVII):

The reaction of aldehyde A-XXVI to form alcohols of formula A-XXVII is carried out according to the conditions that are mentioned under step l).

Step ac (A-XXVII ### A-XXII):

The oxidation of the secondary alcohol in A-XXVII to form ketone A-XXII is carried out according to the conditions that are mentioned under step k). Preferred is the oxidation with N-methyl-morpholino-N-oxide with use of tetrapropylammonium perruthenate.

The compounds of formula A, in which $R^{1a'}$ and $R^{1b'}$ all can have the meanings that are indicated in general formula A, can also be produced from inexpensive or readily available malonic acid dialkyl esters in an efficient way with high optical purity.

The synthesis is described in scheme 3 below:

art. As protective group $PG^7$, the protective groups that are known to one skilled in the art, as were already mentioned above for $PG^4$ in step a (A-II ### A-III), are suitable.

Preferred are silicon-containing protective groups.

Step af (A-XXX ### A-XXXI):

The oxidation of the remaining, primary hydroxyl group in A-XXX to form aldehyde A-XXXI is carried out according to the conditions that are mentioned under step k). Preferred is the oxidation with N-methyl-morpholino-N-oxide with use of tetrapropylammonium perruthenate, the use of pyridinium chlorochromate, pyridinium dichromate as well as the method according to Swern.

Step ag (A-XXXI ### A-XXXII):

Aldehydes A-XXXI are reacted with an ester of acetic acid $chG^1OC(O)CH_3$, in which $chG^1$ means a chiral auxiliary group, in terms of an aldol reaction. Compounds $chG^1OC(O)CH_3$ are used in optically pure form in the aldol reaction. The type of chiral auxiliary group determines whether the aldol reaction proceeds with high diastereoselectivity or yields a diastereomer mixture that can be separated with physical methods. A survey on comparable diastereoselective aldol reactions is found in Angew. Chem. 99 (1987), 24–37. As chiral auxiliary groups $chG^1$-OH, for

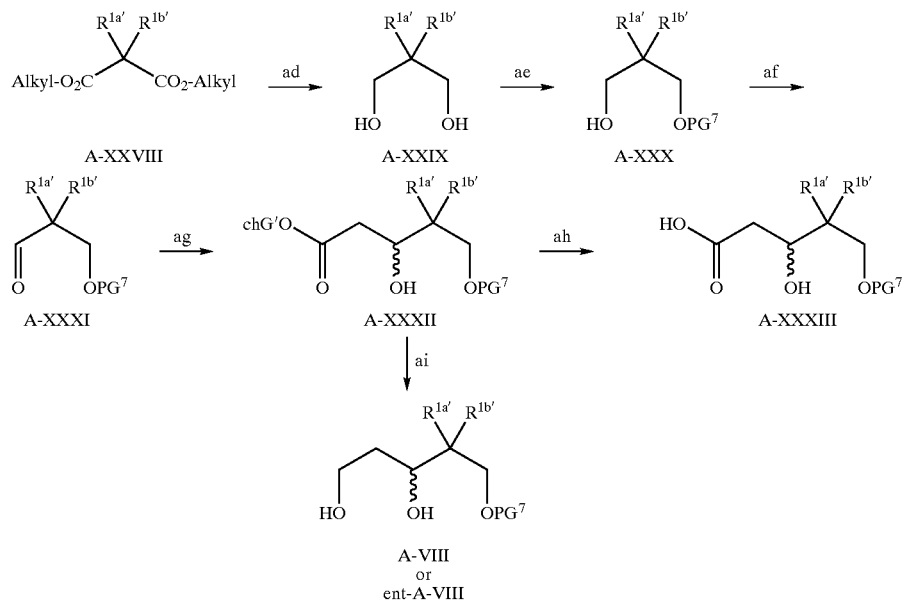

Reaction scheme 3

Step ad (A-XXVIII ### A-XXIX):

Correspondingly substituted malonic acid ester derivatives A-XXVIII, which are either commercially available or can be produced according to the processes that are known to one skilled in the art from malonic acids or their alkyl esters, are reduced to diols A-XXIX. For this purpose, the reducing agents that are known to one skilled in the art, such as, e.g., diisobutylaluminum hydride, and complex metal hydrides, such as, e.g., lithium aluminum hydride, are suitable.

Step ae (A-XXIX ### A-XXX):

A free hydroxyl group in A-XXIX is selectively protected according to the methods that are known to one skilled in the example, optically pure 2-phenyl-cyclohexanol, pulegol, 2-hydroxy-1,2,2-triphenylethanol, and 8-phenylmenthol are suitable.

Step ah (A-XXXII ### A-XXXIII):

Diastereomer-pure compounds A-XXXII can then be converted according to the process that is known to one skilled in the art by saponification of the ester unit with simultaneous release of reusable chiral auxiliary component $chG^1$-OH into enantiomer-pure compounds of type A-XXXIII or ent-A-XXXIII. For saponification, carbonates in alcoholic solution, such as, e.g., potassium carbonate in methanol, aqueous solutions of alkali hydroxides, such as, e.g., lithium hydroxide or sodium hydroxide with use of organic, water-miscible solvents, such as, e.g., methanol, ethanol, tetrahydrofuran or dioxane, are suitable.

Step ai (A-XXXII ### A-VIII):

As an alternative to step ah, the chiral auxiliary group can also be removed reductively. In this way, the enantiomer-pure compounds of type A-VIII or ent-A-VIII are obtained. The reduction can be carried out according to the processes that are known to one skilled in the art. As a reducing agent, e.g., diisobutylaluminum hydride and complex metal hydrides, such as, e.g., lithium aluminum hydride, are suitable.

Compounds A-VIII or ent-A-VIII can be converted as previously described into compounds of type A-XIII or ent-A-XIII. Correspondingly, compounds of type A-XXXIII or ent-A-XXXIII can be converted into compounds of type A-XXII or ent-A-XXII according to the processes that are described above.

As an alternative to the above-described method, the sequence can also be carried out without using chiral auxiliary group chG$^1$. In this way, racemic mixtures of compounds of type rac-A-VIII or rac-A-XXXIII are then obtained via the corresponding, racemic precursors. These mixtures can in turn be separated according to the processes for racemate cleavage, e.g., chromatography on chiral columns, known to one skilled in the art. The continuation of synthesis can also be carried-out with racemic mixtures, however.

This invention thus also relates to a process for the production of the compounds of general formula A, which is characterized in that a) a pantolactone of general formula IIa or
b) a malonic acid dialkyl ester of general formula XXVIII is used as a starting product.

In addition, this invention thus relates to the new C1–C6-epothilone components of general formula A'

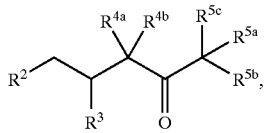

in which $R^2$ means $CH_2OR^{2a}$, CHO, $C_2R^{2b}$, COX, $R^{2a}$, $R^{2b}$ mean hydrogen, $C_1$–$C_{20}$ alkyl, aryl, $C_7$–$C_{20}$ aralkyl, $R^3$ means hydrogen, $OR^{3a}$, X, $OSO_2R^{3b}$, $R^{3a}$ means hydrogen or together with $R^{2a}$ means a —$(CH_2)_n$— group or a $CR^{6a}R^{6b}$ group, $R^{3b}$ means $C_1$–$C_4$ alkyl, aryl, X means halogen, n means 2 to 4, $R^{6a}$, $R^{6b}$ are the same or different and mean $C_1$–$C_8$ alkyl, $C_6$–$C_{10}$ aryl or together a —$(CH_2)_o$— group, o means 3 to 6, $R^{6a}$ in addition can assume the meaning of hydrogen, $R^{4a}$, $R^{4b}$ are the same or different and mean hydrogen, $C_1$–$C_{10}$ alkyl, $C_7$–$C_{20}$ aralkyl, or together a —$(CH_2)_m$— group, m means 2 to 5, $R^{5a}$, $R^{5b}$ are the same or different and mean hydrogen, $C_1$–$C_{10}$ alkyl, $C_7$–$C_{20}$aralkyl, or together a —$(CH_2)_p$— group, p means 2 to 5, $R^{5c}$ means hydrogen, including all stereoisomers and mixtures thereof, and free hydroxyl groups are etherified or esterified in $R^2$ and $R^3$, free carbonyl groups are ketalized in A and $R^2$, converted into an enol ether or reduced, and free acid groups in A can be converted into their salts with bases, excluding the compounds

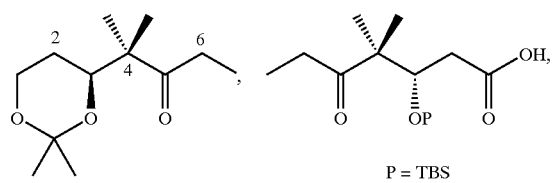

P = TBS

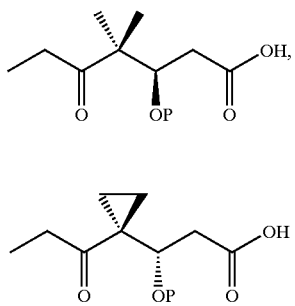

It was also found that synthesis components of general formula A''

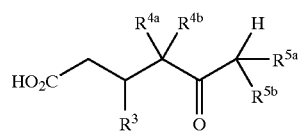

in which $R^3$ means $OR^{3a}$ and $R^{3a}$ means-hydrogen or a protective group PG $R^{4a}$, $R^{4b}$ are the same or different and mean hydrogen, $C_1$–$C_{10}$ alkyl, $C_7$–$C_{20}$ aralkyl or together a—$(CH_2)_m$— group, m means 2 to 5, $R^{5a}$, $R^{5b}$ are the same or different and mean hydrogen, $C_1$–$C_{10}$ alkyl, $C_7$–$C_{20}$ aralkyl, or together a—$(CH_2)_p$— group, p means 2 to 5, including all stereoisomers as well as their mixtures and free carbonyl groups in 1, can be readily ketalized by reaction of a compound of general formula II

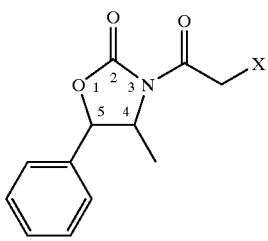

II in which
X is a chlorine or bromine atom, and the 2-oxazolidinone ring has either (4R,5S)- or (4S,5R)-conformation, with a compound of general formula III

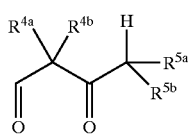

III in which
$R^{4a}$, $R^{4b}$ are the same or different and mean hydrogen, $C_1$–$C_{10}$ alkyl, $C_7$–$C_{20}$ aralkyl or together a —$(CH_2)_m$ group,
m means 2 to 5,
$R^{5a}$, $R^{5b}$ are the same or different and mean hydrogen, $C_1$–$C_{10}$ alkyl, $C_7$–$C_{20}$ aralkyl, or together a —$(CH_2)_p$ group,
p means 2 to 5, to form a compound of general formula IV

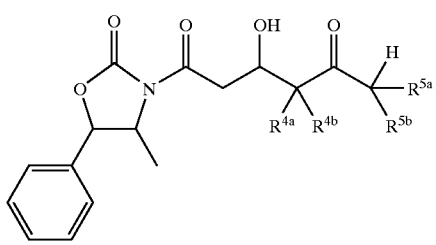

IV in which
the 2-oxazolidin one ring has (4R,5S)-conformation, and the 3'-carbon atom has R-conformation, or
the 2-oxazolidinone ring has (4S,5R)-conformation and the 3'-carbon atom has S-conformation, and can be produced under protection of the 3'-hydroxy group in IV with a protective group PG, by cleavage of the oxazolidinone radical and optionally cleavage of protective group PG.

The reaction of a compound of general formula II with a compound of general formula III can be carried out after conversion of the compound of general formula II into a metal enolate by insertion of a metal or metal salt into the carbon-halogen bond of the compound of general formula II.

As a metal or metal salt, generally all metals or metal salts that are known to one skilled in the art are suitable that are suitable for a Reformatzky reaction (see, e.g., A. Furstner, Synthesis 1989, 571–590).

According to the invention, chromium(II) chloride is preferably used.

The oxazolidinone ring is recovered almost quantitatively and without loss of optical activity in the cleavage from the compounds of general formula IV.

As alkyl groups $R^{4a}$, $R^{4b}$, $R^{5a}$ and $R^{5b}$, straight-chain or branched-chain alkyl groups with 1 to a maximum of 10 carbon atoms can be considered, such as, for example, methyl, ethyl, propyl, isopropyl, butyl, isobutyl, tert-butyl, pentyl, isopentyl, neopentyl, heptyl, hexyl, and decyl.

Alkyl groups $R^{4a}$, $R^{4b}$, $R^{5a}$ and $R^{5b}$ can be perfluorinated or substituted by 1–5 halogen atoms, hydroxy groups, $C_1$–$C_4$ alkoxy groups and $C_6$–$C_{12}$ aryl groups (which can be substituted by 1–3 halogen atoms).

The aralkyl groups in $R^{4a}$, $R^{4b}$, $R^{5a}$ and $R^{5b}$ can contain up to 14 C atoms, preferably 6 to 10 C atoms, in the ring, and 1 to 8, preferably 1 to 4 atoms, in the alkyl chain. As aralkyl radicals, for example, benzyl, phenylethyl, naphthylmethyl, naphthylethyl, furylmethyl, thienylethyl, and pyridylpropyl are considered. The rings can be substituted in one to three places by halogen, OH, O-alkyl, $NH_2$, $CO_2H$, $CO_2$-alkyl, —$NO_2$, —$N_3$, —CN, $C_1$–$C_{20}$ alkyl, $C_1$–$C_{20}$ acyl, $C_1$–$C_{20}$ acyloxy groups.

As protective group PG, all radicals that are known to one skilled in the art as such protective groups are considered. Preferred in this case are silyl-containing protective groups, such as, for example, the trimethylsilyl, triethylsilyl, tert-butyldimethylsilyl, tert-butyldiphenylsilyl, tribenzylsilyl, and triisopropylsilyl radicals.

There is a survey on protective groups in, e.g., "Protective Groups in Organic Synthesis," Theodora W. Green, John Wiley and Sons).

Halogen means fluorine, chlorine, bromine, and iodine.

The compounds of general formula II that are required for the process according to the invention are accessible by acetylation of (4R,5S)— or (4S,5R)-4-methyl-5-phenyl-2-oxazolidinone with bromo- or chloroacetyl chloride in the presence of a strong base, such as, for example, n-butyllithium.

The stereochemistry of the hydroxy group in 3-position is later controlled by the selection of the chiral auxiliary group.

The compounds of general formula III that are required for the process according to the invention are commercially available or can be produced simply.

If the compounds of general formula III are not commercially available, they can be produced, for example, according to the methods that are indicated in reaction schemes α and β.

Reaction scheme α: Starting material is (substituted) malonic ester

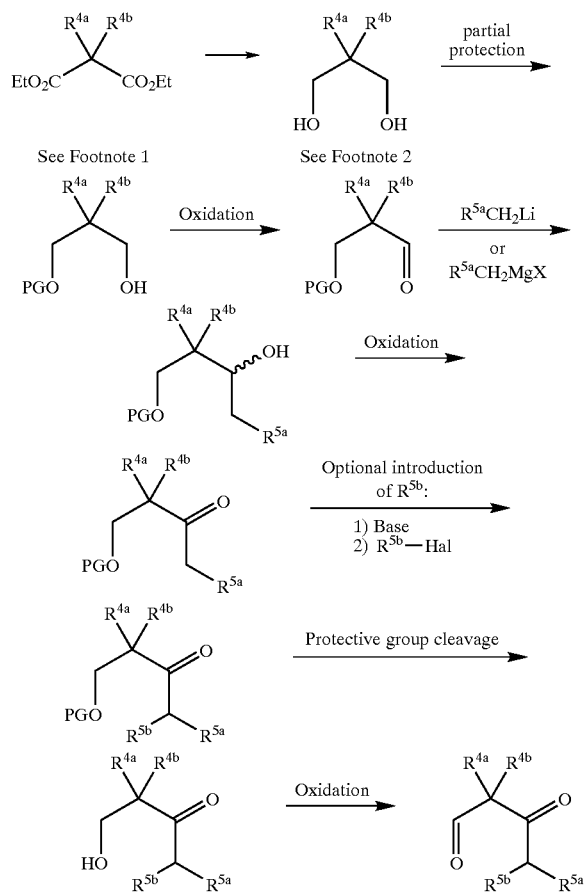

X = halogen, PG = protective group
1) See attached starting product C, in which $R^{4a} + R^{4b}$ = trimethylene
2) These 1,3-propanediols are in some cases commercially available and can then be used at this point in the synthesis.

Reaction scheme β:

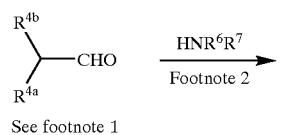

See footnote 1

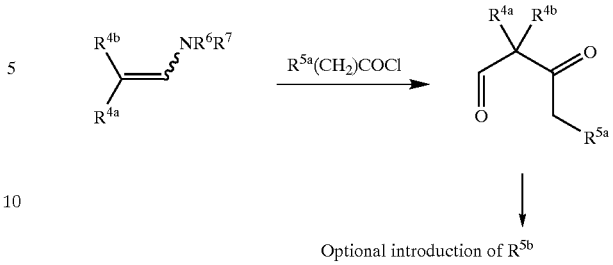

1) These sarting com[ounds are commercially available or can be obtained according to the methods that are known to one skilled in the art.
2) Secondary amine: preferably piperidine or morpholine or $R^6$ and $R^7$ mean, independently of one another, a straight-chain or branched $C_1$–$C_6$ alkyl group.

The components of general formula I that are produced according to this invention can be used in a way similar to the methods for synthesis of epothilone A and B that have been described and are known from, e.g., page 2 of this application text, as well as for the synthesis of epothilone derivatives that are modified accordingly in the $C_1$–$C_6$ section of the epothilone skeleton (Schinzer et al.: Chem. Eur. J. 1996, 2, No. 11, 1477–1482; Angew. Chem. 1997, 109, No. 5, pp. 543–544, Nicolaou et al.: Angew. Chem. 1997, 109, No. 1/2, pp. 170–172; Nature, Vol. 387, 1997, pp. 268–272; J. Am. Chem. Soc., Vol. 119, No. 34, 1997, pp. 7960–7973; J. Am. Chem. Soc., Vol. 119, No. 34, 1997, pp. 7974–7991, Angew. Chem. 1997, 109, No. 19, pp. 2181–2187).

With the compounds of general formula A", the substituent variability that is required up front is thus achieved.

A more significant advantage of the process according to the invention also lies in the fact that the chiral auxiliary group (4R,5S)- or (4S,5R)-4-methyl-5-phenyl-2-oxazolidione that is used can be recovered simply after being cleaved off from the protected compound of general formula IV and can be used again without loss of optical induction in the synthesis.

The components that are obtained in these methods, also their enantiomers or mixtures of these enantiomers, are suitable for aldocondensation with an epothilone component, which has a carbonyl function at C-7 (epothilone numbering system), as is the case in the above-mentioned total syntheses of epothilone A and epothilone B.

Components A, their enantiomers or mixtures of these enantiomers are suitable, moreover, for esterification with an epothilone component, which has a hydroxyl function at C-15 (epothilone numbering system), as is the case in the above-mentioned total syntheses of epothilone A and B.

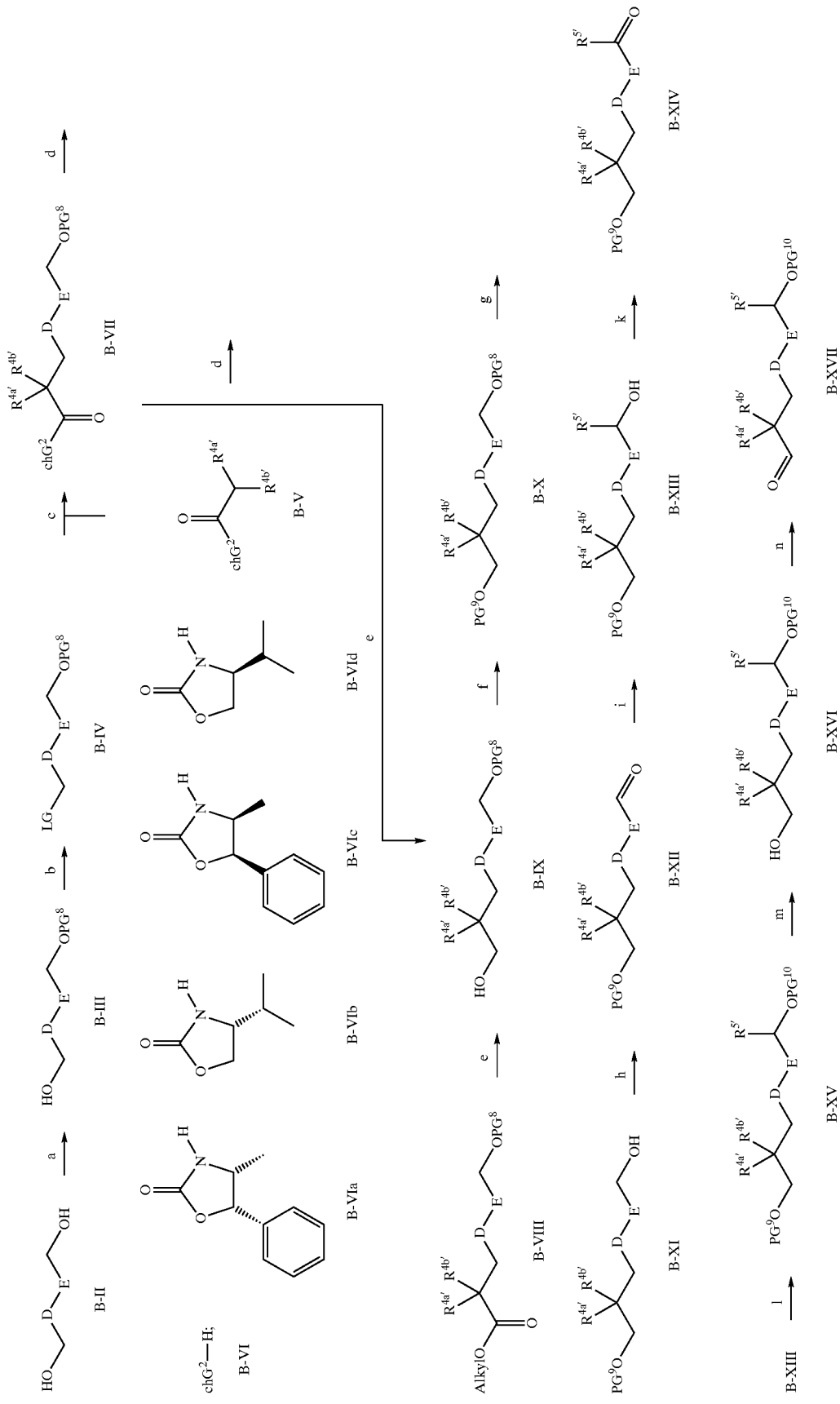

Step a (B-II ### B-III):

A hydroxyl group in B-II is protected according to the methods that are known to one skilled in the art. As protective group $PG^8$, the protective groups that are known to one skilled in the art, as were already mentioned above for $PG^4$ in step a (A-II ### A-III), are suitable.

Preferred are silicon-containing protective groups, which can be cleaved under acid reaction conditions or use of fluoride, such as, e.g., the trimethylsilyl, triethylsilyl, tert-butyldimethylsilyl, tert-butyldiphenylsilyl, tribenzylsilyl and triisopropylsilyl radicals.

Especially preferred is the tert-butyldimethylsilyl radical.

Step b (B-III ### B-IV):

The free hydroxyl group in B-III is converted into a leaving group LG according to the methods that are known to one skilled in the art. As leaving group LG, for example, halogens such as, e.g., bromine or iodine or alkyl- or aryl sulfonates, which are produced from the corresponding sulfonic acid halides or sulfonic acid anhydrides according to the methods that are known to one skilled in the art, are suitable.

As leaving group LG, the trifluoromethanesulfonate is preferred.

Step c (B-IV ### B-VII):

Compound B-IV is alkylated with the enolate of a carbonyl compound of general formula B-V, in which $chG^2$ can be a single alkoxy-group or else a chiral auxiliary group according to the methods that are known to one skilled in the art. The enolate is produced by action of strong bases, such as, e.g., lithium diisopropylamide, lithium hexamethyldisilazane at low temperatures. As chiral auxiliary group $chG^2$-H (B-VI), chiral alcohols that can be produced in an optically pure and inexpensive manner, such as, e.g., pulegol, 2-phenylcyclohexanol, 2-hydroxy-1,2,2-triphenylethanol, 8-phenylmenthol or compounds that contain reactive NH-groups that can be produced in an optically pure and inexpensive manner, such as, e.g., amines, amino acids, lactams or oxazolidinones, are suitable. Preferred are oxazolidinones; especially preferred are the compounds of formulas B-VIa to B-VId. The absolute stereochemistry on the α-carbonylcarbon of the compound of general formula B-VII is set by the selection of the respective antipode. In this way, the compounds of general formulas B-VII to B-XVII or their respective enantiomers ent-B-VII to ent-B-XVII can be obtained in an enantiomer-pure manner. If an achiral alcohol, such as, e.g., ethanol, is used as $chG^2$-H (B-VI), the racemic compounds rac-B-VII to rac-B-XVII are obtained.

Step d (B-VII ### B-VIII):

If group $chG^2$ represents one of the chiral auxiliary groups that are mentioned under step c, the latter is recovered by reesterification of B-VII in an alkyl ester of general formula B-VIII. The reesterification is carried out according to the methods that are known to one skilled in the art. Preferred is reesterification with simple alcohols, such as, e.g., methanol or ethanol in the presence of corresponding titanium(IV) alcoholates.

Step e (B-VIII ### B-IX):

The ester in B-VIII is reduced to alcohol B-IX. As reducing agents, the reducing agents that are known to one skilled in the art, such as, e.g., aluminum hydrides, such as, e.g., lithium aluminum hydride or diisobutylaluminum hydride, are suitable. The reaction is carried out in an inert solvent, such as, e.g., diethyl ether, tetrahydrofuran, toluene.

Step e' (B-VII ### B-IX):

As an alternative to Q steps d) and e), the carbonyl group in B-VII can be reduced immediately to the alcohols of general formula B-IX according to the conditions that are mentioned under step e). Here, chiral auxiliary component $chG^2$-H can also be recovered.

Step f (B-IX ### B-X):

The free hydroxyl group in B-IX is protected according to the methods that are known to one skilled in the art. As protective group $PG^9$, the protective groups that are known to one skilled in the art, as were already mentioned above for $PG^4$ in step a (A-II ### A-III), are suitable.

Preferred are those protective groups that can be cleaved under acidic reaction conditions, such as, e.g., the methoxymethyl, tetrahydropyranyl, tetrahydrofuranyl, and trimethylsilyl radical.

Especially preferred is the tetrahydropyranyl radical.

Step g (B-X ### B-XI):

Protective group $PG^8$, which is introduced under step a), is now cleaved according to the processes that are known to one skilled in the art. If this is a silyl ether, then the reaction with fluorides, such as, for example, tetrabutylammonium fluoride, the hydrogen fluoride-pyridine complex, potassium fluoride or the use of dilute mineral acids, the use of catalytic amounts of acids, such as, e.g., para-toluenesulfonic acid, paratoluenesulfonic acid-pyridinium salt, camphorsulfonic acid in alcoholic solutions, preferably in ethanol or isopropanol, is suitable for the cleavage.

Step h (B-XI ### B-XII):

The oxidation of the primary alcohol in B-XI to the aldehyde of general formula B-XII is carried out according to the processes that are known to one skilled in the art. For example, the oxidation with pyridinium chlorochromate, pyridinium dichromate, chromium trioxide-pyridine complex, the oxidation according to Swern or related methods, e.g., with use of oxalyl chloride in dimethyl sulfoxide, the use of Dess-Martin periodinane, the use of nitrogen oxides, such as, e.g., N-methylmorpholino-N-oxide in the presence of suitable catalysts, such as, e.g., tetrapropylammonium perruthenate in inert solvents, can be mentioned. Preferred is the oxidation according to Swern, as well as with N-methylmorpholino-N-oxide with use of tetrapropylammonium perruthenate.

Step i (B-XII ### B-XIII):

The reaction of aldehyde B-XII to form alcohols of general formula B-XIII is carried out according to the methods that are known to one skilled in the art with organometallic compounds of general formula M-$R^{5'}$, in which M stands for an alkali metal, preferably lithium or a divalent metal MX, in which X represents a halogen and radical $R^{5'}$ has the above-mentioned meaning. As a divalent metal, magnesium and zinc are preferred; as a halogen, X is preferably chlorine, bromine and iodine.

Step k (B-XIII ### B-XIV):

The oxidation of alcohol B-XIII to the ketone of general formula B-XIV is carried out according to the processes that are mentioned under h). Preferred is the oxidation with N-methylmorpholino-N-oxide with use of tetrapropylammonium perruthenate.

Step l (B-XIII ### B-XV):

The hydroxyl group in B-XIII can be provided according to the processes that are mentioned under a) with a protective group $PG^{10}$. Preferred are silicon-containing protective groups, which can be cleaved under acidic reaction conditions or with use of fluoride, such as, e.g., the trimethylsilyl, triethylsilyl, tert-butyldimethylsilyl, tert-butyldiphenylsilyl, tribenzylsilyl, and triisopropylsilyl radicals.

Especially preferred is the tert-butyldiphenylsilyl radical.

Step m (B-XV ### B-XVI):

Protective group $PG^9$, which is introduced under step f), is cleaved according to the processes that are described under step g).

Step n (B-XVI ### B-XVII):

The oxidation of alcohol B-XVI to the aldehyde of general formula B-XVII is carried out according to the processes that are mentioned under h). Preferred is the oxidation according to Swern.

As an alternative, the compounds of general formula B-XIII can be produced with the method that is described in Reaction scheme 5.

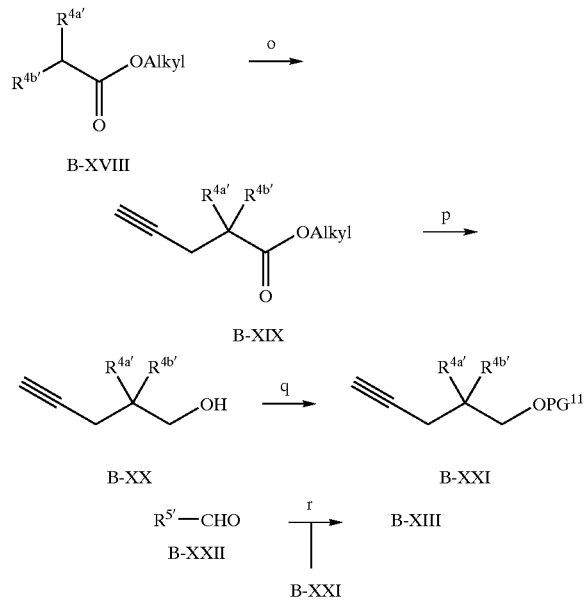

Step o (B-XVIII ### B-XIX):

Starting from ethyl acetate derivatives, which can be obtained inexpensively, of general formula B-XVIII, in which $R^{4a'}$, and $R^{4b'}$ have the above-mentioned meanings, the ester enolate is produced by action of strong bases, such as, e.g., lithium diisopropylamide, and lithium hexamethyldisilazane, at low temperatures and reacted with 3-halogen-1-propine, preferably 3-bromo-1-propine, to form compounds of general formula B-XIX.

Step p (B-XIX ### B-XX):

The reduction of ester B-XIX to alcohol B-XX is carried out according to the methods that are described under step e), preferably with use of diisobutylaluminum hydride.

Step q (B-XX ### B-XXI):

The hydroxyl group in B-XX can be provided according to the conditions that are mentioned under a) with a protective group $PG^{11}$. Preferred are silicon-containing protective groups, which can be cleaved under acidic reaction conditions or use of fluoride, such as, e.g., the trimethylsilyl, triethylsilyl, tert-butyldimethylsilyl, tert-butyldiphenylsilyl, tribenzylsilyl- or triisopropylsilyl radical.

Especially preferred is the tert-butyldimethylsilyl radical.

Step r (B-XXI ### B-XIII):

Acetylene B-XXI can be deprotonated according to the processes that are known to one skilled in the art, and the acetylide that is obtained can be reacted with carbonyl compounds of general formula B-XXII, in which $R^{5'}$ has the above-mentioned meaning, to form an alcohol of general formula XIII. For deprotonation, alkyl alkali compounds, such as, e.g., butyllithium or other strong bases, such as, e.g., alkali hexamethyldisilazanes or lithium diisopropylamide, are suitable. Preferred is n-butyllithium.

In the process that is described in Reaction scheme 5, first racemic compounds rac-B-XIII are obtained. Optionally, steps rac-B-XIX or rac-B-XX that are passed through according to Reaction scheme 6 offer the possibility for chemical racemate cleavage and thus also access to enantiomer-pure compounds B-XX or ent-B-XX, if $R^{4a'}$, is not identical to $R^{4b'}$.

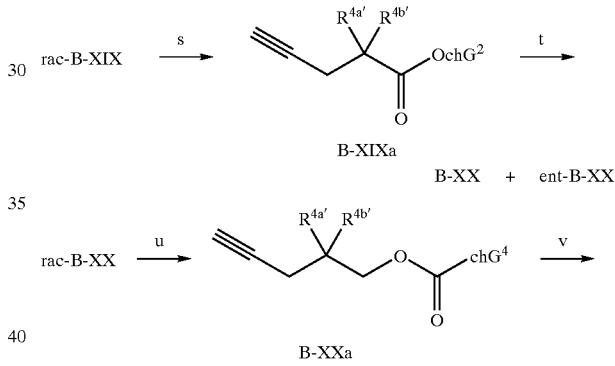

Step s (rac-B-XIX ### B-XIXa):

Racemic compound rac-B-XIX can be reesterified with a chiral alcohol $chG^3$-OH that can be obtained in an optically pure manner according to the methods that are known to one skilled in the art, for example the process that is mentioned under step d), to form a mixture of diastereomeric ester B-XIXa and separated with simple chromatographic methods. As chiral alcohols, for example, pulegol, 2-phenylcyclohexanol, 2-hydroxy-1,2,2-triphenylethanol, and 8-phenylmenthol are suitable.

Step t (B-XIXa ### B-XX and ent-B-XX):

Diastereomer-pure esters B-XIXa can be reduced in each case to alcohols B-XX or ent-B-XX according to the process that is described under step e, whereby auxiliary component $chG^3$-OH that is described under step s can be recovered.

Step u (rac-B-XX ### B-XXa):

Racemic compound-rac-B-XX can be reacted with a chiral acid $chG^4$—$CO_2H$ that can be obtained in an optically pure manner, its esters, anhydride or acid halide, according to the methods that are known to one skilled in the art, to form a mixture of the diastereomeric ester XXa and separated with simple chromatographic methods. As chiral acids, for example, malic acid, tartaric acid or their derivatives are suitable.

Step v (B-XXa ### B-XX and ent-B-XX):

Diastereomer-pure esters B-XXa can be reduced in each case to alcohols B-XX or ent-B-XX according to the process that is described under step e, or saponified according to the methods that are known to one skilled in the art, whereby in the last-mentioned case, auxiliary component chG⁴—CO₂H that is described under step u can be recovered.

Representation of Partial Fragments C:

It is known that the compound of formula

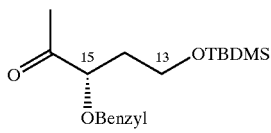

(TBDMS stands for a tert-butyldimethylsilyl radical) can be used for synthesis of the C13–C16 fragment (epothilone numbering system) of epothilone A (Schinzer et al. Chem. Eur. J. 1996, 2, No. 11, 1477–1482). The synthesis that is described by Schinzer et al. introduces the required chirality via a kinetic racemate cleavage according to Sharpless. A necessary chromatographic separation, an inadequate enantiomer excess (80%) and a low overall yield disqualify this approach for an industrial synthesis, which requires high yields and high optical purity of the synthesis products.

It is further known that the above-mentioned synthesis component can be converted by Wittig reaction with the phosphonate of formula

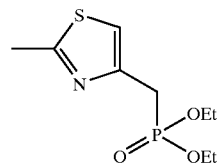

into a compound of formula

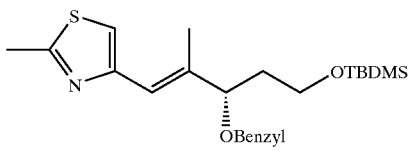

which then can be used for the introduction of the C13–C20 fragment for the epothilone synthesis.

Partial fragments of formula C can be produced in an efficient way with high optical-purity (>99.5%) from inexpensive malic acid that can be obtained at a reasonable price.

The synthesis is described in Reaction scheme 7 below in the example of the L-(−)-malic acid (C-I). Starting from D(+)-malic acid (ent-C-I), the corresponding enantiomeric compounds (ent-C-II to ent-C-XI) are obtained, and starting from racemic malic acid (rac-C-I), the corresponding racemic compounds (rac-C-II to rac-C-XI) are obtained.

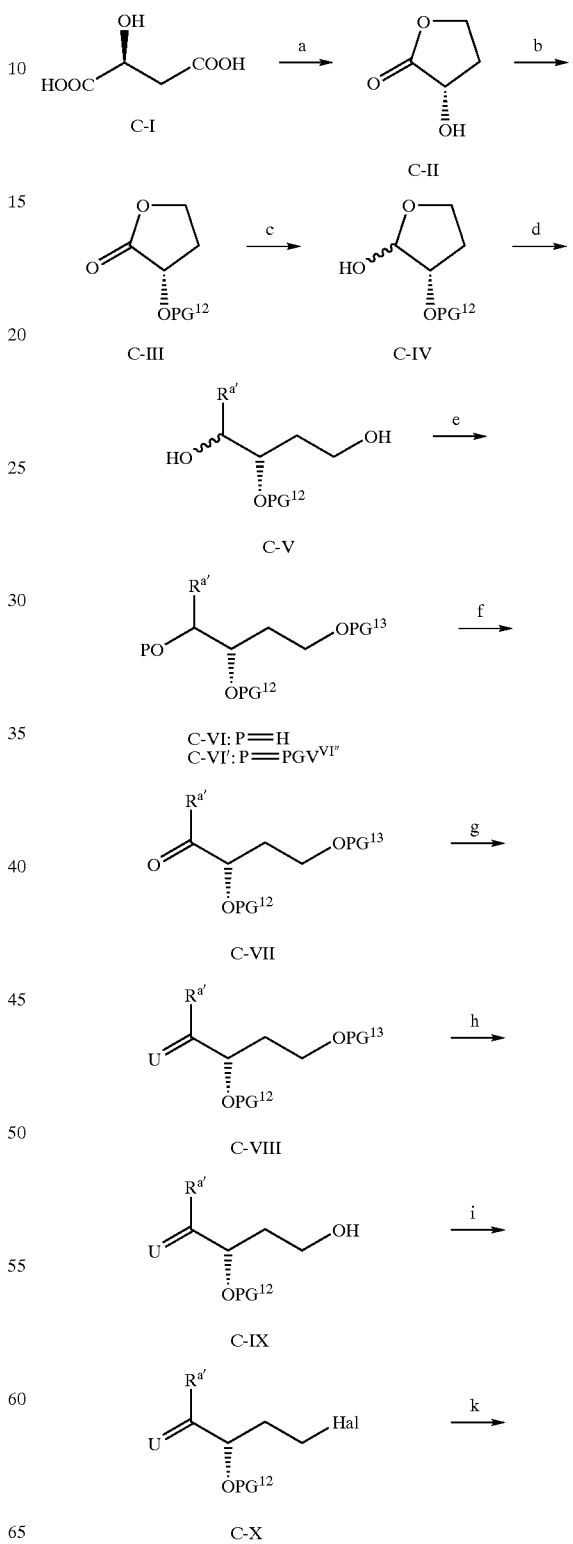

Reaction scheme 7

-continued

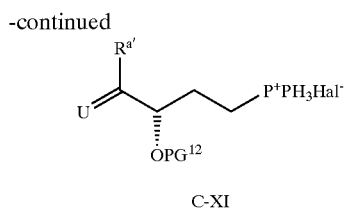

C-XI

Step a (Malic acid C-1C-II):

L-(−)-Malic acid is converted into hydroxylactone C-II according to a process that is known in the literature (Liebigs Ann. Chem. 1993, 1273–1278).

Step b (C-II ### C-III):

The free hydroxy group in compound C-II is protected according to the methods that are known to one skilled in the art. As protective group $PG^{12}$ the protective groups that are known to one skilled in the art, as were already mentioned above for $PG^4$ in section a (A-II ### A-III), are suitable.

Preferred are those protective groups that can be cleaved under the action of fluoride, but are stable under weakly acidic reaction conditions, such as, e.g., the tert-butyldiphenylsilyl, tert-butyldimethylsilyl or triisopropylsilyl radical.

Especially preferred are the tert-butyldiphenylsilyl radical and the tert-butyldimethylsilyl radical.

Step c (C-III ### C-IV):

Lactone C-III is reduced to lactol C-IV according to the methods that are known to one skilled in the art. Aluminum hydrides that are modified in their reactivity, such as, e.g., diisobutylaluminum hydride, are suitable as reducing agents. The reaction is carried out in an inert solvent, such as, e.g., toluene, preferably at low temperatures (−20 to −100° C.).

Step d (C-IV ### C-V):

The reaction of lactol C-IV to form compounds of formula C-V is carried out with organometallic compounds of general formula M-$R^8$, in which M stands for an alkali metal, preferably lithium, or a divalent metal MX, in which X represents a halogen, and $R^{8'}$ has the above-mentioned meanings. As a divalent metal, magnesium and zinc are preferred; as halogen, X is preferably chlorine, bromine or iodine.

Step e (C-V ### C-VI):

The primary hydroxyl group in compound C-V is protected selectively relative to the secondary hydroxyl group according to the methods that are known to one skilled in the art.

The secondary hydroxy group is optionally then also protected according to known methods that are familiar to one skilled in the art.

As protective groups $PG^{13}$ and $PG^{VI''}$, the protective groups that are known to one skilled in the art, as were already mentioned above for $PG^4$ in step a (A-II ### A-III), are suitable.

Preferred are those protective groups that can be cleaved under weakly acidic reaction conditions selectively in the presence of protective group PG10, which is introduced from component A in the synthesis of the compound of general formula I, such as, e.g., the trimethylsilyl radical, triethylsilyl radical or tert-butyldimethylsilyl radical.

Especially preferred is the tert-butyldimethylsilyl radical.

Step f (C-VI ### C-VII):

The oxidation of the secondary alcohol in C-VI to form ketone C-VII is carried out according to the methods that are known to one skilled in the art. For example, the oxidation with pyridinium chlorochromate, pyridinium dichromate, chromium trioxide-pyridine complex, the oxidation according to Swern or related methods, e.g., with use of oxalyl chloride in dimethyl sulfoxide, the use of Dess-Martin periodinane, the use of nitrogen oxides, such as, e.g., N-methyl-morpholino-N-oxide in the presence of suitable catalysts, such as, e.g., tetrapropylammonium perruthenate in inert solvents, can be mentioned. Preferred is the oxidation according to Swern.

Step g (C-VII ### C-VIII):

For compounds in which U is equal to CR10'R11', this grouping is established according to the processes that are known to one skilled in the art. For this purpose, methods, such as, e.g., the Wittig reaction or Wittig/Horner reaction, the addition of an organometallic compound MCHR10'R11' while being cleaved with water, are suitable. Preferred is the Wittig reaction and Wittig/Horner reaction with use of phosphonium halides of CR10'R11'P(Ph)$3^+$Hal$^-$ type or phosphonates of CR10'R11'P(O) (Oalkyl)2 type with Ph equal to phenyl, R10', R11' and halogen in the already mentioned meanings with strong bases, such as, e.g., n-butyllithium, potassium-tert-butanolate, sodium ethanolate, and sodium-hexamethyl disilazane; n-butyllithium is preferred as a base.

For compounds in which U represents two alkoxy groups $OR^{23}$ or a $C_2$–$C_{10}$ alkylene-α, ω-dioxy group, the ketone is ketalized according to the methods that are known to one skilled in the art, for example with use of an alcohol $HOR^{23}$ or a $C_2$–$C_{10}$ alkylene-α, ω-diol under acid catalysis.

Step h (C-VIII ### C-IX):

Protective group $PG^{13}$ that is introduced under e is now cleaved selectively in the presence of $PG^{12}$ according to the processes that are known to one skilled in the art. If this is an acidic cleavable protective group, then the cleavage preferably takes place under weakly acidic conditions, such as, e.g., by reaction with dilute organic acids in inert solvents. Acetic acid is preferred.

Step i (C-IX ### C-X):

The free primary hydroxyl group is optionally converted into a halide according to the processes that are known to one skilled in the art. Preferred halides are chlorine, but especially bromine and iodine. The substitution of the hydroxyl group for a bromine can be carried out, e.g., by means of triphenylphosphine/tetrabromomethane but also according to any other process that is known to one skilled in the art. The establishment of an iodine atom can be carried out from the bromide by substitution, e.g., according to Finkelstein with sodium iodide in acetone. The direct conversion of the hydroxyl group into iodide is also possible, e.g., with use of elementary iodine, imidazole and triphenylphosphine in dichloromethane.

If U ultimately stands for H/$OR^9$ with $R^9$ in the meaning of a hydrogen atom, the conversion of the primary hydroxy group into a halogen atom in the stage of the compound C-VI' is performed after selective protection removal of the primary hydroxy group.

Step k (C—X ### C-XI):

If the linkage of the C13–C16 unit is to be carried out with the 12-position of the epothilone radical or epothilone fragments, e.g., a $C_7$–$C_{12}$ unit by Wittig reaction, as described in, e.g., Nature Vol. 387, 268–272 (1997), the triphenyl-phosphonium halides ($R^{21}=P(Ph)_3{}^+Hal^-$), alkyl or arylphosphonates ($R^{21}=P(O)(OQ)_2$) or phosphine oxides ($R^{21}=P(O)Ph_2$) of type C-XI are produced starting from the halides C-X according to the processes that are known to one skilled in the art. In this case, Ph means phenyl; Hal stands for F, Cl, Br or I, and Q is a $C_1$–$C_{10}$ alkyl radical or phenyl radical.

For production of the phosphonium salts, e.g., the reaction of the corresponding halides with triphenylphosphine in solvents such as toluene or benzene is suitable.

The production of the phosphonates can be carried out by, e.g., reaction of halides C-X with a metallated dialkyl phosphite. The metallation is usually carried out with strong bases, such as, e.g., butyllithium.

The production of the phosphine oxides can be carried out by, e.g., reaction of halides C-X with metallated diphenylphosphine and subsequent oxidation. For the metallation, strong bases such as butyllithium are also suitable. The subsequent oxidation to phosphine oxide can then be carried out with, e.g., dilute aqueous hydrogen peroxide solution.

It has been found that compounds of formula C" can be produced, surprisingly enough, in an efficient way with high optical purity (>99.5%) from inexpensive enantiomer-pure malic acid that can be obtained at a reasonable price, although in principle in the described process according to the invention, the possibility for complete or partial racemization would exist.

As mentioned above, the known process yields those compounds in which $R^1$ is a methyl group, $R^2$ is a tert-butyldimethylsilyl radical or benzyl radical, $R^3$ is an O-tert-butyl dimethyl silyl radical, and X is an oxygen-atom or a (2-methylthiazol-4-yl)methylene radical, only in an optical purity of about 80%.

In addition, the chemical yields of the process according to the invention are significantly higher than the yields that are indicated in the processes described by Schinzer et al. For example, the yield of (3S)-5-[(dimethyl(1,1-dimethylethyl)-silyl]oxy]-3-[[1,1-dimethylethyl)diphenylsilyl]oxy]-2-pentanone, produced according to the process according to the invention, starting from L-(−)-malic acid with 26.5% is almost twice as high as the yield that is achieved by Schinzer et al. in the production of (3S)-3-benzyloxy-5-[[dimethyl(1,1-dimethylethyl)silyl]oxy]-2-pentanone (14.35%; Chem. Eur. J. 1996, 2, No. 11, 1477–1482) or the yield that is achieved in the production of (3S)-3-[([dimethyl(1,1-dimethylethyl)silyl]oxy]-5-[[dimethyl(1,1-dimethylethyl)silyl]oxy]-2-pentanone (20.58%; Angew. Chem. 1997, 109, No. 5, 543–544).

This comparison is based on the yields that are indicated in the above-mentioned bibliographic references, whereby—as already mentioned above—it is to be taken into consideration that the compounds that are obtained according to the known processes do not accumulate in an enantiomer-pure manner, so that the actual yield of the enantiomer-pure compounds in question is lower, and an additional purification step in this or a later process stage is necessary for obtaining an enantiomer-pure compound.

The process according to the invention, moreover, makes possible a very wide variation of the substituents in this C13–C16 component.

This invention thus relates to a process for the production of the compounds of general formula C', which is characterized in that L-(−)-malic acid, D(+)-malic acid or racemic malic acid is used as a starting product.

Optically pure D-(+)- or L-(−)-malic acid is preferably used.

The invention also relates to the intermediate compounds, occurring in the process, of general formulas V, VI and VI' (combined below as VI") i

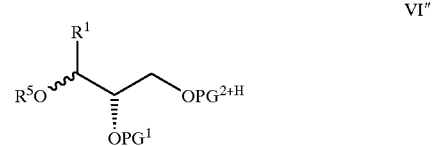

in which
$R^1$, $PG^1$ and $R^5$ have the meaning that is indicated in general formula C', and
$PG^{2+H}$ stands for a hydrogen atom or a protective group $PG^2$.

These compounds are produced according to the invention in that an organometallic compound of general formula $R^1Y$ in which $R^1$ has the meaning that is indicated in general formula C', and
Y stands for an alkali metal atom or MZ, whereby M is a divalent metal atom and Z is a halogen atom.

is added to a compound of general formula IV

IV (structure: tetrahydrofuran ring with HO and $PG^1$ substituents)

in which $PG^1$ has the meaning that is indicated in general formula C, while a lactol ring is opened up.

Lithium is preferred as an alkali atom.

In the case of MZ, magnesium and zinc are preferred for the divalent metal atom; as a halogen atom, primarily chlorine, bromine and iodine are considered.

In addition, this invention relates to the new C13–C16 epothilone components of general formula C

C (structure showing $R^1$, X, $OR^2$, $R^3$ with positions 15 and 13)

in which
$R^1$ means hydrogen, $C_1$–$C_{20}$ alkyl, aryl, $C_7$–$C_{20}$ aralkyl, which can all be substituted,
$R^2$ means hydrogen or a protective group $PG^1$,
$R^3$ means a hydroxy group; halogen, a protected hydroxy group $OPG^2$, a phosphonium halide radical $PPh_3{}^+Hal^-$ (Ph=phenyl; Hal=F, Cl, Br, I), a phosphonate radical $P(O)(OQ)_2$ (Q=$C_1$–$C_{10}$ alkyl or phenyl) or a phosphine oxide radical $P(O)Ph_2$ (Ph=phenyl),
X means an oxygen atom, two alkoxy groups $OR^4$, a $C_2$–$C_{10}$ alkylene-α, ω-dioxy group, which can be straight-chain or branched, H/$OR^5$ or a grouping $CR^6R^7$, whereby
$R^4$ stands for a $C_1$–$C_{20}$ alkyl radical,
$R^5$ stands for hydrogen or a protective group $PG^3$,
$R^6$, R7 are the same or different and stand for hydrogen, a $C_1$–$C_{20}$ alkyl, aryl, $C_7$–$C_{20}$ aralkyl radical or $R^6$ and $R^7$ together with the methylene carbon atom together stand for a 5- to 7-membered carbocyclic ring, whereby not at the same time
$R^1$ can be a methyl group, $R^2$ can be a tert-butyldimethylsilyl radical or benzyl radical, $R^3$ can be an O-tert-butyldimethylsilyl radical and X can be a (2-methylthiazol-4-yl)methylene radical or
$R^1$ can be a methyl group, $R^2$ can be a tert-butyldimethylsilyl radical, $R^3$ can be a triphenylphosphonium iodide radical, and X can be a (2-methylthiazol-4-yl) methylene radical.

The compounds that were already produced by Schinzer et al. according to a process other than that according to the invention (Chem. Eur. J. 1996, 2, No. 11, 1477–1482 and Angew. Chem. 1997, 109, No. 5, 543–544) are excluded by the first disclaimer.

The second disclaimer takes into consideration the (5E,3S -[3-[[(1,1-dimethylethyl)dimethylsilyl]oxy]-4-methyl-5-(2-methylthiazol-4-yl)-pent-4-en-1-yl]-triphenylphosphonium iodide mentioned by K. C. Nicolaou et al. in Nature, Vol. 387, 1997, 268–272.

For the more detailed explanation of substituents $R^1$, $R^4$, $R^6$, $R^7$, $PG^1$, $PG^2$ and $PG^3$ occurring in the compounds of general formula C, the statements made above for the substituents of general formula C' hold true.

According to the invention, those compounds of general formula C are preferred in which
$R^1$ stands for a hydrogen atom, an optionally substituted $C_1$–$C_4$ alkyl radical, a phenyl radical optionally substituted with 1 to 3 radicals, selected from the group of substituents halogen, free hydroxy group or protected hydroxy group $OPG^4$, $C_1$–$C_4$ alkyl, azido, nitro, nitrile and amino ($NH_2$), and/or
X stands for an oxygen atom, and/or
the aryl radical that stands for $R^6$ and/or $R^7$ stands for a phenyl radical optionally substituted with 1 to 3 radicals, selected from the group of substituents halogen, free hydroxy group or protected hydroxy group $OPG^5$; $CO_2H$, $CO_2$-alkyl, $C_1$–$C_4$ alkyl, azido, nitro, nitrile, amino ($NH_2$) or for a 5- or 6-membered heteroaryl radical optionally substituted with 1 to 2 $C_1$–$C_4$ alkyl radicals,
in particular for a substituent that is selected from the group 2-, 3-furanyl, 2-, 3-, 4-pyridinyl, 2-, 4-, 5-thiazolyl-, 2-, 4- and 5-imidazolyl radical, which optionally is substituted by 1 or 2 $C_1$–$C_4$ alkyl radicals, and/or
$PG^1$, $PG^2$ and $PG^3$ are selected from the group of substituents methoxymethyl, methoxyethyl, ethoxyethyl, tetrahydropyranyl, tetrahydrofuranyl, trimethylsilyl, triethylsilyl, tert-butyldimethylsilyl, tertbutyldiphenylsilyl, tribenzylsilyl, triisopropylsilyl, benzyl, para-nitrobenzyl, para-methoxybenzyl, acetyl, propionyl, butyryl and benzoyl radical,
in particular $PG^1$ is a tert-butyldiphenylsilyl radical, tert-butyldimethylsilyl radical or triisopropylsilyl radical and
in particular $PG^2$ is a tert-butyldimethylsilyl radical, acetyl radical, benzoyl radical, benzyl radical or tetrahydropyranyl radical.
As protective groups $PG^4$ and $PG^5$, all protective groups that are indicated above for $PG^1$, $PG^2$ and $PG^3$ are suitable.

Representation of Partial Fragments ABC and Their Cyclization to I:

In this respect, the processes that are also described in DE 197 51 200.3 and PCT/EP98/05064 are suitable.

Partial fragments of general formula AB

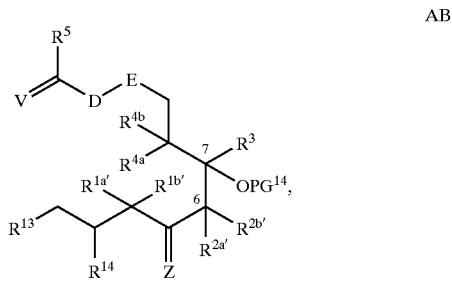

in which $R^{1a'}$, $R^{1b'}$, $R^{2a'}$, $R^{2b'}$, $R^3$, $R^{4a}$, $R^{4b}$, $R^5$, $R^{13}$, $R^{14}$, D, E, V and Z have the meanings already mentioned, and $PG^{14}$ represents a hydrogen atom or a protective group PG, are obtained from the previously described fragments A and 1B according to the process that is shown in Reaction scheme 8.

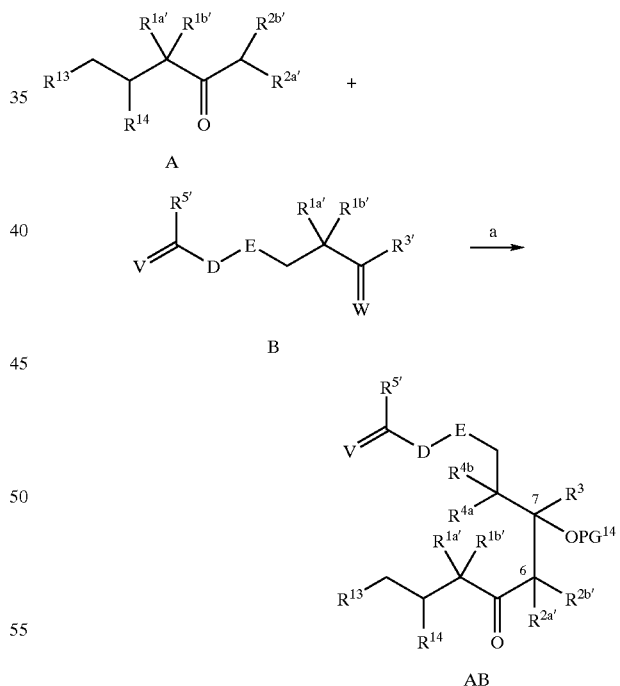

Step a (A+B ### AB):

Compound B, in which W has the meaning of an oxygen atom and optionally present additional carbonyl groups are protected, is alkylated with the enolate of a carbonyl compound of general formula A. The enolate is produced by action of strong bases, such as, e.g., lithium diisopropylamide, lithium hexamethyldisilazane at low temperatures.

Partial fragments of general formula ABC

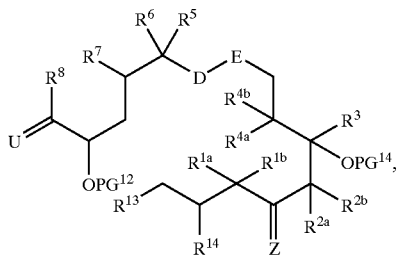

in which $R^{1a\prime}$, $R^{1b\prime}$, $R^{2a\prime}$, $R^{2b\prime}$, $R^3$, $R^{4a}$, $R^{4b}$, $R^5$, $R^6$, $R^7$, $R^8$, $R^{13}$, $R^{14}$, D, E, U and Z have the already mentioned meanings, are obtained from previously described fragments AB and C according to the process that is shown in Reaction scheme 9.

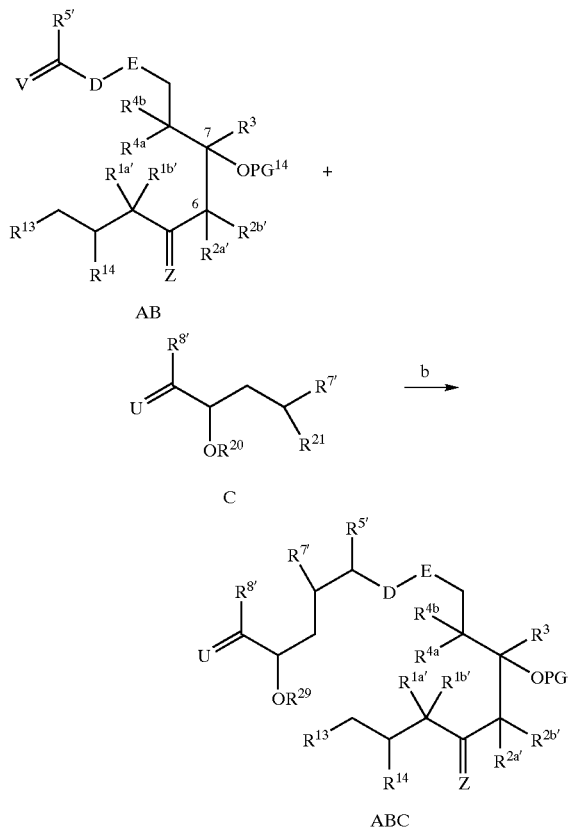

Step b (AB+C ### ABC):

Compound C, in which $R^{21}$ has the meaning of a Wittig salt, and optionally present additional carbonyl groups are protected, is deprotonated by a suitable base, such as, e.g., n-butyllithium, lithium diisopropylamide, potassium tert-butanolate, sodium or lithium-hexamethyldisilazide and reacted with a compound AB, in which V has the meaning of an oxygen atom.

Step c (ABC ### 1):

Compounds ABC, in which $R^{13}$ represents a carboxylic acid $CO_2H$ and $R^{20}$ represents a hydrogen atom, are reacted according to the methods that are known to one skilled in the art for the formation of large macrolides to form compounds of formula I, in which Y has the meaning of an oxygen atom. Preferred is the method that is described in "Reagents for organic Synthesis, Vol. 16, p. 353" with use of 2,4,6-trichlorobenzoic acid chloride and suitable bases, such as, e.g., triethylamine, 4-dimethylaminopyridine, and sodium hydride.

Step d (ABC ### 1):

Compounds ABC, in which $R^{13}$ represents a group $CH_2OH$ and $R^{20}$ represents a hydrogen atom, can be reacted preferably with use of triphenylphosphine and azodiesters, such as, for example, azodicarboxylic acid diethyl ester, to form compounds of formula I, in which Y has the meaning of two hydrogen atoms.

Compounds ABC, in which $R^{13}$ represents a group $CH_2OSO_2$ alkyl or $CH_2OSO_2$ aryl or $CH_2OSO_2$ aralkyl and $R^{20\prime}$ represents a hydrogen atom, can be cyclized to compounds of formula I, in which Y has the meaning of two hydrogen atoms, after deprotonation with suitable bases, such as, for example, sodium hydride, n-butyllithium, 4-dimethylaminopyridine, Hünig base, and alkylhexamethyldisilazanes.

The flexible functionalization of described components A, B, and C also ensures a linkage sequence that deviates from the above-described process and that leads to components ABC. These processes are listed in the following table:

| Possible Linkages | Linkage Methods a to e | Prerequisites |
|---|---|---|
| A + B ### A – B | Aldol (see Reaction scheme 8) | Z = W = oxygen |
| B + C ### B – C | b: Wittig (analogously to Reaction scheme 9) e: McMurry | U = oxygen and $R^{21}$ = Wittig salt or phosphine oxide or phosphonate U = V = oxygen |
| A + C ### A – C | c: Esterification (e.g., 2,4,6-trichlorobenzoyl chloride/4-dimethylamino-pyridine) d: etherification (e.g., Mitsunobu) | $R^{13} = CO_2R^{13b}$ or COHal and $R^{20}$ = hydrogen $R^{13} = CH_2OH$ and $R^{20}$ = hydrogen or $SO_2$-alkyl or $SO_2$-aryl or $SO_2$-aralkyl |

According to these processes, components A, B and C, as indicated in Reaction scheme 10, can be linked:

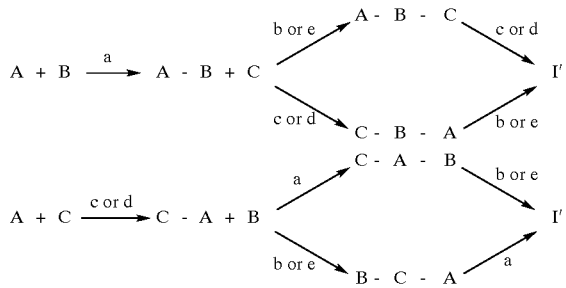

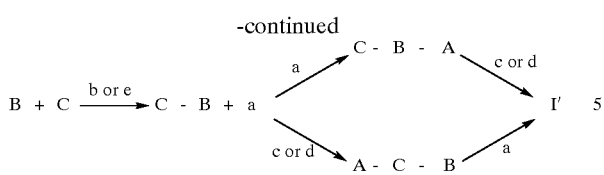

Free hydroxyl groups in I, A, B, C, AB, ABC can be further functionally modified by etherification or esterification, free carbonyl groups by ketalization, enol ether formation or reduction.

The invention relates to all stereoisomers of these compounds and also their mixtures.

Biological Actions and Applications of the New Derivatives:

The new compounds of formula I are valuable pharmaceutical agents. They interact with tubulin by stabilizing microtubuli that are formed and are thus able to influence the cell-splitting in a phase-specific manner. This relates mainly to quick-growing, neoplastic cells, whose growth is largely unaffected by intercellular regulating mechanisms. Active ingredients of this type are in principle suitable for treating malignant tumors. As applications, there can be mentioned, for example, the therapy of ovarian, stomach, colon, adeno-, breast, lung, head and neck carcinomas, malignant melanoma, acute lymphocytic and myelocytic leukemia. The compounds according to the invention are suitable owing to their properties basically for anti-angiogenesis therapy as well as for treatment of chronic inflammatory diseases, such as, for example, psoriasis or arthritis. To avoid uncontrolled proliferation of cells and for better compatibility of medical implants, they can basically be applied or introduced into the polymer materials that are used for this purpose. The compounds according to the invention can be used alone or to achieve additive or synergistic actions in combination with other principles and classes of substances that can be used in tumor therapy.

As examples, there can be mentioned the combination with

Platinum complexes, such as, e.g., cis-platinum, carboplatinum, intercalating substances, e.g., from the class of anthracyclines, such as, e.g., doxorubicin or from the class of anthrapyrazoles, such as, e.g., Cl-941, substances that interact with tubulin, e.g., from the class of vinca-alkaloids, such as, e.g., vincristine, vinblastine or from the class of taxanes, such as, e.g., taxol, taxotere or from the class of macrolides, such as, e.g., rhizoxin or other compounds, such as, e.g., colchicine, combretastatin A-4, DNA topoisomerase inhibitors, such as, e.g., camptothecin, etoposide, topotecan, teniposide, folate- or pyrimidine-antimetabolites, such as, e.g., lometrexol, gemcitubin, DNA-alkylating compounds, such as, e.g., adozelesin, dystamycin A, inhibitors of growth factors (e.g., of PDGF, EGF, TGFb, EGF), such as, e.g., somatostatin, suramin, bombesin antagonists, inhibitors of protein tyrosine kinases or protein kinases A or C, such as, e.g., erbstatin, genistein, staurosporine, ilmofosine, 8-Cl-cAMP, antihormones from the class of antigestagens, such as, e.g., mifepristone, onapristone or from the class of antiestrogens, such as, e.g., tamoxifen or from the class of antiandrogens, such as, e.g., cyproterone acetate, metastases-inhibiting compounds, e.g., from the class of eicosanoids, such as, e.g., $PGl_2$ $PGE_1$, 6-oxo-$PGE_1$ as well as their more stable derivatives (e.g., iloprost, cicaprost, misoprostol), inhibitors of oncogenic RAS proteins, which influence the mitotic signal transduction, such as, for example, inhibitors of the farnesyl-protein-transferase, natural or synthetically produced antibodies, which are directed against factors or their receptors, which promote tumor growth, such as, for example, the erbB2 antibody.

The invention also relates to pharmaceutical agents that are based on pharmaceutically compatible compounds, i.e., compounds of general formula I that are nontoxic in the doses used, optionally together with commonly used adjuvants and vehicles.

According to methods of galenicals that are known in the art, the compounds according to the invention can be processed into pharmaceutical preparations for enteral, percutaneous, parenteral or local administration. They can be administered in the form of tablets, coated tablets, gel capsules, granulates, suppositories, implants, injectable, sterile, aqueous or oily solutions, suspensions or emulsions, ointments, creams and gels.

In this case, the active ingredient or ingredients can be mixed with the adjuvants that are commonly used in galenicals, such as, e.g., gum arabic, talc, starch, mannitol, methyl cellulose, lactose, surfactants such as Tweens or Myrj, magnesium stearate, aqueous or non-aqueous vehicles, paraffin derivatives, cleaning agents, dispersing agents, emulsifiers, preservatives and flavoring substances for taste correction (e.g., ethereal oils).

The invention thus also relates to pharmaceutical compositions that as active ingredients contain at least one compound according to the invention. A dosage unit contains about 0.1–100 mg of active ingredient(s). In humans, the dosage of the compounds according to the invention is approximately 0.1–1000 mg per day.

The examples below are used for a more detailed explanation of the invention, without intending that it be limited to these examples.

In the assignment of numbers to the examples for the respective starting compounds and in the assignment of numbers to the examples for the compounds according to the invention, in each case the numbering begins with Example 1:

Production of the Components of General Formula A from Pantolactone or from Malonic Acid Dialkyl Esters (DE 197 51 200.3 or PCT/EP98/05064)

EXAMPLE 1

(3S)-1-Oxa-2-oxo-3-(tetrahydropyran-2(RS)-yloxy)-4,4-dimethyl-cyclopentane

The solution of 74.1 g (569 mmol) of D-(−)-pantolactone in 1 l of anhydrous dichloromethane is mixed with 102 ml of 3,4-dihydro-2H-pyran and 2 g of p-toluenesulfonic acid-pyridinium salt under an atmosphere of dry argon, and it is stirred for 16 hours at 23° C. It is poured into a saturated sodium bicarbonate solution, the organic phase is separated and dried on sodium sulfate. After filtration and removal of the solvent, the residue is chromatographed on about 5 kg of fine silica gel with a mixture that consists of n-hexane and ethyl acetate. 119.6 g (558 mmol, 98%) of the title compound is isolated as a colorless oil.

$^1$H-NMR (CDCl$_3$): δ=1.13 (3H), 1.22 (3H), 1.46–1.91 (6H), 3.50–3.61 (1H), 3.86 (1H), 3.92 (1H), 4.01 (1H), 4.16 (1H), 5.16 (1H) ppm.

EXAMPLE 2

(2RS,3S)-1-Oxa-2-hydroxy-3-(tetrahydropyran-2 (RS)-yloxy)-4,4-dimethyl-cyclopentane The solution of 117.5 g (548 mmol) of the compound, presented according to Example 1, in 2.4 l of anhydrous toluene is cooled under an atmosphere of dry argon to –70° C., mixed within 1 hour with 540 ml of a 1.2 molar solution of diisobutylaluminum hydride in toluene, and it is stirred for 3 more hours at –70° C. It is allowed to heat to –20° C., mixed with saturated ammonium chloride solution, water, and the precipitated aluminum salts are separated by filtration on Celite. The filtrate is washed with water and saturated sodium chloride solution and dried on magnesium sulfate. After filtration and removal of the solvent, 111.4 g (515 mmol, 94%) of the title compound is isolated as a colorless oil, which is further reacted without purification. IR(CHCl$_3$) 3480, 3013, 2950, 2874, 1262, 1133, 1074, 1026 and 808 cm$^{-1}$.

EXAMPLE 3

(3S)-2,2-Dimethyl-3-(tetrahydropyran-2(R)-yloxy)-pent-4-en-1-ol and (3S)-2,2-dimethyl-3-(tetrahydropyran-2(S)-yloxy)-pent-4-en-1-ol The suspension of 295 g of methyl-triphenylphosphonium bromide in 2.5 l of anhydrous tetrahydrofuran is mixed under an atmosphere of dry argon at –60° C. with 313 ml of a 2.4 molar solution of n-butyllithium in n-hexane, allowed to heat to 23° C., stirred, for one more hour and cooled to 0° C. It is mixed with the solution of 66.2 g (306 mmol) of the compound, presented according to Example 2, in 250 ml of tetrahydrofuran, allowed to heat to 23° C. and stirred for 18 hours. It is poured into a saturated sodium bicarbonate solution, extracted several times with dichloromethane, and the combined organic extracts are dried on sodium sulfate. After filtration and removal of the solvent, the residue is chromatographed on about 5 l of fine silica gel with a gradient system that consists of n-hexane and ethyl acetate. 36.5 g (170 mmol, 56%) of the nonpolar THP-isomer of the title compound, 14.4 g (67.3 mmol, 22%) of the polar THP-isomer of the title compound, as well as 7.2 g (33.3 mmol; 11%) of the starting material in each case are isolated as a colorless oil.

$^1$H-NMR (CDCl$_3$), nonpolar isomer: δ=0.78 (3H), 0.92 (3H), 1.41–1.58 (4H), 1.63–1.87 (2H), 3.18 (1H), 3.41 (1H), 3.48 (1H), 3.68 (1H), 3.94 (1H); 4.00 (1H), 4.43 (1H), 5.19 (1H), 5.27 (1H), 5.75 (1H) ppm.

$^1$H-NMR (CDCl$_3$), polar isomer: δ=0.83 (3H), 0.93 (3H), 1.42–1.87 (6H), 2.76 (1H), 3.30 (1H), 3.45 (1H), 3.58 (1H), 3.83 (1H), 3.89 (1H), 4.65 (1H), 5.12–5.27 (2H), 5.92 (1H) ppm.

EXAMPLE 4

(3S)-1-(tert-Butyldiphenylsilyloxy)-2,2-dimethyl-pentane-3-(tetrahydropyran-2-yloxy)-pent-4-ene The solution of 59.3 g (277 mmol) of the THP-isomer-mixture, presented according to Example 3, in 1000 ml of anhydrous dimethyl-formamide is mixed under an atmosphere of dry argon with 28 g of imidazole and 85 ml of tert-butyldiphenylchlorosilane, and it is stirred for 16 hours at 23° C. It is poured into water, extracted several times with dichloromethane, the combined organic extracts are washed with water and dried on sodium sulfate. After filtration and removal of the solvent, the residue is chromatographed on fine silica gel with a gradient system that consists of n-hexane and ethyl acetate. 106.7 g (236 mmol, 85%) of the title compound is isolated as a colorless oil.

$^1$H-NMR (CDCl$_3$): δ=0.89 (3H), 0.99 (3H), 1.08 (9H), 1.34–1.82 (6H), 3.40 (1H), 3.51 (2H), 3.76 (1H), 4.02 (1H), 4.67 (1H), 5.18 (1H), 5.23 (1H), 5.68 (1H), 7.30–7.48 (6H), 7.60–7.73 (4H) ppm.

EXAMPLE 5

(3S)-1-(tert-Butyldiphenylsilyloxy)-2,2-dimethyl-3-(tetrahydropyran-2-yloxy)-pentan-5-ol The solution of 3.09 g (6.83 mmol) of the compound, presented according to Example 4, in 82 ml of tetrahydrofuran is mixed with 13.1 ml of a 1 molar solution of borane in tetrahydrofuran under an atmosphere of dry argon at 23° C., and it is allowed to react for 1 hour. Then, while being cooled with ice, it is mixed with 16.4 ml of a 5% sodium hydroxide solution as well as 8.2 ml of a 30% hydrogen peroxide solution, and it is stirred for another 30 minutes. It is poured into water, extracted several times with ethyl acetate, the combined organic extracts are washed with water, saturated sodium chloride solution and dried on magnesium sulfate. The residue that is obtained after filtration and removal of the solvent is purified by chromatography on fine silica gel with a gradient system that consists of n-hexane and ethyl acetate. 1.78 g (3.78 mmol, 55%) of the title compound is isolated as a chromatographically separable mixture of the two THP-epimers, as well as 0.44 g (1.14 mmol, 17%) of the title compound of Example 6 in each case as a colorless oil.

$^1$H-NMR (CDCl$_3$), nonpolar THP-isomer: δ=0.80 (3H), 0.88 (3H), 1.10 (9H), 1.18–1.80 (9H), 3.27 (1H), 3.39 (1H), 3.48 (1H), 3.64 (1H, 3.83 (1H), 3.90–4.08 (2H), 4.49 (1H), 7.31–7.50 (6H), 7.58–7.73 (4H) ppm.

$^1$H-NMR (CDCl$_3$), polar THP-isomer: δ=0.89 (3H), 0.98 (3H), 1.08 (9H), 1.36–1.60 (4H), 1.62–1.79 (3H), 1.88 (1H), 2.03 (1H), 3.37 (1H), 3.50 (1H), 3.57 (1H), 3.62–3.83 (4H), 4.70 (1H), 7.30–7.48 (6H), 7.61–7.73 (4H) ppm.

EXAMPLE 6

(3S)-1-(tert-Butyldiphenylsilyloxy)-2,2-dimethyl-pentane-3,5-diol

The solution of 570 mg (1.55 mmol) of the compound, presented according to Example 12, is reacted analogously to Example 5, and after working-up and purification, 410 mg (1.06 mmol, 68%) of the title compound is isolated as a colorless oil.

$^1$H-NMR (CDCl$_3$): δ=0.82 (3H), 0.93 (3H), 1.08 (9H), 1.56–1.79 (2H), 3.11 (1H), 3.50 (2H), 3.78–3.92 (3H), 4.02 (1H), 7.34–7.51 (6H), 7.61–7.71 (4H) ppm.

EXAMPLE, 7, VARIANT I

4(S)-[2-Methyl-1-(tert-butyldiphenylsilyloxy)-prop-2-yl]-2,2-dimethyl-[1,3]dioxane The solution of 100 mg (0.212 mmol) of the compounds, presented according to Example 5, in 2.6 ml of anhydrous acetone is mixed with 78.9 mg of copper(II) sulfate, a spatula tip full of p-toluenesulfonic acid-monohydrate under an atmosphere of dry argon, and it is stirred for 16 hours at 23° C. It is mixed with saturated sodium bicarbonate solution, extracted several times with diethyl ether, washed with saturated sodium chloride solution and dried on sodium sulfate. The residue that is obtained after filtration and removal of the solvent is purified by chromatography on fine silica gel with a gradient system that consists of n-hexane and ethyl acetate. 24 mg (56 µmol, 27%) of the title compound is isolated as a colorless oil.

$^1$H-NMR (CDCl$_3$): δ=0.83 (3H), 0.89 (3H), 1.07 (9H), 1.30 (1H), 1.36 (3H), 1.44 (3H), 1.71 (1H), 3.24 (1H), 3.62 (,1H), 3.86 (1H), 3.91–4.03 (2H), 7.31–7.48 (6H), 7.61–7.74 (4H) ppm.

Variant II 320 mg (0.88 mmol) of the compound, presented according to Example 6, is reacted analogously to Example 7; variant 1, and after working-up and purification, 234 mg (0.548 mmol, 62%) of, the title compound is isolated.

Variant III

The solution of 5.60 g (14.5 mmol) of the compound, presented according to Example 6, in 250 ml of anhydrous dichloromethane, is mixed with 10 ml of 2,2-dimethoxypropane, 145 mg of camphor-10-sulfonic acid under an atmosphere of dry argon, and it is stirred for 6 hours at 23° C. It is mixed with triethylamine, diluted with ethyl acetate, washed with saturated sodium bicarbonate solution and dried on sodium sulfate. After filtration and removal of the solvent, the residue is chromatographed on fine silica gel with a mixture that consists of n-hexane and ethyl acetate. 5.52 g (12.9 mmol, 89%) of the title compound is isolated as a colorless oil.

EXAMPLE 8

(4S)-4-(2-Methyl-1-hydroxy-prop-2-yl)-2,2-dimethyl-[1,3]dioxane

The solution of 5.6 g (13.1 mmol) of the compound, presented according to Example 7, in 75 ml of anhydrous tetrahydrofuran is mixed with 39 ml of a 1 molar solution of tetrabutylammonium fluoride in tetrahydrofuran under an atmosphere of dry argon, and it is heated for 16 hours to 50° C. It is mixed with saturated sodium bicarbonate solution, extracted several times with ethyl acetate, washed with saturated sodium chloride solution and dried on sodium sulfate. The residue that is obtained after filtration and removal of the solvent is purified by chromatography on fine silica gel with a gradient system that consists of n-hexane and ethyl acetate. 2.43 g (12.9 mmol, 99%) of the title compound is isolated as a colorless oil.

$^1$H-NMR (CDCl$_3$) δ=0.87 (3H), 0.90 (3H), 1.35 (1H), 1.37 (3H), 1.43 (3H), 1.77 (1H), 2.93 (1H), 3.36 (1H), 3.53 (1H), 3.79 (1H), 3.87 (1H), 3.96 (1H) ppm.

EXAMPLE 9

(4S)-4-(2-Methyl-1-oxo-prop-2-yl)-2,2-dimethyl-[1,3]dioxane

The solution of 0.13 ml of oxalyl chloride in 5.7 ml of anhydrous dichloromethane is cooled under an atmosphere of dry argon to −70° C., mixed with 0.21 ml of dimethyl sulfoxide, the solution of 200 mg (1.06 mmol) of the compound, presented according to Example 8, in 5.7 ml of anhydrous dichloromethane, and it is stirred for 0.5 hour. Then, it is mixed with 0.65 ml of triethylamine, allowed to react for 1 hour at −30° C. and mixed with n-hexane and saturated sodium bicarbonate solution. The organic phase is separated, the aqueous phase is extracted several more times with n-hexane, the combined organic extracts are washed with water and dried on magnesium sulfate. The residue that is obtained after filtration and removal of the solvent is further reacted without purification.

EXAMPLE 10

(4S)-4-(2-Methyl-3(RS)-hydroxy-pent-2-yl)-2,2-dimethyl-[1,3]dioxane

The solution of 900 mg (4.83 mmol) of the compound, presented according to Example 9, in 14 ml of anhydrous diethyl ether is mixed under an atmosphere of dry argon at 0° C. with 2.42 ml of a 2.4 molar solution of ethylmagnesium bromide in diethyl ether, allowed to heat to 23° C. and stirred for 16 hours. It is mixed with saturated ammonium chloride solution, the organic phase is separated and dried on sodium sulfate. The residue that is obtained after filtration and removal of the solvent is purified by chromatography on fine silica gel with a gradient system that consists of n-hexane and ethyl acetate. 321 mg (1.48 mmol, 31%) of the nonpolar 3R- or 3S-epimer of the title compound, 542 mg (2.51 mmol, 52%) of the polar 3S- or 3R-epimer of the title compound as well as 77 mg of the title compound that is described in Example 8 are isolated in each case as a colorless oil.

$^1$H-NMR (CDCl$_3$) of nonpolar isomer: δ=0.86 (3H), 0.89 (3H), 1.03 (3H), 1.25–1.37 (2H), 1.37 (3H), 1.46 (3H), 1.49 (1H), 1.84 (1H), 3.35 (1H), 3.55 (1H), 3.81–4.02 (3H) ppm.

$^1$H-NMR (CDCl$_3$) of polar isomer: δ=0.72 (3H), 0.91 (3H), 0.99 (3H), 1.25–1.44 (2H), 1.38 (3H), 1.43–1.60 (1H), 1.49 (3H), 1.76 (1H), 3.39 (1H), 3.63 (1H), 3.79–4.03 (3H) ppm.

EXAMPLE 11

(4S)-4-(2-Methyl-3-oxo-pent-2-yl)-2,2-dimethyl-[1,3]dioxane

The solution of 850 mg (3.93 mmol) of a mixture of the compounds, presented according to Example 10, in 63 ml of anhydrous dichloromethane is mixed with a molecular sieve (4A, about 80 balls), 690 mg of N-methylmorpholino-N-oxide, 70 mg of tetrapropylammonium perruthenate, and it is stirred for 16 hours at 23° C. under an atmosphere of dry argon. It is concentrated by evaporation, and the crude product that is obtained is purified by chromatography on about 200 ml of fine silica-gel with a gradient system that consists of n-hexane and ethyl acetate. 728 mg (3.39 mmol, 86%) of the title compound is isolated as a colorless oil.

$^1$H-NMR (CDCl$_3$): δ=1.00 (3H), 1.07 (3H), 1.11 (3H), 1.31 (1H), 1.32 (3H), 1.41 (3H), 1.62 (1H), 2.52 (2H), 3.86 (1H), 3.97 (1H), 4.05 (1H) ppm.

EXAMPLE 12

(3S)-1-(tert-Butyldiphenylsilyloxy)-2,2-dimethyl-3-hydroxy-pent-4-ene

The solution of 106.7 g (236 mmol) of the compound, presented according to Example 4, in 1.5 l of anhydrous ethanol is mixed with 5.9 g of pyridinium-p-toluenesulfonate under an atmosphere of dry argon, and it is heated for 6 hours to 50° C. After removal of the solvent, the residue is chromatographed on fine silica gel with a mixture that consists of n-hexane and ethyl acetate. 82.6 g (224 mmol, 95%) of the title compound is isolated as a colorless oil, in which in addition about 5 g of ethoxy-tetrahydropyran is contained.

$^1$H-NMR (CDCl$_3$) of an analytic sample: δ=0.89 (6H), 1.08 (9H), 3.45 (1H), 3.49 (1H), 3.58 (1H), 4.09 (1H), 5.21 (1H), 5.33 (1H), 5.93 (1H), 7.34–7.51 (6H), 7.63–7.73 (4H) ppm.

EXAMPLE 13

(4S)-4-((2RS)-3-Methyl-2-hydroxy-prop-3-yl)-2,2-dimethyl-[1,3]dioxane

Analogously to Example 10, 450 mg (2.42 mmol) of the compound that is presented according to Example 9 is reacted with use of methylmagnesium bromide. After working-up and purification, 431 mg (2.13 mmol, 88%) of a chromatographically separable mixture of the epimeric title compounds is isolated as a colorless oil.

EXAMPLE 14

(4S)-4-(3-Methyl-2-oxo-prop-3-yl)-2,2-dimethyl-[1,3]dioxane

Analogously to Example 11, 420 mg (2.08 mmol) of the compounds that are presented according to Example 13 is reacted. After working-up and purification, 388 mg (1.94 mmol, 93%) of the title compound is isolated as a colorless oil.

$^1$H-NMR (CDCl$_3$): δ=1.08 (3H), 1.12 (3H), 1.33 (3H), 1.35 (1H), 1.42 (3H), 1.63 (1H), 2.17 (3H), 3.87 (1H), 3.98 (1H), 4.04 (1H) ppm.

EXAMPLE 15

(4S)-4-((3RS)-2-Methyl-3-hydroxy-hex-2-yl)-2,2-dimethyl-[1,3]dioxane

Analogously to Example 10, 450 mg (2.42 mmol) of the compound that is presented according to Example 9 is reacted with use of n-propylmagnesium bromide. After working-up and purification, a total of 244 mg (1.06 mmol, 44%) of a separable mixture of the epimeric title compounds and 191 mg of the title compound that is described in Example 8 is isolated in each case as a colorless oil.

$^1$H-NMR (CDCl$_3$) of nonpolar isomer: δ=0.87 (3H), 0.89 (3H), 0.94 (3H), 1.25–1.52 (4H), 1.38 (3H), 1.45 (3H), 1.66 (1H), 1.85 (1H), 3.46 (1H), 3.80–4.02 (4H) ppm.

$^1$H-NMR (CDCl$_3$) of polar isomer: δ=0.73 (3H), 0.92 (3H), 0.95 (3H), 1.19–1.84 (6H), 1.37 (3H), 1.49 (3H), 3.49 (1H), 3.60 (1H), 3.80–4.03 (3H) ppm.

EXAMPLE 16

(4S)-4-(2-Methyl-3-oxo-hex-2-yl)-2,2-dimethyl-[1,3]dioxane

Analogously to Example 11, 230 mg (1.00 mmol) of the compounds that are presented according to Example 15 is reacted. After working-up and purification, 185 mg (0.81 mmol, 81%) of the title compound is isolated as a colorless oil.

$^1$H-NMR (CDCl$_3$): δ=0.88 (3H), −1.04 (3H), 1.12 (3H), 1.22–1.37 (1H), 1.31 (3H), 1.40 (3H), 1.48–1.71 (3H), 2.46 (2H), 3.83 (1H), 3.96, (H), 4.04 (1H) ppm.

EXAMPLE 17

(4R)-4-(2-Methyl-3-oxo-pent-2-yl)-2,2-dimethyl-[1,3]dioxane

Starting from L-(+)-pantolactone, the title compound is produced via the respective enantiomeric intermediate stages analogously to the processes that are described in Examples 1 to 9 and 12.

$^1$H-NMR (CDCl$_3$): δ=1.00 (3H), 1.07 (3H), 1.12 (3H), 1.24–1.37 (1H), 1.31 (3H), 1.40 (3H), 1.61 (1H), 2.50 (2H), 3.84 (1H), 3.95 (1H), 4.03 (1H) ppm.

EXAMPLE 18

(4R)-4-(3-Methyl-2-oxo-prop-3-yl)-2,2-dimethyl-[1,3]dioxane

Starting from L-(+)-pantolactone, the title compound is produced via the respective enantiomeric intermediate stages analogously to the processes that are described in Examples 1 to 9 and 12 to 14.

$^1$H-NMR (CDCl$_3$): δ=1.07 (3H), 1.12 (3H), 1.30–1.39 (1H), 1.33 (3H), 1.43 (3H), 1.62 (1H), 2.17 (3H), 3.86 (1H), 3.96 (1H) 4.03 (1H) ppm.

EXAMPLE 19

(4R)-4-(2-Methyl-3-oxo-hex-2-yl)-2,2-dimethyl-[1,3]dioxane

Starting from L-(+)-pantolactone, the title compound is produced via the respective enantiomeric intermediate stages analogously to the processes that are described in Examples 1 to 9, 12, 15 and 16.

$^1$H-NMR (CDCl$_3$): δ=0.88 (3H), 1.04 (3H), 1.12 (3H), 1.22–1.37 (1H), 1.31 (3H), 1.41 (3H), 1.48–1.72 (3H), 2.47 (2H), 3.84 (1H), 3.96 (1H), 4.05 (1H) ppm.

EXAMPLE 20

(2S,4S)-2-(2-Cyanophenyl)-4-[2-methyl-1-(tert-butyldiphenylsilyloxy)-prop-2-yl]-[1,3]dioxane The solution of 1.00 g (2.59 mmol) of the compound, presented according to Example 6, in 50 ml of benzene, is mixed with 850 mg of 2-cyanobenzaldehyde, a spatula tip full of p-toluenesulfonic acid-monohydrate, and it is refluxed for 16 hours in a water separator under an atmosphere of dry argon. It is mixed with 0.5 ml of triethylamine, diluted with ethyl acetate, washed with saturated sodium bicarbonate solution and dried on sodium sulfate. After filtration and removal of the solvent, the residue is chromatographed on fine silica gel with a mixture that consists of n-hexane and ethyl acetate. 1.22 g (2.44 mmol, 94%) of the title compound is isolated as a colorless oil.

$^1$H-NMR (CDCl$_3$): δ=0.99 (6H), 1.05 (9H), 1.47 (1H), 1.98 (1H), 3.34 (1H), 3.63 (1H), 3.96–4.09 (2H), 4.31 (1H), 5.75 (1H), 7.17 (2H), 7.24–7.51 (5H), 7.51–7.74 (7H) ppm.

EXAMPLE 21

(2S,4S)-2-(2-Cyanophenyl)-4-(2-methyl-1-hydroxy-prop-2-yl) -[1,3]dioxane

Analogously to Example 8, 1.22 g (2.44 mmol) of the compound that is presented according to Example 20 is reacted and, after working-up and purification, 593 mg (2.27 mmol, 93%) of the title compound is isolated as a colorless oil.

$^1$H-NMR (CDCl$_3$) δ=0.89 (3H), 0.97 (3H), 1.51 (1H), 2.01 (1H), 2.42 (1H), 3.31 (1H), 3.72 (1H), 3.97 (1H), 4.02 (1H), 4.39 (1H), 5.78 (1H), 7.46 (1H), 7.63 (1H), 7.69 (1H), 7.75 (1H) ppm.

EXAMPLE 22

(2S,4S)-2-(2-Cyanophenyl)-4-(2-methyl-1-oxo-prop-2-yl) -[1,3]dioxane

Analogously to Example 9, 570 mg (2.18 mmol) of the compound that is presented according to Example 21 is reacted, and after working-up, 780 mg of the title compound is isolated as a yellow oil, which is further reacted without purification.

EXAMPLE 23

(2S,4S)-2-(2-Cyanophenyl)-4-((3RS)-2-methyl-3-hydroxy-pent-2-yl) -[1,3]dioxane

Analogously to Example 10, 780 mg (maximum 2.18 mmol) of the crude product that is presented according to Example 22 is reacted, and after working-up and purification, 468 mg (1.62 mmol, 74%) of the epimeric title compounds is isolated as a colorless oil.

$^1$H-NMR (CDCl$_3$): δ=0.81–1.09 (9H), 1.22–1.43 (1H), 1.43–1.70 (2H), 2.04 (1H), 2.35 (0.55H), 2.89 (0.45H), 3.41–3.59 (1H), 3.89–4.13 (2H), 4.36 (1H), 5.78 (0.45H), 5.81 (0.55H), 7.45 (1H), 7.54–7.78 (3H) ppm.

EXAMPLE 24

(2S,4S)-2-(2-Cyanophenyl)-4-(2-methyl-3-oxo-pent-2-yl) -[1,3]dioxane

Analogously to Example 11, 463 mg (1.60 mmol) of the compound that is presented according to Example 23 is reacted, and after working-up and purification, 420 mg (1.46 mmol, 91%) of the title compound is isolated as a colorless oil.

$^1$H-NMR (CDCl$_3$): δ=1.00 (3H), 1.19 (3H), 1.24 (3H), 1.49 (1H), 1.92 (1H), 2.56 (2H), 4.03 (1H), 4.16 (1H), 4.32 (1H), 5.78 (1H), 7.44 (1H), 7.60 (1H), 7.64–7.72 (2H) ppm.

EXAMPLE 25

(4S,2S)-4-[2-Methyl-1-(tert-butyldiphenylsilyloxy)-prop-2-yl]-2-phenyl-[1,3]dioxane Analogously to Example 20, 1.00 g (2.59 mmol) of the compound, presented according to Example 6, in 5.0 ml of toluene is reacted with use of benzaldehyde, and after working-up and purification, 1.2 g (2.53 mmol, 98%) of the title compound is isolated as a colorless oil.

$^1$H-NMR (CDCl$_3$) δ=0.93 (3H), 1.00 (3H), 1.07 (9H), 1.43 (1H), 1.92 (1H), 3.30 (1H), 3.72 (1H), 3.95 (1H), 4.00 (1H), 4.30 (1H), 5.53 (1H), 7.18 (2H), 7.29–7.49 (9H), 7.61 (2H), 7.67 (2H) ppm.

EXAMPLE 26

(4S,2S)-4-(2-Methyl-1-hydroxy-prop-2-yl)-2-phenyl-[1,3]dioxane

Analogously to Example 8, 1.20 g (2.53 mmol) of the compound that is presented according to Example 25 is reacted, and after working-up and purification, 518 mg (2.19 mmol, 87%) of the title compound is isolated as a colorless oil.

$^1$H-NMR (CDCl$_3$): δ=0.98 (6H), 1.49 (1H), 2.00 (1H), 2.49(1H), 3.46 (1H), 3.62 (1H), 3.81 (1H), 3.98 (1H), 4.33 (1H), 5.51 (1H), 7.30–7.41 (3H), 7.41–7.51 (2H) ppm.

EXAMPLE 27

(2S,4S)-4-(2-Methyl-1-oxo-prop-2-yl)-2-phenyl-[1,3]dioxane

Analogously to Example 9, 500 mg (2.12 mmol) of the compound that is presented according to Example 26 is reacted, and after working-up, 715 mg of the title compound is isolated as a yellow oil, which is further reacted without purification.

EXAMPLE 28

(2S,4S)-4-((3RS)-2-Methyl-3-hydroxy-pent-2-yl)-2-phenyl -[1,3]dioxane

Analogously to Example 10, 715 mg (maximum 2.12 mmol) of the crude product that is presented according to Example 27 is reacted, and after working-up and purification, 440 mg (1.66 mmol, 79%) of the epimeric title compound is isolated as a colorless oil.

$^1$H-NMR (CDCl$_3$) δ=0.80–1.10 (9H), 1.23–1.42 (1H), 1.42–1.70 (2H), 1.90–2.16 (1H), 2.92 (0.6H)i 3.07 (0.4H), 3.40–3.53 (1H), 3.86 (1H), 3.98 (1H), 4.32 (1H), 5.49 (0.4H), 5.55 (0.6H), 7.28–7.40 (3H), 7.40–7.51 (2H) ppm.

EXAMPLE 29

(2S,4S)-4-(2-Methyl-3-oxo-pent-2-yl)-2-phenyl-[1,3]dioxane

Analogously to Example 11, 435 mg (1.65 mmol) of the compound that is presented according to Example 28 is reacted, and after working-up and purification, 410 mg (1.56 mmol, 95%) of the title compound is isolated as a colorless oil.

$^1$H-NMR (CDCl$_3$): δ=1.02 (3H), 1.17 (3H), 1.23 (3H), 1.44 (1H), 1.84 (1H), 2.58 (2H), 3.97 (1H), 4.06 (1H), 4.30 (1H), 5.50 (1H), 7.28–7.49 (5H) ppm.

EXAMPLE 30

(4S)-4-[2-Methyl-1-(tert-butyldiphenylsilyloxy)-prop-2-yl]-2,2-pentamethylene-[1,3]dioxane Analogously to Example 20, 1.00 g (2.59 mmol) of the compound, presented according to Example 6, in 50 ml of toluene is reacted with use of cyclohexanone, and after working-up and purification, 1.09 g (2.34 mmol, 90%) of the title compound is isolated as a colorless oil.

$^1$H-NMR (CDCl$_3$): δ=0.84 (3H), 0.89 (3H), 0.97–1.10 (10H), 1.20–1.64 (9H), 1.71 (1H), 2.13 (1H), 3.33 (1H), 3.56 (1H), 3.81 (1H), 3.89 (1H), 3.99 (1H), 7.32–7.49 (6H), 7.60–7.74 (4H) ppm.

EXAMPLE 31

(4S)-4-(2-Methyl-1-hydroxy-prop-2-yl)-2,2-pentamethylene -[1,3]dioxane

Analogously to Example 8, 1.09 g (2.34 mmol) of the compound that is presented according to Example 30 is reacted, and after working-up and purification, 470 mg (2.06 mmol, 88%) of the title compound is isolated as a colorless oil.

$^1$H-NMR (CDCl$_3$): δ=0.88 (3H), 0.94 (3H), 1.24–1.71 (10H), 1.81 (1H), 2.18 (1H), 3.09 (1H), 3.39 (1H), 3.60 (1H), 3.80 (1H), 3.87 (1H), 4.02 (1H) ppm.

EXAMPLE 32

(4S)-4-(2-Methyl-1-oxo-prop-2-yl)-2,2-pentamethylene-[1,3]dioxane

Analogously to Example 9, 450 mg (1.97 mmol) of the compound that is presented according to Example 31 is reacted, and after working-up, 678 mg of the title compound is isolated as a yellow oil, which is further reacted without purification.

EXAMPLE 33

(4S)-4-(2-Methyl-3-hydroxy-pent-2-yl)-2,2-pentamethylene -[1,3]dioxane

Analogously to Example 10, 678 mg (maximum 1.97 mmol) of the crude product that is presented according to Example 32 is reacted, and after working-up and purification, 391 mg (1.54 mmol, 77%) of the epimeric title compounds is isolated as a colorless oil.

$^1$H-NMR (CDCl$_3$): δ=0.70–1.08 (9H), 1.23–1.98 (13H), 2.01–2.13 (1H), 3.37–3.50 (1H), 3.61 (0.5H), 3.80–4.06 (3.5H) ppm.

EXAMPLE 34

(4S)-(2-Methyl-3-oxo-pent-2-yl)-2,2-pentamethylene-[1,3]dioxane

Analogously to Example 11, 386 mg (1.51 mmol) of the compound that is presented according to Example 33 is reacted, and after working-up and purification, 376 mg (1.48 mmol, 98%) of the title compound is isolated as a colorless oil.

$^1$H-NMR (CDCl$_3$) δ=1.01 (3H), 1.09 (3H), 1.17 (3H), 1.22–1.38 (3H), 1.40–1.72 (8H), 2.15 (1H), 2.57 (2H), 3.81 (1H), 3.92–4.07 (2H) ppm.

EXAMPLE 35

(4S)-4-[2-Methyl-1-(tert-butyldiphenylsilyloxy)-prop-2-yl]-2,2-tetramethylene-[1,3]dioxane Analogously to Example 20, 1.00 g (2.59 mmol) of the compound, presented according to Example 6, in 50 ml of toluene is reacted with use of cyclopentanone, and after working-up and purification, 997 mg (2.20 mmol, 85%) of the title compound is isolated as a colorless oil.

$^1$H-NMR (CDCl$_3$): δ=0.84 (3H), 0.88 (3H), 0.99–1.10 (10H), 1.30 (1H), 1.50–1.99 (8H), 3.23 (1H), 3.60 (1H), 3.80–3.98 (3H), 7.31–7.49 (6H), 7.61–7.73 (4H) ppm.

EXAMPLE 36

(4S)-4-(2-Methyl-1-hydroxy-prop-2-yl)-2,2-tetramethylene -[1,3]dioxane

Analogously to Example 8, 997 mg (2.20 mmol) of the compound that is presented according to Example 35 is reacted, and after working-up and purification, 415 mg (1.94 mmol, 88%) of the title compound is isolated as a colorless oil.

$^1$H-NMR (CDCl$_3$): δ=0.90 (6H), 1.36 (1H), 1.53–2.02 (9H), 2.93 (1H), 3.39 (1H), 3.55 (1H), 3.70 (1H), 3.87 (1H), 3.96 (1H) ppm.

EXAMPLE 37

(4S)-4-(2-Methyl-1-oxo-prop-2-yl)-2,2-tetramethylene-[1,3]dioxane

Analogously to Example 9, 400 mg (1.87 mmol) of the compound that is presented according to Example 36 is reacted, and after working-up, 611 mg of the title compound is isolated as a yellow oil, which is further reacted without purification.

EXAMPLE 38

(4S)-4-(2-Methyl-3-hydroxy-pent-2-yl)-2,2-tetramethylene-[1,3]dioxane

Analogously to Example 10, 611 mg (maximum 1.87 mmol) of the compound that is presented according to Example 37 is reacted, and after working-up and purification, 353 mg (1.46 mmol, 78%) of the epimeric title compounds is isolated as a colorless oil.

$^1$H-NMR (CDCl$_3$): δ=0.71–1.09 (9H), 1.20–1.44 (2H), 1.44–1.78 (5H), 1.78–2.02 (5H), 3.32–3.44 (1H), 3.51–3.60 (1H), 3.76 (1H), 3.80–4.02 (2H) ppm.

EXAMPLE 39

(4S)-4-(2-Methyl-3-oxo-pent-2-yl)-2,2-tetramethylene-[1,3]dioxane

Analogously to Example 11, 348 mg (1.44 mmol) of the compound that is presented according to Example 38 is reacted, and after working-up and purification, 332 mg (1.38 mmol, 96%) of the title compound is isolated as a colorless oil.

$^1$H-NMR (CDCl$_3$) δ=1.00 (3H), 1.07 (3H), 1.17 (3H), 1.31 (1H), 1.50–2.00 (9H), 2.52 (2H), 3.84 (1H), 3.88–3.99 (2H) ppm.

EXAMPLE 40

1,1-Cyclobutanedimethanol 170 ml of a 1.2 molar solution of diisobutylaluminum hydride is added in drops at ° C. to a solution of 20 g (99.9 mmol) of 1,1-cyclobutanedicarboxylic acid diethyl ester in 200 ml of absolute tetrahydrofuran. It is allowed to stir for one more hour at 0° C., and then 30 ml of water is added. It is filtered on Celite. The filtrate is dried with sodium sulfate and concentrated by evaporation in a vacuum. The crude product that is obtained (9.9 g, 85.2 mmol, 85%) is used without purification in the next step.

EXAMPLE 41

1-[[[Dimethyl(1,1-dimethylethyl)silyl]oxy]methyl]cyclobutane methanol

A solution of 9.9 g (85 mmol) of the compound, presented according to Example 40, in 100 ml of absolute tetrahydrofuran is added at 0° C. to a suspension of 3.4 g of sodium hydride (60% in oil) in 35 ml of absolute tetrahydrofuran. It is allowed to stir for 30 more minutes, and then a solution of 12.8 g of tert-butyldimethylsilyl chloride in 50 ml of tetrahydrofuran is added. It is allowed to stir for one more hour at 25° C., and then the reaction mixture is poured onto saturated aqueous sodium bicarbonate solution. It is extracted with ethyl acetate. The organic phase is washed with saturated sodium chloride solution and dried on sodium sulfate. After the solvent is drawn off in a vacuum, the crude product that is obtained is purified by column chromatography on silica gel with a mixture that consists of hexane/ethyl acetate. 13.5 g (58.6 mmol, 69%) of the title compound is obtained.

$^1$H-NMR (CDCl$_3$): δ=0.04 (6H), 0.90 (9H), 1.70–2.00 (6H), 3.70 (4H) ppm.

EXAMPLE 42

1-[[[Dimethyl(1,1-dimethylethyl)silyl]oxy]methyl]cyclobutanecarbaldehyde 8 ml of oxalyl chloride is dissolved in 100 ml of dichloromethane. It is cooled to −78° C., and 13 ml of dimethyl sulfoxide is added. It is allowed to stir for 3 more minutes, and then a solution of 13.5 g (58.6 mmol) of the compound, presented according to Example 41, in 80 ml of dichloromethane is added. After another 15 minutes of stirring time, 58 ml of triethylamine is added in drops. Then, it is allowed to heat to 0° C. Then, the reaction mixture is poured onto saturated sodium bicarbonate solution. It is extracted with dichloromethane, the organic phase is washed with saturated sodium chloride solution, dried on sodium sulfate and concentrated by evaporation in a vacuum. After chromatography of the crude product on silica gel with a mixture that consists of hexane/ethyl acetate, 7.7 g (33.7 mmol, 58%) of the title compound is obtained.

$^1$H-NMR (CDCl$_3$) δ=9.70 s (1H), 3.83 s (2H), 2.20–2.30 m (2H), 1.85–2.00 m (4H), 0.90 s (9H), 0.03 s (6H) ppm.

EXAMPLE 43

[1R-[1α(R*),2:β]-2-Phenylcyclohexyl 3-[-1-[[[dimethyl(1,1-dimethylethyl)silyl]oxy]methyl]cyclobutyl]-3-hydroxypropanoate (A) and

[1R-[1α(S*),2β]]-2-phenylcyclohexyl 3-[-1-[[[dimethyl(1,1-dimethylethyl)silyl]oxy]methyl]cyclobutyl]-3-hydroxypropanoate (B)

Lithium diisopropylamide is produced in absolute tetrahydrofuran from 7.2 ml of diisopropylamine and butyllithium (32 ml of a 1.6 molar solution in hexane). Then, a solution of 11.2 g (1R-trans)-2-phenylcyclohexyl acetate in 100 ml of absolute tetrahydrofuran is added at −78° C. and allowed to stir for 30 more minutes at this temperature. Then, a solution of 7.7 g (33.7 mmol) of the compound, presented according to Example 42, in 50 ml of tetrahydrofuran is added. It is allowed to stir for 1.5 more hours at −78° C., and then the reaction mixture is poured onto saturated aqueous ammonium chloride solution. It is extracted with ethyl acetate, the organic phase is washed with saturated sodium chloride solution, dried on sodium sulfate and concentrated by evaporation in a vacuum. After column chromatography of the crude product on silica gel with a mixture that consists of hexane/ethyl acetate, 6.34 g (14.2 mmol, 42%) of title compound A and 4.22 g (9.4 mmol, 28%y) of title compound B are obtained.

$^1$'-NMR (CDCl$_3$) of A: δ=0.04 (6H), 0.98 (9H), 2.69 (1H), 3.08 (1H), 3.60 (1H), 3.67 (1H), 3.78–3.84 (1H), 4.97 (1H), 7.15–7.30 (5H) ppm.

$^1$H-NMR (CDCl$_3$) of B: δ=0.03 (6H), 0.90 (9H), 2.68 (1H), 2.80 (1H), 3.56 (2H), 3.68–3.72 (1H), 4.99 (1H), 7.18–7.30 m (5H) ppm.

EXAMPLE 44

(S)-1-[1-[[[Dimethyl(1,1-dimethylethyl)silyl]oxy]-methyl]cyclobutyl]-1,3-propanediol 4 ml of a 1.2 molar solution of diisobutylaluminum hydride in toluene is added in drops at 0° C. to a solution of 1 g (2.24 mmol) of compound A, presented according to Example 43, in 10 ml of absolute toluene. It is allowed to stir for 1.5 more hours at 0° C., and then 5 ml of water is added. It is filtered on Celite. The filtrate is dried on sodium sulfate and concentrated by evaporation in a vacuum. After column chromatography of the crude product on silica gel with a mixture that consists of hexane/ethyl acetate, 370 mg (1.35 mmol, 60%) of the title compound is obtained.

$^1$H-NMR (CDCl$_3$): =0.05 (6H), 0.90 (9H), 1.55–1.60 (2H), 1.80 (2H), 1.90 (3H), 2.10 (1H), 3.75 (1H), 3.85–3.95 (4H) ppm.

EXAMPLE 45

(S)-2,2-Dimethyl-4-[[[dimethyl(1,1-dimethylethyl)silyl]oxy]methyl]cyclobutyl]-1,3-dioxane 370 mg (1.35 mmol) of the compound that is presented according to Example 44 is dissolved in 10 ml of acetone. A spatula tip full of p-toluenesulfonic acid is added, and it is allowed to stir for 2 more hours at 25° C. Then, the reaction mixture is poured onto saturated sodium bicarbonate solution. It is extracted with ethyl acetate, the organic phase is washed with saturated sodium chloride solution, dried on sodium sulfate and concentrated by evaporation in a vacuum. After column chromatography on silica gel with a mixture that consists of hexane/ethyl acetate, 338 mg (1.07 mmol, 79%) of the title compound is obtained.

$^1$H-NMR (CDCl$_3$): δ=0.03 (6H), 0.88 (9H), 1.38 (3H), 1.42 (3H), 1.50–1.80 (4H), 2.00 (1H), 3.52 (1H), 3.62 (1H), 3.85–4.00 (3H) ppm.

EXAMPLE 46

(R)-1-[1-[[[Dimethyl(1,1-dimethylethyl)silyl]oxy]-methyl]cyclobutyl]-1,3-propanediol Analogously to Example 44, 700 mg (1.57 mmol) of compound B that is produced according to Example 43 is reacted, and after working-up and purification, 250 mg (0.91 mmol, 58%) of the title compound is isolated.

The coverage of the $^1$H-NMR spectrum is identical to that described in Example 44.

EXAMPLE 47

(R)-2,2-Dimethyl-4-[[[dimethyl(1,1-dimethylethyl) silyl]oxy]methyl]cyclobutyl]-1,3-dioxane Analogously to Example 45, 250 mg (0.91 mmol) of the compound that is produced according to Example 46 is reacted, and after working-up and purification, 228 mg (0.72 mmol, 60%) of the title compound is isolated.

The coverage of the $^1$H-NMR spectrum is identical to that described in Example 45.

EXAMPLE 48

1-[1-[[[Dimethyl(1,1-dimethylethyl)silyl]oxy]methyl] cyclobutyl]-1,3-propanediol Analogously to Example 44, 500 mg (1.12 mmol) of admixture of compounds A and B that are produced according to Example 43 is reacted, and after working-up and purification, 190 mg (0.69 mmol, 62%) of the title compound is isolated.

The coverage of the $^1$H-NMR spectrum is identical to that described in Example 44.

EXAMPLE 49

2,2-Dimethyl-4-[1-[[[dimethyl(1,1-dimethylethyl)silyl] oxy]-methyl]cyclobutyl]-1,3-dioxane Analogously to Example 45, 190 mg (0.69 mmol) of the compound that is produced according to Example 48 is reacted, and after working-up and purification, 171 mg (0.54 mmol, 79%) of the title compound is isolated.

The coverage of the $^1$H-NMR spectrum is identical to that described in Example 45.

EXAMPLE 50

[1R-[1α(3S*), 2β]]-2-Phenylcyclohexyl 3-[1-[[dim-ethyl(1,1-dimethylethyl)silyl]oxy]methyl]cyclobu-tyl]-3-[(tetrahydro-2H-pyran-2-yl)oxy]propanoate Analogously to Example 1, 460 mg (1.03 mmol) of the compound that is presented according to Example 43 is reacted, and after working-up and purification, 398 mg (0.75 mmol, 73%) of the title compound is isolated as a colorless oil.

$^1$H-NMR (CDCl$_3$) 0.01 (6H), 0.89 (9H), 1.24–1.97 (19H), 2.15–2.27 (3H), 2.66 (1H), 3.12 (1H), 3.50 (2H), 3.58 (1H), 3.98 (1H), 4.52 (1H), 4.87 (1H), 7.09–7.27 (5H) ppm.

EXAMPLE 51

(S)-3-[1-[[[Dimethyl(1,1-dimethylethyl)silyl]oxy]-methyl]cyclobutyl]-3-[(tetrahydro-2H-pyran-2-yl) oxy]propanoic acid 420 mg (3.75 mmol) of potassium-tert-butylate is suspended in 5 ml of diethyl ether. 16 μl of water is added, and it is allowed to stir for 5 more minutes. Then, a solution of 398 mg (0.75 mmol) of the compound, presented according to Example 50, in 5 ml of diethyl ether, is added. It is allowed to stir for 3 more hours. Then, the reaction solution is diluted with water and neutralized with 10% hydrochloric acid. It is extracted with dichloromethane, the organic phase is washed with saturated aqueous sodium chloride solution, dried on sodium sulfate and concentrated by evaporation in a vacuum. Column chromatography of the crude product on silica gel with a mixture that consists of hexane/ethyl acetate yields 112 mg (0.3 mmol).

$^1$H-NMR (CDCl$_3$): δ=0.01 (6H), 0.90 (9H), 1.30–2.25 (10H), 3.12 (1H), 3.50 (2H), 3.58 (1H), 3.98 (1H), 4.45 (1H) ppm.

The reaction product can be converted into the aldehyde analogously to Example 9 after cleavage of the silyl protective group by the oxidation, analogously to Example 10, with an organometallic compound such as, e.g., XMgCHR$^{5a}$R$^{5b}$, brought to reaction with, for example, ethylmagnesium bromide and converted into compounds according to claim 1 by subsequent oxidation of the alcohol mixture that is obtained analogously to Example 11.

If in Example 40 the starting material 1,1' cyclobutane-dicarboxylic acid diethyl ester is replaced by other 2-substituted or 2,2-disubstituted malonic ester derivatives, for example the following compounds can be produced analogously to Examples 9, 10 and 40–51:

| R$^{4a}$ | R$^{4b}$ | R$^{5a}$ | R$^{5b}$ |
|---|---|---|---|
| —(CH$_2$)$_2$— | | H | CH$_3$ |
| —(CH$_2$)$_2$— | | H | CH$_2$—CH$_3$ |
| —(CH$_2$)$_2$— | | H | (CH$_2$)$_2$—CH$_3$ |
| —(CH$_2$)$_2$— | | H | CH$_2$—C$_6$H$_5$ |
| —(CH$_2$)$_2$— | | H | (CH$_2$)$_2$—C$_6$H$_5$ |
| —(CH$_2$)$_2$— | | CH$_3$ | CH$_3$ |
| —(CH$_2$)$_2$— | | CH$_3$ | CH$_2$—CH$_3$ |
| —(CH$_2$)$_3$— | | H | CH$_3$ |
| —(CH$_2$)$_3$— | | H | CH$_2$—CH$_3$ |
| —(CH$_2$)$_3$— | | H | (CH$_2$)$_2$—CH$_3$ |
| —(CH$_2$)$_3$— | | H | CH$_2$—C$_6$H$_5$ |
| —(CH$_2$)$_3$— | | H | (CH$_2$)$_2$—C$_6$H$_5$ |
| —(CH$_2$)$_3$— | | CH$_3$ | CH$_3$ |
| —(CH$_2$)$_3$— | | CH$_3$ | CH$_2$—CH$_3$ |
| —(CH$_2$)$_4$— | | H | CH$_3$ |
| —(CH$_2$)$_4$— | | H | CH$_2$—CH$_3$ |
| —(CH$_2$)$_4$— | | H | (CH$_2$)$_2$—CH$_3$ |
| —(CH$_2$)$_4$— | | H | CH$_2$—C$_6$H$_5$ |
| —(CH$_2$)$_4$— | | H | (CH$_2$)$_2$—C$_6$H$_5$ |
| —(CH$_2$)$_4$— | | CH$_3$ | CH$_3$ |
| —(CH$_2$)$_4$— | | CH$_3$ | CH$_2$—CH$_3$ |
| CH$_3$ | CH$_3$ | H | CH$_3$ |
| CH$_3$ | CH$_3$ | CH$_2$—CH$_3$ | CH$_2$—CH$_3$ |
| CH$_3$ | CH$_3$ | H | (CH$_2$)$_2$—CH$_3$ |
| CH$_3$ | CH$_3$ | H | CH$_2$—C$_6$H$_5$ |
| CH$_3$ | CH$_3$ | H | (CH$_2$)$_2$—C$_6$H$_5$ |
| CH$_2$—CH$_3$ | CH$_2$—CH$_3$ | H | CH$_3$ |
| CH$_2$—CH$_3$ | CH$_2$—CH$_3$ | H | CH$_2$—CH$_3$ |
| CH$_2$—CH$_3$ | CH$_2$—CH$_3$ | H | (CH$_2$)$_2$—CH$_3$ |
| CH$_2$—CH$_3$ | CH$_2$—CH$_3$ | H | CH$_2$—C$_6$H$_5$ |
| CH$_2$—CH$_3$ | CH$_2$—CH$_3$ | H | (CH$_2$)$_2$—C$_6$H$_5$ |
| CH$_3$ | CH$_2$—CH$_3$ | H | CH$_3$ |
| CH$_3$ | CH$_2$—CH$_3$ | H | CH$_2$—CH$_3$ |

-continued

| $R^{4a}$ | $R^{4b}$ | $R^{5a}$ | $R^{5b}$ |
|---|---|---|---|
| $CH_3$ | $CH_2$—$CH_3$ | H | $(CH_2)_2$—$CH_3$ |
| $CH_3$ | $CH_2$—$CH_3$ | H | $CH_2$—$C_6H_5$ |
| $CH_3$ | $CH_2$—$CH_3$ | H | $(CH_2)_2$—$C_6H_5$ |

EXAMPLE 52

(3S)-4,4-Dimethyl-5-oxo-3-(tetrahydropyran-2-yloxy)-pent-1-ene

Analogously to Example 9, 5.0 g (23.3 mmol) of the compound that is presented according to Example 3 is reacted, and after Working-up, 6.1 g of the title compound is isolated as a colorless oil, which is further reacted without purification.

EXAMPLE 53

(3S,5RS)-4,4-Dimethyl-5-hydroxy-3-(tetrahydropyran-2-yloxy)-hept -1-ene

Analogously to Example 10, 6.1 g (maximum 23.3 mmol) of the crude product that is presented according to Example 52 is reacted, and after-working-up and purification, 1.59 g (6.56 mmol, 28%) of the nonpolar diastereomer as well as 1.67 g (6.89 mmol, 30%) of the polar diastereomer are isolated in each case as a colorless oil.

$^1$H-NMR (CDCl$_3$) of nonpolar isomer: δ=0.79 (3H), 0.84 (3H), 1.03 (3H), 1.23–1.62 (6H), 1.62–1.88 (2H), 3.41–3.58 (2H), 3.88–4.01 (2H), 4.08 (1H), 4.47 (1H), 5.20 (1H), 5.29 (1H), 5.78 (1H) ppm.

$^1$H-NMR (CDCl$_3$) of polar isomer: δ=0.78 (3H), 0.93 (3H), 1.01 (3H), 1.38 (1H), 1.47–1.85 (7H), 3.39–3.57 (3H), 3.90 (1H), 4.04 (1H), 4.62 (1H), 5.21 (1H), 5.32 (1H), 5.69 (1H) ppm.

EXAMPLE 54

(3S,5S)-4,4-Dimethyl-3-(tetrahydropyran-2-yloxy)-heptane-1,5-diol and/or (3S,5R)-4,4-dimethyl-3-(tetrahydropyran-2-yloxy)-heptane-1,5-diol Analogously to Example 5, 1.59 g (6.56 mmol) of the nonpolar alcohol that is presented according to Example 53 is reacted, and after working-up, 1.14 g (4.38 mmol, 67%) of the title compound is isolated as a colorless oil.

$^1$H-NMR (CDCl$_3$): δ=0.78 (6H), 1.01 (3H), 1.2.8 (1H), 1.36–1.64 (6H), 1.64–1.93 (4H), 3.41–3.55 (2H), 3.61–3.82 (2H), 3.87 (1H), 3.99 (1H), 4.28° (1H), 4.56 (1H) ppm.

EXAMPLE 55

(3S,5R or 5S)-1-Benzoyloxy-4,4-dimethyl-3-(tetrahydropyran-2-yloxy)-heptan-5-ol

The solution of 1.04 g (3.99 mmol) of the compound, presented according to Example 54, in 20 ml of anhydrous pyridine is mixed under an atmosphere of dry argon with 476 μl of benzoyl chloride, and it is stirred for 16 hours at 23° C. It is poured into a saturated sodium bicarbonate solution, extracted with dichloromethane and dried on sodium sulfate. The residue that is obtained after filtration and removal of the solvent is purified by chromatography on about 300 ml of fine silica gel with a gradient system that consists of n-hexane and ethyl acetate. 785 mg (2.15 mmol, 54%) of the title compound is isolated as a colorless oil as well as 352 mg of starting material.

$^1$H-NMR (CDCl$_3$): δ=0.83 (6H), 1.04 (3H), 1.31 (1H), 1.38–1.58 (5H), 1.74–1.99 (3H), 2.12 (1H), 3.40 (1H), 3.52 (1H), 3.90–4.03 (2H), 4.28–4.56 (4H), 7.45 (2H), 7.58 (1H), 8.05 (2H) ppm.

EXAMPLE 56

(3S)-1-Benzoyloxy-4,4-dimethyl-3-(tetrahydropyran-2-yloxy)heptan-5-one

Analogously to Example 11, 780 mg (2.14 mmol) of the compound that is presented according to Example 55 is reacted, and after working-up and purification, 641 mg (1.77 mmol, 83%) of the title compound is isolated as a colorless oil.

$^1$H-NMR (CDCl$_3$): δ=1.02 (3H), 1.11 (3H), 1.23 (3H), 1.40–1.56 (4H), 1.65–1.87 (3H), 1.93 (1H), 2.59 (2H), 3.36 (1H), 3.80 (1H), 4.13 (1H), 4.32 (1H), 4.45 (1H), 4.53 (1H), 7.45 (2H), 7.58 (1H), 8.05 (2H) ppm.

EXAMPLE 57

(3S)-1-Hydroxy-4,4-dimethyl-3-(tetrahydropyran-2-yloxy)-heptan-5-one

The solution of 636 mg (~1.75 mmol) of the compound, presented according to Example 56, in 25 ml of methanol is mixed with 738 mg of potassium carbonate, and it is stirred for 2 hours at 23° C. It is mixed with dichloromethane, filtered off, washed with water and the organic phase is dried on sodium sulfate. The residue that is obtained after filtration and removal of the solvent is purified by chromatography on about 100 ml of fine silica gel with a gradient system that consists of n-hexane and ethyl acetate. 311 mg (1.20 mmol, 69%) of the title compound is isolated as a colorless oil.

$^1$H-NMR (CDCl$_3$) δ=0.98 (3H), 1.07 (3H), 1.18 (3H), 1.441.90 (10H), 2.00 (1H), 3.50–3.68 (2H), 3.74 (1H), 3.83–4.06 (–2H), 4.79 (1H) ppm.

Production of the Components of General Formula A' with the 2-Oxazolidinone Auxiliary Group (PCT/EP98/05064)

Starting Products

A) 2,2-Dimethyl-3-oxopentanal

Aa) 4-(2-Methylprop-1-enyl)morpholine 43.6 g of morpholine is introduced into a 250 ml three-necked round-bottom flask. 46 ml of isobutylaldehyde is added in drops at a temperature of 5° C. within 20 minutes while being cooled in an ice bath. In this case, a strong temperature increase was to be observed (strong exothermal reaction). After the addition was completed, the batch is refluxed via a water separator for 4 hours. The volume of the water separator is filled with isobutylaldehyde. 7.5 ml of H$_2$O is separated. After the end of the reaction, the reaction mixture is distilled in a vacuum.

Oil bath temperature: 85°–90° C.
Main fraction m=58.37 g 82.03%
Boiling point: 59° C. at 11 mbar
Yield: 58.37 g 82.03% Aa)

A) 2,2-Dimethyl-3-oxopentanal

The solution of 77.14 g of propionic acid chloride in 200 ml of ether p.a. is introduced into a 1000 ml three-necked round-bottom flask. A solution of 117.73 g of the compound, obtained under Aa), in 200 ml of ether p.A. is added in drops within 30 minutes at a reaction temperature of 6° C. while being cooled in an ice bath. Precipitation, white precipitate results. After the addition is completed, the batch is refluxed for 5 hours and then stirred overnight at room temperature. The resulting white precipitate, which is sensitive to moisture, is suctioned off, washed with ether and dried in the oil pump.

Crude product: m=65.26 g of hydrochloride.
In the filtrate, refilling can be observed.
Crude product m=35.49 g Total: m=100.75 g.
100.75 g of hydrochloride is dissolved in 150 ml of $H_2O$. Then, the aqueous phase with $NaHCO_3$ as a whole is set at pH 0.5 and then extracted 4 times with 150 ml of ether each. The organic phase is washed once with brine and then dried on $Na_2SO_4$. The ether is distilled off at normal pressure, and the residue is distilled in a vacuum via a small Vigreux column (6 trays).

Main fraction: m=29.65 g 27.75%
Boiling point: 62° C. at 15 mbar
Yield: 29.65 g 27.75% A)

B) 2,2-Dimethyl-3-oxo-butanal
Execution analogous to A).
Batch: 58.37 g=413.36 mmol of Aa), M=141.21 g/mol
100 ml of diethyl ether p.A.
32.45 g=413.38 mmol of acetyl chloride, M=078.5 g/mol=1.104 g/ml
100 ml of diethyl ether p.A.
stirred over a weekend at room temperature.
Crude product m=72.07 g of hydrochloride
For working-up, see Ab)
oil bath temperature: 75° C. to 80° C.
Main fraction: m=18.75 g 39.74%
Boiling point: 50° C. at 11 mbar
Yield m=18.7 g 39.6% B)

C) 1-(1-Oxopropyl)cyclobutanecarbaldehyde

Ca) 1,1-Cyclobutanedimethanol
170 ml of a 1.2 molar solution of diisobutylaluminum hydride is added in drops at 0° C. to a solution of 20 g (100 mmol) of 1,1-cyclobutanedicarboxylic acid diethyl ester in 200 ml of absolute tetrahydrofuran. It is allowed to stir for one more hour at 0° C., and then 30 ml of water is added. It is filtered on Celite. The filtrate is dried with sodium sulfate and concentrated by evaporation in a vacuum. The crude product that is obtained (9.9 g) is used without purification in the next step.

Cb) 1-[[[Dimethyl(1,1-dimethylethyl)silyl]oxy]methyl]-cyclobutanemethanol
A solution of 9.9 g of Ca) (85 mmol) in 100 ml of absolute tetrahydrofuran is added at 0° C. to a suspension of 3.4 g of sodium hydride (60% in oil, 85 mmol)) in 35 ml of absolute tetrahydrofuran. It is allowed to stir for 30 more minutes, and then a solution of 12.8 g of tert-butyldimethylsilyl chloride (85 mmol) in 50 ml of tetrahydrofuran is added. It is allowed to stir for one more hour at 25° C., and then the reaction mixture is poured onto saturated aqueous sodium bicarbonate solution. It is extracted with ethyl acetate. The organic phase is washed with saturated sodium chloride solution and dried on sodium sulfate. After the solvent is drawn off in a vacuum, the crude product that is obtained is purified by column chromatography on silica gel with a mixture that consists of hexane/ethyl acetate. 13.5 g (69%) of the title compound is obtained.

$^1$H-NMR ($CDCl_3$): δ=0.04 (6H), 0.90 (9H), 1.70–2.00 (6H) 3.70 (4H) ppm.

Cc) 1-[[[Dimethyl(1,1-dimethylethyl)silyl]oxy]methyl]cyclobutane carbaldehyde
8 ml of oxalyl chloride is dissolved in 100 ml of dichloromethane. It is cooled to −78° C., and 13 ml of dimethyl sulfoxide is added. It is allowed to stir for 3 more minutes, and then a solution of 13.5 g of Cb) (58.6 mmol) in 80 ml of dichloromethane is added. After another 15 minutes of stirring time, 58 ml of triethylamine is added in drops. Then, it is allowed to heat to 0° C. Then, the reaction mixture is poured onto saturated sodium bicarbonate solution. It is extracted with dichloromethane, the organic phase is washed with saturated sodium chloride solution, dried on sodium sulfate and concentrated by evaporation in a vacuum. After the crude product is chromatographed on silica gel with a mixture that consists of hexane/ethyl acetate, 7.7 g (58%) of the title compound is obtained.

$^1$H-NMR ($CDCl_3$) δ=0.03 (6H), 0.90 (9H), 1.85–2.00 (4H), 2.20–2.30 (2H), 3.83 (2H), 9.70 (1H) ppm.

Cd) 1-[[Dimethyl(1,1-dimethylethyl)silyl]oxy]methyl]-α-ethylcyclobutanemethanol
A solution of 7.7 g (33.7 mmol) of the compound, described under Cc), in 80 ml of tetrahydrofuran is added in drops at 0° C. to 20 ml of a 2 molar solution of ethylmagnesium chloride (40 mmol) in tetrahydrofuran. It is allowed to stir for 30 more minutes at 0° C., and the reaction mixture is then poured onto saturated ammonium chloride solution. It is extracted with ethyl acetate. The organic phase is washed with saturated sodium chloride solution and dried on sodium sulfate. After the solvent is drawn off, the crude product that is obtained is purified by column chromatography on silica gel. 7.93 g (91.5%) of the title compound is obtained.

$^1$H-NMR ($CDCl_3$): δ=0.09 s (6H), 0.90 s (9H), 1.05 (3H), 1.30–1.50 (3H), 1.70–1.90 (4H), 2.09 (1H), 3.19 (1H), 3.46 (1H), 3.72 (1H), 3.85 (1H) ppm.

Ce) 1-[1-[[[Dimethyl(1,1-dimethylethyl)silyl]oxy]-methyl]-cyclobutyl]-1-propanone
6 ml (85.7 mmol) of dimethyl sulfoxide is added at −78° C. to 3.76 ml (43.8 mmol) of oxalyl chloride in 80 ml of dichloromethane. It is allowed to stir for 3 more minutes, and then absolution of 7.93 g (30.7 mmol) of the compound, described under Cd), in 80 ml of dichloromethane is added. It is stirred for another 15 minutes at −78° C. Then, a mixture that consists of 19 ml (136 mmol) of triethylamine and 40 ml of dichloromethane is added in drops. It is allowed to heat to −25° C. and stirred at this temperature for 30 more minutes. Then, the reaction mixture is poured onto saturated ice-cold sodium bicarbonate solution. It is extracted with dichloromethane. The organic phase is washed with saturated sodium chloride solution and dried on sodium sulfate. After the solvent is drawn off, the crude product that is obtained is filtered on silica gel. 7.87 g (100%) of the title compound is obtained.

$^1$H-NMR ($CDCl_3$): δ=0.05 (6H), 0.88 (9H), 1.04 (3H), 1.82–1.95 (4H), 2.33–2.47 (2H), 2.45–2.54 (2H), 3.81 (2H) ppm.

Cf) 1-[1-(Hydroxymethyl)cyclobut-1-yl]-1-propanone,
7.87 g (30.7 mmol) of the compound that is described under Ce) is dissolved in 100 ml of tetrahydrofuran. 15 ml of a 1 molar solution of tetrabutylammonium fluoride is added, and it is allowed to stir for 12 more hours at 25° C. Then, the reaction mixture is poured onto saturated sodium bicarbonate solution. It is extracted with ethyl acetate. The organic phase is washed with saturated sodium chloride solution and dried on sodium sulfate. After the solvent is drawn off, the crude product that is obtained is purified by column chromatography on silica gel. 3.19 g (73.4%) of the title compound is obtained.

$^1$HNMR (CDCl$_3$): δ=1.07 (3H), 1.86–2.08 (4H), 2.32–2.40 (2H), 2.55–2.65 (2H), 3.88 (2H) ppm.

C) 1-(1-Oxopropyl)cyclobutanecarbaldehyde

Analogously to Example Ce), 3.14 g (100%) of the title compound is obtained by oxidation from 3.19 g (22.4 mmol) of the compound that is described under Cf).

$^1$H-NMR (CDCl$_3$): δ=1.07 (3H), 1.85–2.00 (2H), 2.40–2.53 (6H), 9.70 (1H) ppm.

EXAMPLE 1

(R)-4,4-Dimethyl-3-[3-[[dimethyl(1,1-dimethylethyl) silyl]oxy]-5-oxo-heptanoic acid 0.17 ml of a 30% hydrogen peroxide-solution is added at 0° C. to a solution of 190 mg of the silyl ether, produced according to Example 1c), in 2.5 ml of a mixture that consists of tetrahydrofuran and water at a 4:1 ratio. After 5 minutes of stirring, a solution of 15.8 mg of lithium hydroxide in 0.83 ml of water is then added, and the reaction mixture is stirred for 3 hours at 25° C. Then, it is mixed with a solution of 208 mg of sodium sulfite in 1.24 ml of water and extracted with 10 ml of methylene chloride. The aqueous phase is set at pH=1 with 5N hydrochloric acid and extracted three times with 10 ml of ethyl acetate each. After drying on sodium sulfate and filtration, it is concentrated by evaporation in a vacuum. In addition, the methylene chloride phase above is washed with 5N hydrochloric acid, and then this aqueous phase is extracted three times with 10 ml of acetic acid each. After drying on sodium sulfate and filtration, it is concentrated by evaporation in a vacuum, and an additional amount of crude product is obtained. The combined residues that are thus obtained are purified by chromatography on silica gel. With hexane/0–50% ethyl acetate, 93 mg of the title compound is obtained as a colorless oil in addition to 70 mg of (4R,5S)-4-methyl-5-phenyloxazolidin-2-one. [D]$_D$=+15.5° (CHCl$_3$)

$^1$H-NMR (CDCl$_3$): δ=0.03–0.08 (6H), 0.86 (9H), 1.01 (3H), 1.10 (3H), 1.15 (3H), 2.35 (1H), 2.4–2.7 (3H), 4.48 (1H) ppm.

1a) (4R,5S)-3-(Bromoacetyl)-4-methyl-5-phenyloxazolidin-2-one 117-ml of a 1.6 molar solution of butyllithium in hexane is added within 30 minutes at −70° C. under nitrogen to a solution of 30.1 g of (4R,5S)-4-methyl-5-phenyloxazolidin-2-one in 500 ml of tetrahydrofuran. Then, a solution of 26.8 g of bromoacetyl chloride in 250 ml of tetrahydrofuran is added in drops, so that the temperature does not exceed −65° C. After 1.75 hours of stirring at −70° C., a saturated ammonium chloride solution is added, followed by 60 ml of a saturated sodium bicarbonate solution, and it is allowed to come to 25° C. After the phases are separated, the aqueous phase is extracted twice with 100 ml of ether each. The combined organic phases are washed with semiconcentrated sodium chloride solution, dried on sodium sulfate and concentrated by evaporation in a vacuum after filtration. The residue that is thus obtained is purified by chromatography on silica gel. With hexane/0–50% ether, 34.8 g of the title compound is obtained as a colorless oil.

$^1$H-NMR (CDCl$_3$) δ=0.95 (3H), 4.57 (2H), 4.80 (2H), 5.76 (2H), 7.2–7.5 (5H) ppm.

1b) [4R-[3(R*), 4α, 5α]]-3-[4,4-Dimethyl-1,5-dioxo-3-hydroxyheptyl]-4-methyl-5-phenyl-oxazolidin-2-one 218 mg of lithium iodide is added under argon to a suspension of 5.0 g of anhydrous chromium(II) chloride in 60 ml of tetrahydrofuran. Then, a mixture of 2.09 g of the 2,2-dimethyl-3-oxo-pentanal (see under "Starting Products" Ab) and 5.34 g of previously produced bromine compound in 10 ml of tetrahydrofuran that is known in the literature is added. After 2 hours of reaction time, it is mixed with 30 ml of saturated sodium chloride solution and stirred for 15 minutes. The aqueous phase is extracted three times with 200 ml of ether each. The combined organic phases are washed with semiconcentrated sodium chloride solution, dried on sodium sulfate and concentrated by evaporation in a vacuum after filtration. The residue that is thus obtained is purified by chromatography on silica gel. With hexane/0–30% ethyl acetate, 1.55 g of the title compound is obtained as a colorless oil.

$^1$H-NMR (CDCl$_3$): δ=0.92 (3H), 1.06 (3H), 1.18 (3H), 1.23 (3H), 2.58 (2H), 3.07 (2H), 3.28 (1H), 4.35 (1H), 4.79 (1H), 5.70 (2H), 7.2–7.5 (5H) ppm.

1c) [4R-[3(R*), 4α, 5 α]]-3-[4,4-Dimethyl-3-dimethyl)1,1-dimethylethyl)silyl]oxy]-1,5-dioxoheptyl]-4-methyl-5-phenyloxazolidin-2-one 150 mg of 2,6-lutidine is added under argon at −70° C. to a solution of 347 mg of previously produced alcohol in 3 ml of methylene chloride. After 5 minutes of stirring, 344 mg of tert-butyldimethylsilyltrifluoromethanesulfonate is added, and it is stirred for another 45 minutes at −70° C. It is mixed with 1 ml of saturated-sodium chloride solution and allowed to come to 25° C. Then, it is diluted with ether, and the organic phase is washed with saturated sodium chloride solution. After drying on sodium sulfate and filtration, it is concentrated by evaporation in a vacuum. The residue that is thus obtained is purified by chromatography on silica gel. With hexane/0–30% ethyl acetate, 192 mg of the title compound is obtained as a colorless crystalline compound with a melting point of 111–112° C.

$^1$H-NMR (CDCl$_3$): δ=0.01–0.12 (6H), 0.86 (9H), 0.90 (3H), 1.00 (3H), 1.13 (3H), 1.17 (3H), 0.2.56 (2H), 3.05 (2H), 4.65–4.80 (2H), 5.68 (1H), 7.2–7.5 (5H) ppm.

EXAMPLE 2

(S)-4,4-Dimethyl-3-[3-[[dimethyl(1,1-dimethylethyl) silyl]oxy]-5-oxo-heptanoic acid The compound is produced analogously to Example 1. (4S,5R)-4-Methyl-5-phenyloxazolidin-2-one is used as a starting product. The coverage of NMR is identical to Example 1.

[α]$_D$−−15.7° (CHCl$_3$)

2a) (4S,5R)-3-(Bromoacetyl)-4-methyl-5-phenyloxazolidin-2-one

The production is carried out analogously to Example 1a), starting from (4S,5R)-4-methyl-5-phenyloxazolidin-2-one. The coverage of NMR is identical to 1a).

EXAMPLE 3

(S)-3-[3-[[Dimethyl(1,1-dimethyl)silyl]oxy]-3-[1-(1-oxopropyl)cyclobut-1-yl]Propanoic acid Analogously to Example 1, 1.49 g (80%) of the title compound and 941 mg of recovered (4S,5R)-4-methyl-5-phenyloxazolidin-2-one are obtained from 2.79 g (5.9 mmol) of the compound that is described under 3b). The title compound and the chiral auxiliary group that is to be recovered can be separated by chromatography (analogously to Example 1) or else fractionated crystallization and then optionally purified by chromatography.

$^1$H-NMR (CDCl$_3$): δ=0.09 (3H), 0.19 (3H), 0.90 (9H), 1.08 (3H), 1.70–2.00 (3H), 2.20–2.40 (4H), 2.47 (1H), 2.50–2.70 (2H), 4.45 (1H) ppm.

3a) [4S-[3(R*), 4α,5α]]-3-[3-Hydroxy-1-oxo-3-[1-(1-oxopropyl)cyclobut-1-yl]propyl]-4-methyl-5-phenyloxazolidin-2-one Analogously to Example 1b), 3.0 g (37.4%) of the title compound is obtained as a colorless oil after column chromatography on silica gel from 3.14 g (22.4 mmol) of the compound that is described under C), 9.7 g (78.8 mmol) of anhydrous chromium(II) chloride, 9.69 g (32.5 mmol) of 2a) and 300 mg (2.2 mmol) of anhydrous lithium iodide in tetrahydrofuran.

$^1$H-NMR (CDCl$_3$) δ=0.93 (3H), 1.10 (3H), 1.80–2.03 (2H), 2.10–2.21 (1H), 2.26–2.35 (3H), 2.54–2.70 (2H), 3.03–3.08 (2H), 3.34 (1H), 4.39 (1H), 4.74–4.85 (1H), 5.69 (1H), 7.27–7.34 (2H), 7.36–7.49 (3H) ppm.

3b) [4S-3(R*), 4α, 5α]]-3-[3-[[Dimethyl (1,1-dimethylethyl)silyl]oxy]-1-oxo-3-[1-(1-oxopropyl) cyclobut-1-yl] propyl]-4-methyl-5-phenyloxazolidin-2-one Analogously to Example 1c), 2.79 g (70.6k) of the title compound is obtained from 3.0 g (8.35 mmol) of the compound that is described under Example 3a), tert-butyldimethylsilyl-trifluoromethane sulfonate and 2,6-lutidine after recrystallization from diisopropyl ether.

$^1$H-NMR (CDCl$_3$): δ=0.10 (3H), 0.21 (3H), 0.92 (3H), 0.95 (9H), 1.10 (3H), 1.70–1.92 (2H), 2.02–2.16 (1H), 2.20–2.40 (3H), 2.50–2.72 (2H), 2.98–3.10 (2H) 4.63–4.75 (1H), 5.69 (1H), 7.28–7.35 (2H), 7.36–7.48 (3H) ppm.

EXAMPLE 4

(R)-3-[3-[[Dimethyl(1,1-dimethyl)silyl]oxy]-3-[1-(1-oxopropyl)cyclobut-1-yl]-propanoic acid The compound is produced analogously to Example 3. As a starting product, (4R,5S)-3-(bromoacetyl)-4-methyl-5-phenyloxazolidin-2-one is used.

The coverage of the NMR spectrum is identical to Example 3.

The stereochemistry in 3-position can be controlled by the selection of the stereochemistry at C4 and C5 of the chiral auxiliary group 4-methyl-5-phenyl-2-oxazolidone.

The structure of intermediate product 1b) was documented by an x-ray structural analysis.

Examples of the Production of Component B (DE 197 51 200.3 or PCT/EP98/05064)

EXAMPLE 1

2,2-Trimethylene-4-pentinoic acid ethyl ester

A solution of 77.2 g of diisopropylamine in 270 ml of tetrahydrofuran is added at −15° C. to 0° C. under nitrogen to 473 ml of a 1.6 M solution of butyllithium in hexane, and it is then stirred for 30 minutes. Then, a solution that consists of 85.0 g of cyclobutanecarboxylic acid ethyl ester in 170 ml of tetrahydrofuran is added in drops at −70° C., and after 1.5 hours, a solution of 78.9 g of 3-bromo-1-propine in 190 ml of tetrahydrofuran is added in drops and stirred for another 2.5 hours at −70° C. Then, the reaction mixture is added to 600 ml of saturated ammonium chloride solution and extracted three times with 600 ml of ether each. The combined organic phases are washed three times with 100 ml of semisaturated sodium chloride solution each and dried on sodium sulfate. After filtration, it is concentrated by evaporation in a vacuum, and the residue that is thus obtained is purified by chromatography on silica gel. With hexane/0–10% ether, 65.5 g of the title compound is obtained as a colorless oil.

$^1$H-NMR (CDCl$_3$) δ=1.28 (3H), 1.9–2.3 (5H), 2.47 (2H), 2.64 (2H), 4.20 (2H) ppm.

EXAMPLE 2

2,2-Trimethylene-4-pentin-1-ol 335 ml of a 1.2 M solution of diisobutylaluminum hydride in toluene is added at −70° C. under nitrogen to a solution that consists of 65.4 g of previously produced ester in 950 ml of toluene, and it is stirred for 1.5 hours at this temperature. Then, 30 ml of isopropanol is carefully added, and after 10 minutes, 170 ml of water is added, allowed to come to 22° C. and stirred at this temperature for 2 hours. Precipitate is filtered out, rewashed well with ethyl-acetate, and the filtrate is concentrated by evaporation in a vacuum. The residue that is thus obtained is purified by chromatography on silica gel. With hexane/0–40% ether, 16.5 g of the title compound is obtained as a colorless oil.

$^1$H-NMR (CDCl$_3$) δ=1.75 (6H), 1.98 (1H), 2.42 (2H), 3.67 (2H) ppm.

EXAMPLE 3

1-tert-Butyldimethylsilyloxy-2,2-trimethylene-4-pentine 30.5 g of imidazole, followed by 33.8 g of tert-butyldimethylsilyl chloride, are added at 0° C. under nitrogen to a solution of 18.5 g of previously produced alcohol in 500 ml of dimethylformamide. After 18 hours of stirring at 22° C., it is diluted with 1 l of a 1:1 mixture that consists of hexane and ether, the organic phase is washed twice with water, three times with semisaturated sodium chloride solution and then dried on sodium sulfate. After filtration, it is concentrated by evaporation in a vacuum, and the thus obtained residue is purified by chromatography on silica gel. With hexane/0–10% ether, 35.5 g of the title compound is obtained as a colorless oil.

$^1$H-NMR (CDCl$_3$): δ=0.06 (6H), 0.90 (9H), 1.83 (6H), 1.91 (1H), 2.32 (2H), 3.55 (2H) ppm.

EXAMPLE 4

1-tert-Butyldimethylsilyloxy-2,2-trimethylene-hept-4-in-6-ol 30 ml of a 1.6 M solution of butyllithium in hexane is added at −70° C. under nitrogen to a solution that consists of 11.0 g of previously produced silyl ether in 160 ml of tetrahydrofuran. After 30 minutes of stirring, a solution that consists of 2.3 g of acetaldehyde in 250 ml of tetrahydrofuran is added in drops, stirred for 2 hours at −70° C. and for 2 hours at 0° C. Then the reaction mixture is added to 150 ml of saturated ammonium chloride solution and extracted three times with 300 ml of ether each. The combined organic phases are washed twice with 100 ml of semisaturated sodium chloride solution each and dried on sodium sulfate. After filtration, it is concentrated by evaporation in a vacuum, and the residue that is thus obtained is purified by chromatography on silica gel. With hexane/0–30% ether, 9.9 g of the title compound is obtained as a colorless oil.

$^1$H-NMR (CDCl$_3$): δ=0.07 (6H), 0.90 (9H), 1.45 (3H), 1.7–1.9 (m, 6H), 2.34 (2H), 3.53 (2H)I, 4.53 (1H) ppm.

EXAMPLE 5

1-tert-Butyldimethylsilyloxy-2,2-trimethylene-6-(tetrahydro-2H -pyran-2yloxy)-hept-4-ine 4.33 g of dihydropyran, followed by 185 mg of p-toluenesulfonic acid-monohydrate, is added at 0° C. under nitrogen to 12.0 g of previously produced alcohol in 310 ml of methylene chloride. After 2.5 hours of stirring at 0° C., it is mixed with 3 ml of triethylamine and after 10 minutes, the reaction mixture is diluted with 500 ml of methylene chloride. The organic phase is washed once with 50 ml of saturated sodium bicarbonate solution, three times with 50 ml of semisaturated sodium chloride-solution each and dried on sodium sulfate. After filtration, it is concentrated by evaporation in a vacuum, and the residue that is thus obtained is purified by chromatography on silica gel. With hexane/0–5% ether, 14.6 g of the title compound is obtained as a colorless oil.

$^1$H-NMR (CDCl$_3$): δ=0.0–0.1 (6H), 0.9–1.0 (9H), 1.43 (3H), 1.4–1.9 (m, 12H), 2.32 (2H), 3.52 (2H), 3.4–3.6 (1H), 3.84/3.98 (1H), 4.4–4.6 (1H), 4.80/4.94 (1H) ppm.

EXAMPLE 6

1-tert-Butyldimethylsilyloxy-2,2-trimethylene-6-(tetrahydro-2H -pyran-2-yloxy)-heptane A solution of 650 mg of the THP-ether, produced in Example 5, in 20 ml of ethyl acetate is mixed with 65 mg of 10% palladium on carbon and stirred for 18 hours at 22° C. in a hydrogen atmosphere. Then, catalyst is filtered out, rewashed well with ethyl acetate, and the filtrate is concentrated by evaporation in a vacuum. The residue that is thus obtained is purified by chromatography on silica gel. With hexane/0–5% ether, 594 mg of the title compound is obtained as a colorless oil.

$^1$H-NMR (CDCl$_3$): δ=0.0–0.1 (6H), 0.9 (9H), 1.23 (3H), 1.1–1.9 (18H), 3.45 (2H), 3.4–3.6 (1H), 3.6–4.00 (2H), 4.64/4.73 (1H) ppm.

EXAMPLE 7

4-tert-Butyldimethylsilyloxy-but-2-in-1-ol

A solution of 175 g of tert-butyldimethylsilyl chloride in 100 ml of a 1:1 mixture that consists of hexane and dimethylformamide is slowly added in drops at 0° C. under nitrogen to a solution of 100 g of 2-butin-1-ol and 158 g of imidazole in 300 ml of dimethylformamide, and it is stirred for 2 hours at 0° C. and for 16 hours at 22° C. The reaction mixture is diluted with 2.5 l of ether, washed once with water, once with 5% sulfuric acid, once with water, once with saturated sodium bicarbonate solution and washed neutral with semi-saturated sodium chloride solution. After drying on sodium sulfate and filtration, it is concentrated by evaporation in a vacuum. The residue that is thus obtained is purified by chromatography on silica gel. With hexane/0–40% ether, 74.3 g of the title compound is obtained as a colorless oil.

IR (film): 3357, 2929, 2858, 1472, 1362, 1255, 1132, 1083, 1015, 837, 778 cm$^{-1}$.

EXAMPLE 8

(4R,5S,2'S)-4-Methyl-5-phenyl-3-[1-oxo-2-methyl-6-(tert -butyldimethylsilyloxy)-hex-4-in-1-yl]-2-oxazolidinone 11.3 ml of lutidine is added under nitrogen to 21 g of a solution of previously produced silyl ether in 125 ml of toluene. Then, it is cooled to −40° C., and 17.7 ml of trifluoromethanesulfonic acid anhydride is added in drops at this temperature. Then, it is diluted with 100 ml of hexane and stirred for 10 minutes. Under nitrogen via a reversing frit, this solution is added to a solution that was produced from 17.8 g of hexamethyldisilazane in 140 ml of tetrahydrofuran with 73.5 ml of a 1.6 M solution of butyllithium in hexane at −60° C. (10 more minutes of stirring-time) and 23.3 g of (4R,5S)-4-methyl-5-phenyl-3-propionyl-2-oxazolidinone in 62 ml of tetrahydrofuran (30 more minutes of stirring time). It is allowed to stir for one more hour at −60° C., then mixed with 6 ml of acetic acid in 5 ml of tetrahydrofuran, and the reaction mixture is allowed to heat to 22° C. It is added to 80 ml of water and extracted three times with ether. The combined organic phases are washed twice with saturated sodium chloride solution and dried on sodium sulfate. After filtration, it is concentrated by evaporation in a vacuum. The residue that, is thus obtained is purified by chromatography on silica gel. With hexane/0–20% ether, 16.0 g of the title compound is obtained as a colorless oil.

$^1$H-NMR (CDCl$_3$) δ=0.10 (6H), 0.90 (9H), 0.92 (3H), 1.28 (3H), 2.47 (1H), 2.61 (1H), 3.96 (1H), 4.26 (2H), 4.78 (1H), 5.68 (1H), 7.31 (1H), 7.3–7.5 (3H) ppm.

EXAMPLE 9

(2S)-2-Methyl-6-(tert-butyldimethylsilyloxy)-4-hexinoic acid ethyl ester 9.0 ml of titanium(IV)ethylate is added under nitrogen to a solution of 39.3 g of the previously produced alkylating product in 120 ml of ethanol, and it is refluxed for 4 hours. The reaction mixture is concentrated by evaporation in a vacuum, and the residue is dissolved in 100 ml of ethyl acetate. 3 ml of water is added, stirred for 20 minutes, precipitate is suctioned out, and it is rewashed well with ethyl acetate. The filtrate is concentrated by evaporation, mixed with 200 ml of hexane, and precipitate is filtered out. The precipitate is washed well with hexane. The filtrate is concentrated by evaporation in a vacuum, and the residue that is thus obtained is purified by chromatography on silica gel. With hexane/0–20% ether, 25.4 g of the title compound is obtained as a colorless oil.

$^1$H-NMR (CD$_2$Cl$_2$): δ=0.10 (3H), 0.90 (9H), 1.2–1.3 (6H), 2.37 (1H), 2.54 (1H), 2.60 (1H), 4.12 (2H), 4.27 (2H) ppm.

EXAMPLE 10

(2S)-2-Methyl-6-(tert-butyldimethylsilyloxy)-hexanoic acid ethyl ester

A solution of 10.5 g of the previously produced ester in 200 ml of ethyl acetate is mixed with 1 g of 10% palladium on carbon, and it is stirred for 3 hours at 22° C. in a hydrogen atmosphere. Then, catalyst is filtered out, it is rewashed well with ethyl acetate, and the filtrate is concentrated by evaporation in a vacuum. The residue that is thus obtained is purified by chromatography on silica gel. With hexane/0–10% ether, 9.95 g of the title compound is obtained as a colorless oil.

$^1$H-NMR (CD$_2$Cl$_2$): δ=0.01 (6H), 0.84 (9H), 1.07 (3H), 1.18 (3H), 1.2–1.7 (6H), 2.38 (1H), 3.57 (2H), 4.05 (2H) ppm.

EXAMPLE 11

(2S)-2-Methyl-6-(tert-butyldimethylsilyloxy)-hexan-1-ol 63 ml of a 1.2 M solution of diisobutylaluminum hydride in toluene is added at −40° C. under nitrogen to a solution that consists of 9.94 g of the previously produced ester in 130 ml of toluene, and it is stirred for 1 hour at this temperature. Then, 15 ml of isopropanol is carefully added, and after 10 minutes, 30 ml of water is added, allowed to reach 22° C., and it is stirred at this temperature for 2 hours. Precipitate is filtered out, it is rewashed well with ethyl acetate, and the filtrate is concentrated by evaporation in a vacuum. The residue that is thus obtained is purified by chromatography on silica gel. With hexane/0–30% ether, 7.9 g of the title compound is obtained as a colorless oil. [α]$_D$ −8.1° (c=0.97, CHCl$_3$)

$^1$H-NMR (CDCl$_3$): δ=0.07 (3H), 0.89 (9H), 0.91 (3H), 1.0–1.7 (7H), 3.48 (2H), 3.52 (2H) ppm.

EXAMPLE 12

(2S)-2-Methyl-6-(tert-butyldimethylsilyloxy)-1-(tetrahydro-2H-pyran-2-yloxy)-hexane 3.52 ml of dihydropyran, followed by 49 mg of p-toluenesulfonic acid-monohydrate, is added at 0° C. under argon to 6.4 g of the previously produced alcohol in 26 ml of methylene chloride. After 1.5 hours of stirring at 0° C., it is mixed with 10 ml of saturated sodium bicarbonate solution and diluted with ether. The organic phase is washed twice with semi-saturated sodium chloride solution and dried on sodium sulfate. After filtration, it is concentrated by evaporation in a vacuum, and the residue that is thus obtained is purified by chromatography on silica gel. With hexane/0–5% ether, 4.75 g of the title compound is obtained as a colorless oil.

$^1$H-NMR (CDCl$_3$) δ=0.05 (6H), 0.89 (9H), 0.92 (3H), 1.0–1.9 (13H), 3.19 (1H), 3.50 (1H), 3.55–3.65 (3H), 4.87 (1H), 4.57 (1H) ppm.

EXAMPLE 13

(5S)-5-Methyl-6-(tetrahydro-2H-pyran-2-yloxy)-hexan-1-ol 13.5 g of tetrabutylammonium fluoride trihydrate is added under nitrogen to a solution of 4.7 g of the previously produced THP-ether in 170 ml of tetrahydrofuran, and it is stirred for 3 hours. Then, the reaction mixture is diluted with 800 ml of ether, and it is washed three times each with 20 ml of semisaturated sodium chloride solution and dried on sodium sulfate. After filtration, it is concentrated by evaporation in a vacuum, and the residue that is thus obtained is purified by chromatography on silica gel. With hexane/0–50% ethyl acetate, 2.88 g of the title compound is obtained as a colorless oil.

$^1$H-NMR (CD$_2$Cl$_2$): δ=0.90/0.92 (3H), 1.1–1.9 (13H), 3.18 (1H), 3.40–3.65 (4H), 3.82 (1H), 4.53 (1H) ppm.

EXAMPLE 14

(5S)-5-Methyl-6-(tetrahydro-2H-pyran-2-yloxy)-hexanal 1.9 ml of dimethyl sulfoxide, dissolved in 7 ml of methylene chloride, is carefully added in drops under nitrogen at −70° C. to 1.08 ml of oxalyl chloride, dissolved in 10 ml of methylene chloride, and it is stirred for 10 minutes at this temperature. Then, a solution of 2.0 g of the previously produced alcohol in 7 ml of methylene chloride is added in drops, and it is stirred for 2 hours between −60° C. and −70° C. Then, 3.86 ml of triethylamine is added, and after 1 hour of stirring at −60° C., the reaction mixture is added to 30 ml of water. After phase separation, the aqueous phase is extracted twice with 30 ml of methylene chloride each. The combined organic phases are washed three times with saturated sodium chloride solution. After drying on sodium sulfate and filtration, it is concentrated by evaporation in a vacuums, 1.99 g of the aldehyde, which is used without further purification, is obtained.

EXAMPLE 15

(2RS,6S)-6-Methyl-7-(tetrahydro-2H-pyran-2-yloxy)-heptan-2-ol 6.16 ml of a 3 M methylmagnesium bromide solution in ether is slowly added in drops under nitrogen at 0° C. to a solution of 1.98 g of the previously produced aldehyde in 30 ml of ether. After 60 minutes, it is slowly poured onto 50 ml of ice-cold saturated ammonium chloride solution and extracted three times with ether. The combined organic phases are washed once with water, and twice with saturated sodium chloride solution and dried on sodium sulfate. After filtration, it is concentrated by evaporation in a vacuum, and the residue that is thus obtained is purified by chromatography on silica gel. With hexane/0–60% ether, 1.57 g of the title compound is obtained as a colorless oil.

$^1$H-NMR (CD$_2$Cl$_2$): δ=0.90/6.93 (3H), 1.15 (3H), 1.0–1.9 (13H), 3.18 (1H), 3.4–3.6 (2H), 3.7–3.9 (2H), 4.53 (1H) ppm.

EXAMPLE 16

(6S)-6-Methyl-7-(tetrahydro-2H-pyran-2-yloxy)-heptan-2-one 163 mg of activated molecular sieve (4 Å, powder) and 533 mg of N-methylmorpholine-N-oxide are added under argon to a solution of 700 mg of the alcohol, produced in Example 15, in a mixture that consists of 14 ml of methylene chloride and 4.7 ml of acetonitrile, stirred for 10 minutes, and then 10.5 mg of tetrapropylammonium perruthenate is added. The reaction mixture is concentrated by evaporation in a vacuum after 20 hours. The residue that is thus obtained is purified by chromatography on silica gel. With hexane/0–40% ether, 690 mg of the title compound is obtained as a colorless oil.

$^1$H-NMR (CDCl$_3$) δ=0.91/0.93 (3H), 1.0–1.9 (11H), 2.13 (3H), 2.42 (2H), 3.19 (1H), 3.4–3.6 (2H), 3.85 (1H), 4.55 (1H) ppm.

EXAMPLE 17

(2S,6RS)-2-Methyl-6-(tert-butyl-diphenylsilyloxy)-1-(tetrahydro-2H-pyran-2-yloxy)-heptane 2.13 ml of tert-butyldiphenylsilyl chloride is added at 0° C. under nitrogen to a solution of 1.57 g of alcohol that is produced according to Example 15, and 1.11 g of imidazole in 20 ml of dimethylformamide, and it is stirred for 15 minutes at 0° C. and for 16 hours at 22° C. The reaction mixture is diluted with 200 ml of ether, washed once with water, once with 10% sulfuric acid, once with saturated sodium bicarbonate solution and washed neutral with saturated sodium chloride solution. After drying on sodium sulfate and filtration, it is concentrated by evaporation in a vacuum. The residue that is thus obtained is purified by chromatography on silica gel. With hexane/0–10% ether, 2.87 g of the title compound is obtained as a colorless oil.

$^1$H-NMR (CDCl$_3$) δ=0.87/0.89 (3H), 1.04 (9H), 0.9–1.9 (16H), 3.15 (1H), 3.4–3.6 (2H), 3.8–3.9 (2H), 4.56 (1H), 7.3–7.5 (6H), 7.69 (4H) ppm.

EXAMPLE 18

(2S,6RS)-2-Methyl-6-(tert-butyl-diphenylsilyloxy)-heptan-1-ol 131 mg of pyridinium-p-toluenesulfonate is added to a solution of 2.3 g of silyl ether, produced according to Example 17, in 100 ml of ethanol, and it is stirred for 4 hours at 40° C. Then, it is concentrated by evaporation in a vacuum, and the residue that is thus obtained is purified by chromatography on silica gel. With hexane/20% ether, 1.68 g of the title compound is obtained as a colorless oil.

EXAMPLE 19

(2S)-2-Methyl-6-(tert-butyldimethylsilyloxy)-hexanal 2.07 g of the alcohol that is produced under Example 11 is oxidized analogously to Example 14, and after working-up and chromatographic purification, 2.09 g of the title compound is isolated as a colorless oil.

$^1$H-NMR (CDCl$_3$): δ=0.04 (6H), 0.90 (9H), 1.10 (3H), 1.31–1.48 (3H), 1.48–1.60 (2H), 1.72 (1H), 2.34 (1H), 3.61 (2H), 9.62 (1H) ppm.

EXAMPLE 20

(2S,6RS)-2-Methyl-6-(tert-butyl-diphenylsilyloxy)-heptanal 2.13 g of the alcohol that is presented under Example 18 is oxidized analogously to Example 14, and after working-up and chromatographic purification, 2.10 g of the title compound is isolated as a colorless oil.

$^1$H-NMR (CDCl$_3$): δ=1.00–1.12 (15H), 1.18–1.63 (6H), 2.22 (1H), 3.83 (1H), 7.32–7.47 (6H), 7.61–7.72 (4H), 9.54 (1H) ppm.

Examples of the Production of Component C (DE 197 51 200.3 or PCT/EP98/05064)

EXAMPLE 1

(S)-Dihydro-3-hydroxy-2 (3H)-furanone 10 g of L-(−)-malic acid is stirred in 45 ml of trifluoroacetic acid anhydride for 2 hours at 25° C. Then, it is concentrated by evaporation in a vacuum, 7 ml of methanol is added to the residue, and it is allowed to stir for 12 more hours. Then, it is concentrated by evaporation in a vacuum. The residue that is obtained is dissolved in 150 ml of absolute tetrahydrofuran. It is cooled to 0° C., and 150 ml of borane-tetrahydrofuran complex is added and allowed to stir for 2.5 more hours at 0° C. Then, 150 ml of methanol is added. It is allowed to stir for one more hour at room temperature and then concentrated by evaporation in a vacuum. The crude product that is obtained is dissolved in 80 ml of toluene. 5 g of Dowex$^{(R)}$ (activated, acidic) is added, and it is refluxed for one hour. Then, Dowex$^{(R)}$ is filtered off, and the filtrate is concentrated by evaporation in a vacuum. The crude product that is obtained (7.61 g, 99.9%) is used without purification in the next step.

EXAMPLE 2

(S)-Dihydro-3-[[(1,1-dimethylethyl)diphenylsilyl]oxy]-2 (3H)-furanone 24 ml of tert-butyldiphenylsilyl chloride is added to a solution of 7.61 g of the substance that is described under Example 1 and 10 g of imidazole in 100 ml of N,N-dimethylformamide. It is allowed to stir for two more hours at 25° C., and then the reaction mixture is poured onto ice-cold saturated sodium bicarbonate solution. It is extracted with ethyl acetate, the organic phase is washed with saturated sodium chloride solution, dried on sodium sulfate and concentrated by evaporation in a vacuum. After column chromatography of the crude product on silica gel with a mixture that consists of hexane/ethyl acetate, 13.4 g (52.8%) of the title compound is obtained.

$^1$H-NMR (CDCl$_3$) δ=7.72 (2H), 7.70 (2H), 7.40–7.50 (6H), 4.30–4.42 (2H), 4.01 (1H), 2.10–2.30 (2H), 1.11 (9H) ppm.

EXAMPLE 3

(2RS,3S)-3-[[(1,1-Dimethylethyl)diphenylsilyl]oxy]tetrahydro-2-furanol 80 ml of a 1 molar solution of diisobutylaluminum hydride in hexane is added at: −78° C. to a solution of 13.4 g of the substance, described under Example 2, in 150 ml of absolute tetrahydrofuran. It is stirred for 45 more minutes at −78° C. and then quenched with water. It is extracted with ethyl acetate, the organic phase is washed with saturated sodium chloride solution, dried on sodium sulfate and concentrated by evaporation in a vacuum. 13.46 g (99.4%) of the title compound, which is used without purification in the next step, is obtained.

EXAMPLE 4

(2RS,3S)-3-[[(1,1-Dimethylethyl)diphenylsilyl]oxy]-1,4-pentanediol

A solution of 13.46 g of the substance, described under Example 3, in 150 ml of absolute tetrahydrofuran is added in drops at 0° C. to 20 ml of a 3 molar solution of methylmagnesium chloride in tetrahydrofuran. It is allowed to stir for one more hour at 0° C. and then poured onto saturated aqueous ammonium chloride solution. It is extracted with ethyl acetate, the organic phase is washed with saturated sodium chloride solution, dried on sodium sulfate and concentrated by evaporation in a vacuum. After column chromatography of the crude product on silica gel with a mixture that consists of hexane/ethyl acetate, 11.42 g (81.6-%) of the title compound is obtained.

$^1$H-NMR (CDCl$_3$): δ=7.65–7.75 (4H), 7.40–7.55 (6H), 5.20 (1H), 4.30 (2H), 3.70 (1H), 1.80 (2H), 1.05 (9H) ppm.

EXAMPLE 5

(2RS, 3S)-5-[[Dimethyl(1,1-dimethylethyl)silyl]oxy]-3-[[1,1-dimethylethyl)diphenylsilyl]oxy]-2-pentanol 4.9 g of tert-butyldimethylsilyl chloride is added to a solution of 11.42 g of the substance that is described under Example 4, and 3.25 g of 1H-imidazole in 120 ml of N,N-dimethylformamide. It is allowed to stir for 2 more hours at 25° C., and then the reaction mixture is poured onto ice-cold, saturated sodium bicarbonate solution. It is extracted with ethyl acetate, the organic phase is washed with saturated sodium chloride solution, dried on sodium sulfate and concentrated by evaporation in a vacuum. After column chromatography of the crude product on silica gel with a mixture that consists of hexane/ethyl acetate, 10.64 g (70.5%) of the title compound is obtained.

$^1$H-NMR (CDCl$_3$): δ=7.60–7.70 (4H), 7.30–7.45 (6H), 3.70–3.80 (2H), 3.40 (1H), 3.00*(1H), 1.80 (1H), 1.60 (1H), 1.05–1.12 (12H), 0.82 (9H), 0.02 (6H) ppm.

EXAMPLE 6

(3S)-5-[[Dimethyl(1,1-dimethylethyl)silyl]oxy]-3-[[(1,1-dimethylethyl)diphenylsilyl]oxy]-2-pentanone 13 ml of dimethyl sulfoxide is added at −78° C. to 7.37 ml of oxalyl chloride in 80 ml of dichloromethane. It is allowed to stir for 3 more minutes, and then 10.46 g of the substance, described under Example 5, in 100 ml of dichloromethane, is added. After another 15 minutes of stirring time, 52 ml of triethylamine is added in drops. Then, it is allowed to heat to 0° C. Then, the reaction mixture is poured onto saturated sodium bicarbonate solution. It is extracted with dichloromethane, the organic phase is washed with saturated sodium chloride solution, dried on sodium sulfate and concentrated by evaporation in a vacuum. After column chromatography of the crude product on silica gel with a mixture that consists of hexane/ethyl acetate, 9.3 g (26.5% relative to the malic acid that is used) of the title compound is obtained.

$^1$H-NMR (CDCl$_3$) δ=7.60–7.70 (4H), 7.32–7.50 (6H), 4.25 (1H), 3.72 (1H), 3.58 (1H), 2.05 (3H), 1.90 (1H), 1.75 (1H), 1.13 (9H), 0.89 (9H), 0.01 (6H) ppm.

EXAMPLE 7

(R)-Dihydro-3-hydroxy-2 (3H)-furanone 10 g of D-(+)-malic acid is reacted analogously to Example 1. 7.26 goof the title compound is obtained. The coverage of the $^1$H-NMR spectrum is identical to 1.

EXAMPLE 8

(R)-Dihydro-3-[[(1,1-dimethylethyl)diphenylsilyl]oxy]-2 (3H)-furanone

Analogously to Example 2, 12.9 g of the title compound is obtained from 7.26 g of the substance that is described under Example 7. The coverage of the $^1$H-NMR spectrum is identical to 2.

EXAMPLE 9

(2RS,3R)-3-[[(1,1-Dimethylethyl)diphenylsilyl]oxy]tetrahydro-2-furanol

Analogously to Example 3, 12.95 g of the title compound is obtained from 12.9 g of the substance that is described under Example 8. The coverage of the $^1$H-NMR spectrum is identical to 3.

EXAMPLE 10

(2RS,3R)-3-[[(1,1-Dimethylethyl)diphenylsilyl]oxy]-1,4-pentanediol

Analogously to Example 4, 11 g of the title compound is obtained from 12.95 g of the substance that is described under Example 9. The coverage of the $^1$H-NMR spectrum is identical to 4.

EXAMPLE 11

(2RS,3R)-5-[[Dimethyl(1,1-dimethylethyl)silyl]oxy]-3-[[(1,1-dimethylethyl)diphenylsilyl]oxy]-2-pentanol Analogously to Example 5, 10.11 g of the title compound is obtained from 11 g of the substance that is described under Example 10. The coverage of the $^1$H-NMR spectrum is identical to 5.

EXAMPLE 12

(R)-5-[[Dimethyl(1,1-dimethylethyl)silyl]oxy]-3-[[(1,1-dimethylethyl)diphenylsilyl]oxy]-2-pentanone Analogously to Example 6, 8.85 g of the title compound is obtained from 10.11 g of the substance that is described under Example 11. The coverage of the $^1$H-NMR spectrum is identical to 6.

EXAMPLE 13

(3RS)-Dihydro-3-hydroxy-2 (3H)-furanone 5 g of racemic malic acid is reacted analogously to Example 1. 3.68 g of the title compound is obtained. The coverage of the $^1$H-NMR spectrum is identical to 1.

EXAMPLE 14

(3RS)-Dihydro-3-[[(1,1-dimethylethyl)diphenylsilyl]oxy]-2(3H)-furanone

Analogously to Example 2, 6.5 g of the title compound is obtained from 3.68 g of the substance that is described under Example 13. The coverage of the $^1$H-NMR spectrum is identical to 2.

EXAMPLE 15

(2RS,3RS)-3-[[1,1-Dimethylethyl)diphenylsilyl]oxy]tetrahydro-2-furanol

Analogously to Example 3, 6.51 g of the title compound is obtained from 6.5 g of the substance that is described under Example 14. The coverage of the $^1$H-NMR spectrum is identical to 15.

EXAMPLE 16

(2RS,3RS)-3-[[(1,1-Dimethylethyl)diphenylsilyl]oxy]-1,4-pentanediol

Analogously to Example 4, 5.5 g of the title compound is obtained from 6.51 g of the substance that is described under Example 15. The coverage of the $^1$H-NMR spectrum is identical to 4.

EXAMPLE 17

(2RS,3RS)-5-([Dimethyl(1,1-dimethylethyl)silyl]oxy]-3-[[(1,1-dimethylethyl)diphenylsilyl]oxy]-2-pentanol Analogously to Example 5, 5.05 g of the title compound is obtained from 5.5 g of the substance that is described under Example 16. The coverage of the $^1$H-NMR spectrum is identical to 5.

EXAMPLE 18

(3RS)-5-[[Dimethyl(1,1-dimethylethyl)silyl]oxy]-3-[[(1,1-dimethylethyl)diphenylsilyl]oxy]-2-pentanone Analogously to Example 6, 4.3 g of the title compound is obtained from 5.05 g of the substance that is described under Example 17. The coverage of the $^1$H-NMR spectrum is identical to 6.

EXAMPLE 19

(E,3S)-1-[[Dimethyl(1,1-dimethylethyl)silyl]oxy]-3-[[(1,1-dimethylethyl)diphenylsilyl]oxy]-4-methyl-5-(2-methylthiazol-4-yl)-pent-4-ene The solution of 6.82 g of diethyl(2-methylthiazol-4-yl)methanephosphonate in 300 ml of anhydrous tetrahydrofuran is cooled under an atmosphere of dry argon to −5° C., mixed with 16.2 ml of a 1.6 molar solution of n-butyllithium in n-hexane, allowed to heat to 23° C. and stirred for 2 hours. Then, it is cooled to −78° C., the solution of 6.44 g (13.68 mmol) of the compound, presented according to Example 6, in 150 ml of tetrahydrofuran is added in drops, allowed to heat to 23° C. and stirred for 16 hours. It is poured into saturated ammonium chloride solution, extracted several times with ethyl acetate, the combined organic extracts are washed with saturated sodium chloride solution and dried on sodium sulfate. The residue that is obtained after filtration and removal of the solvent is purified by chromatography on fine silica gel with a gradient system that consists of n-hexane and ethyl acetate. 6.46 g (11.4 mmol, 83%; yield relative to the malic acid that is used: 22%) of the title compound is isolated as a colorless oil.

$^1$H-NMR (CDCl$_3$): δ=−0.04 (6H), 0.83 (9H), 1.10 (9H), 1.79 (1H), 1.90 (1H), 1.97 (3H), 2.51 (3H), 3.51 (2H), 4.38 (1H), 6.22 (1H), 6.74 (1H), 7.23–7.47 (6H), 7.63 (2H), 7.70 (2H) ppm.

EXAMPLE 20

(E,3S)-3-[(1,1-Dimethylethyl)diphenylsilyl]oxy]-4-methyl-5-(2-methylthiazol-4-yl)-pent-4-en-1-ol The solution of 4.79 g (8.46 mmol) of the compound, presented according to Example 19, in 48 ml of tetrahydrofuran is mixed with 48 ml of a 65:35:10 mixture that consists of glacial acetic acid/water/tetrahydrofuran, and it is stirred for 2.5 days at 23° C. It is poured into saturated sodium carbonate solution, extracted several times with ethyl acetate, the combined organic extracts are washed with saturated sodium chloride solution and dried on sodium sulfate. The residue that is obtained after filtration and removal of the solvent is purified by chromatography on fine silica gel with a gradient system that consists of n-hexane and ethyl acetate. 3.42 g (7.57 mmol, 90%) of the title compound is isolated as a colorless oil.

$^1$H-NMR (CDCl$_3$): δ=1.10 (9H), 1.53 (1H), 1.81 (2H), 1.96 (3H), 2.71 (3H), 3.59 (2H), 4.41 (1H), 6.38 (1H), 6.78 (1H), 7.26–7.49 (6H), 7.65 (2H), 7.72 (2H) ppm.

EXAMPLE 21

(E,3S)-1-Bromo-3-[[(1,1-dimethylethyl)diphenylsilyl]oxy]-4-methyl-5-(2-methylthiazol-4-yl)-pent-4-ene The solution of 378 mg (0.84 mmol) of the compound, presented according to Example 20, in 9 ml of dichloromethane is mixed at 0° C. under an atmosphere of dry argon with 90 μl of pyridine, 439 mg of triphenylphosphine, and 556 mg of tetrabromomethane, and it is stirred for 1 hour at 0° C. The solution is chromatographed on fine silica gel with a gradient system that consists of n-hexane and ethyl acetate. 362 mg (0.70 mmol, 84%) of the title compound is isolated as a colorless oil.

$^1$H-NMR (CDCl$_3$): δ=1.09 (9H), 1.95 (3H), 2.01–2.23 (2H), 2.71 (3H), 3.15–3.35 (2H), 4.35 (1H), 6.30 (1H), 6.79 (1H), 7.25–7.49 (6H), 7.63 (2H), 7.69 (2H) ppm.

EXAMPLE 22

(E,3S)-1-Iodo-3-[[(1,1-dimethylethyl)diphenylsilyl]oxy]-4-methyl-5-(2-methylthiazol-4-yl)-pent-4-ene The solution of 8.41 g of triphenylphosphine in 120 ml of dichloromethane is mixed at 23° C. under an atmosphere of dry argon with 2.19 g of imidazole and 8.14 g of iodine, the solution of 12.2 g (27.0 mmol) of the compound, presented according to Example 20, in 30 ml of dichloromethane is added in drops and stirred for 0.5 hour. The solution is chromatographed on fine silica gel with a gradient system that consists of n-hexane and ethyl acetate. 12.15 g (21.6 mmol, 80%) of the title compound is isolated as a colorless oil.

¹H-NMR (CDCl₃): δ=1.08 (9H), 1.96 (3H), 2.10 (2H), 2.70 (3H), 2.87–3.08 (2H), 4.24 (1H), 6.32 (1H), 6.79 (1H), 7.28–7.48 (6H), 7.60–7.72 (4H) ppm.

EXAMPLE 23

(4E,3S)-[3-[[(1,1-Dimethylethyl)diphenylsilyl]oxy]-4-methyl-5-(2-methylthiazol-4-yl)-pent-4-en-1-yl]-triphenylphosphonium iodide The suspension that consists of 12.55 g (22.3 mmol) of the compound that is presented according to Example 22, 85 g of triphenylphosphine and 11.6 ml of N-ethyldiisopropylamine is stirred under an atmosphere of dry argon for 16 hours at 80° C. After cooling, it is mixed with diethyl ether, filtered, and the residue is rewashed several times with diethyl ether and recrystallized from ethyl acetate. 15.7 g (19.1 mmol, 74%) of the title compound is isolated as a crystalline solid.

¹H-NMR (CDCl₃): δ=1.07 (9H), 1.68–1.92 (2H), 1.98 (3H), 2.70 (3H), 2.93 (1H), 3.30 (1H), 4.53 (1H), 6.62 (1H), 7.03 (1H), 7.23–7.47 (6H), 7.48–7.72 (16H), 7.73–7.85 (3H) ppm.

EXAMPLE 24

(E,3R)-1-[[Dimethyl(1,1-dimethylethyl)silyl]oxy]-3-[[(1,1-dimethylethyl)diphenylsilyl]oxy]-4-methyl-5-(2-methylthiazol-4-yl)-pent-4-ene Analogously to Example 19, 8.56 g (80%) of the title compound is obtained from 8.85 g of the compound that is described under Example 12. The coverage of ¹H-NMR is identical to 19.

EXAMPLE 25

(E,3R)-3-[[(1,1-Dimethylethyl)diphenylsilyl]oxy]-4-methyl-5-(2-methylthiazol-4-yl)-pent-4-en-1-ol Analogously to Example 20, 6.25 g (92%) of the title compound is obtained from 8.56 g of the compound that is described under Example 24. The coverage of ¹H-NMR is identical to 20.

EXAMPLE 26

(E,3R)-1-Iodo-3-[[(1,1-dimethylethyl)diphenylsilyl]oxy]-4-methyl 5-(2-methylthiazol-4-yl)-pent-4-ene Analogously to Example 22, 6.22 g (80%) of the title compound is obtained from 6.25 g of the compound that is described under Example 25. The coverage of the ¹H-NMR spectrum is identical to 22.

EXAMPLE 27

(5E,3R)-[3-[[(1,1-Dimethylethyl)diphenylsilyl]oxy]-4-methyl-5-(2-methylthiazol-4-yl)-pent-4-en-1-yl]-triphenylphosphonium iodide Analogously to Example 23, 7.36 g (70%) of the title compound is obtained from 6.22 g of the compound that is described under Example 26. The coverage of the ¹H-NMR spectrum is identical to 23.

EXAMPLE 28

(E,3RS)-1-[[Dimethyl(1,1-dimethylethyl)silyl]oxy]-3-[[(1,1-dimethylethyl)diphenylsilyl]oxy]-4-methyl-5-(2-methylthiazol-4-yl)-pent-4-ene Analogously to Example 19, 4.52 g (87%) of the title compound is obtained from 4.3 g of the compound that is described under Example 18. The coverage of the ¹H-NMR spectrum is identical to 19.

EXAMPLE 29

(E,3RS)-3-[[(1,1-Dimethylethyl)diphenylsilyl]oxy]-4-methyl-5-(2-methylthiazol-4-yl)-pent-4-en-1-ol Analogously to Example 20, 3.16 g-(88%) of the title compound is obtained from 4.52 g of the compound that is described under Example 28, The coverage of the ¹H-NMR spectrum is identical to 20.

EXAMPLE 30

(E,3RS)-1-Iodo-3-[[(1,1-dimethylethyl)diphenylsilyl]oxy]-4-methyl-5-(2-methylthiazol-4-yl)-pent-4-ene Analogously to Example 22, 3.34 g (85%) of the title compound is obtained from 3.16 g of the compound that is described, under Example 25. The coverage of the ¹H-NMR spectrum is identical to 22.

EXAMPLE 31

(5E,3RS)-(3-[[(1,1-Dimethylethyl)diphenylsilyl]oxy]-4-methyl-5-(2-methylthiazol-4-yl)-pent-4-en-1-yl]-triphenylphosphonium iodide Analogously to Example 23, 4.35 g (77%) of the title compound is obtained from 3.34 g of the compound that is described under Example 26. The coverage of the ¹H-NMR spectrum is identical to 23.

EXAMPLE 32

(E,3S)-1-[[Dimethyl(1,1-dimethylethyl)silyl]oxy]-3-[[(1,1-dimethylethyl)diphenylsilyl]oxy]-4-methyl-5-(2-pyridyl)-pent-4-ene Analogously to Example 19, 2 g (4.23 mmol) of the compound that is presented according to Example 6 is reacted with use of diethyl(2-pyridyl)methanephosphonate, and after working-up and purification, 2 g (3.68 mmol, 87%) of the title compound is isolated as a colorless oil.

¹H-NMR (CDCl₃): δ=−0.06 (6H), 0.80 (9H), 1.09 (9H), 1.81 (1H), 1.90 (1H), 2.00 (3H), 3.53 (2H), 4.40 (1H), 6.22 (1H), 6.99 (1H), 7.06 (1H), 7.25–7.45 (6H), 7.58 (1H), 7.65–7.77 (4H), 8.58 (1H) ppm.

EXAMPLE 33

(E,3S)-3-[[(1,1-Dimethylethyl)diphenylsilyl]oxy]-4-methyl-5-(2-pyridyl)-pent-4-en-1-ol Analogously to Example 20, 2 g (3.68 mmol) of the compound that is produced under Example 32 is reacted with a 65:35:10 mixture that consists of glacial acetic acid/water/tetrahydrofuran. After purification, 0.1.38 g (3.20 mmol, 87%) of the title compound is obtained.

$^1$H-NMR (CDCl$_3$): δ=1.12 (9H), 1.85 (2H), 2.00 (3H), 3.62 (2H), –4.45 (1H), 6.44 (1H), 7.03 (1H), 7.08 (1H), 7.25–7.48 (6H), 7.59 (1H), 7.65–7.77 (4H), 8.58 (1H) ppm.

EXAMPLE 34

(Z,3S)-1-[[Dimethyl(1,1-dimethylethyl)silyl]oxy]-3-[[(1,1-dimethylethyl)diphenylsilyl]oxy]-4-methyl-5-(3-pyridyl)-pent-4-ene (A) and (E,3S)-1-[[dimethyl (1,1-dimethylethyl)silyl]oxy]-3-[[1(1,1-dimethylethyl)diphenylsilyl]oxy]-4-methyl-5-(3-pyridyl) -pent-4-ene (B)

Analogously to Example 19, 4.8 g (10.2 mmol) of the compound that is presented according to Example 6 is reacted with use of diethyl(3-pyridyl)methanephosphonate, and after working-up and purification, 448 mg (0.82 mmol, 8%) of title compound A and 3.5 g (6.4.1 mmol, 63%) of title compound B are isolated in each case as a colorless oil.

$^1$H-NMR (CDCl$_3$) of A: δ=–0.06 (6H), 0.81 (9H), 1.01 (9H), 1.75 (1H), 1.97 (4H), 3.48 (2H), 4.83 (1H), 6.11 (1H), 6.97 (1H), 7.11–7.30 (5H), 7.30–7.39 (2H), 7.39–7.50 (4H), 8.08 (1H), 8.33 (1H) ppm.

$^1$H-NMR (CDCl$_3$) of B: δ=–0.01 (6H), 0.85 (9H), 1.11 (9H), 1.78 (3H), 1.83 (1H), 1.97 (1H), 3.58 (2H), 4.42 (1H) 6.03 (1H), 7.21 (1H), 7.28–7.50 (7H), 7.62–7.75 (4H), 8.29 (1H), 8.41 (1H)

EXAMPLE 35

(E,3S)-3-[[(1,1-Dimethylethyl)diphenylsilyl]oxy]-4-methyl-5-(3-pyridyl)-pent-4-en-1-ol Analogously to Example 20, 3.5 g (6.41 mmol) of the compound that is produced under Example 34B is reacted with a 65:35:10 mixture that consists of glacial acetic acid/water/tetrahydrofuran. After purification, 2.1 g (4.86 mmol, 761%o) is obtained.

$^1$H-NMR (CDCl$_3$) δ=1.12 (9H), 1.75 (3H), 1.88 (2H), 3.65 (2H), 4.45 (1H), 6.25 (1H), 7.21 (1H), 7.28–7.50 (7H), 7.60–7.75 (4H), 8.30 (1H), 8.44 (1H) ppm.

EXAMPLE 36

Analogously to Example 22, 1.98 g (75%) of the title compound is obtained from 2.1 g of the compound that is described under Example 35.

$^1$H-NMR (CDCl$_3$): δ=1.11 (9H), 1.78 (3H), 2.17 (2H), 3.03 (2H), 4.29 (1H), 6.19 (1H), 7.22 (1H), 7.30–7.50 (7H), 7.63–7.75 (4H), 8.32 (1H), 8.44 (1H) ppm.

EXAMPLE 37

Analogously to Example 23, 2.35 g (80%) of the title compound is obtained from 1.98 g of the compound that is described under Example 36.

$^1$H-NMR (CDCl$_3$) δ=1.08 (9H), 1.80 (3H), 3.27 (1H), 3.56 (1H), 4.66 (1H), 6.52 (1H), 7.25–7.90 (27H), 8.35 (1H), 8.46 (1H) ppm.

EXAMPLE 38

(Z,3S)-1-[[Dimethyl(1,1-dimethylethyl)silyl]oxy]-3-[[(1,1-dimethylethyl)diphenylsilyl]oxy]-4-methyl-5-(4-pyridyl)-pent-4-ene (A) and (E,3S)-1-[[dimethyl (1,1-dimethylethyl)silyl]oxy]-3-[[(1,1-dimethylethyl)diphenylsilyl]oxy]-4-methyl-5-(4-pyridyl) pent-4-ene (B)

Analogously to Example 19, 4.59 g (9.75 mmol) of the compound that is presented according to Example 6 is reacted with use of diethyl(4-pyridyl)methanephosphonate, and after working-up and purification, 605 mg (1.11 mmol, 11%) of title compound A and 4.34 g (7.95 mmol, 82%) of title compound B are isolated in each case as a colorless oil.

$^1$H-NMR (CDCl$_3$) of A: δ=–0.05 (6H), 0.82 (9H), 1.02 (9H) 1.78 (1H), 1.96 (3H), 3.48 (2H), 4.92 (1H), 6.08 (1H), 6.73 (2H), 7.20–7.30 (4H), 7.32–7.40 (2H), 7.41–7.49 (4H), 8.30 (2H) ppm.

$^1$H-NMR (CDCl$_3$) of B: δ=–0.04 (6H), 0.80 (9H), 1.08 (9H), 1.78 (3H), 1.91 (1H), 3.55 (2H), 4.39 (1H), 6.02 (1H), 6.93 (2H), 7.26–7.48 (6H), 7.60–7.72 (4H), 8.50 (2H) ppm.

EXAMPLE 39

(E,3S)-3-[[(1,1-Dimethylethyl)diphenylsilyl]oxy]-4-methyl-5-(4-pyridyl)-pent-4-en-1-ol Analogously to Example 20, 4.34 g (7.95 mmol) of the compound that is produced under Example 38B is reacted with a 65:35:10 mixture that consists of glacial acetic acid/water/tetrahydrofuran. After purification, 2.92 g (6.76-mmol, 85%) of the title compound is obtained.

$^1$H-NMR (CDCl$_3$): δ=1.12 (9H), 1.78 (3H), 1.87 (2H), 3.65 (2H), 4.42 (1H), 6.26 (1H), 6.97 (2H), 7.26–7.48 (6H), 7.60–7.72 (4H), 8.52 (2H) ppm.

EXAMPLE 40

Analogously to Example 22, 2.82 g (77%) of the title compound is obtained from 2.92 g (6.76 mmol) of the compound that is described under Example 39.

$^1$H-NMR (CDCl$_3$): δ=1.08 (6H), 1.78 (3H), 2.15 (2H), 3.00 (2H), 4.26 (1H), 6.17 (1H), 6.95 (2H), 7.30–7.50 (6H), 7.60–7.70 (4H), 8.50 (2H) ppm.

EXAMPLE 41

Analogously to Example 23, 3.27 g (4.06 mmol, 78%) of the title compound is obtained from 2.82 g (5.21 mmol) of the compound that is described under Example 40.

$^1$H-NMR (CDCl$_3$): δ=1.09 (6H), 1.82 (3H), 3.15 (1H), 3.50 (1H), 4.65 (1H), 6.53 (1H), 7.05 (2H), 7.25–7.48 (6H), 7.50–7.70 (4H), 8.50 (2H) ppm.

Examples of the Production of the Compounds of General Formula I According to the Invention

EXAMPLE 1

(4S,7R,8S,9S,13Z,16S(E))-4,8-Dihydroxy-7-ethyl-16-(1-methyl-2-(2-pyridyl)ethenyl)-1-oxa-5,5-trimethylene-9,13-dimethyl -cyclohexadec-ene-2,6-dione

EXAMPLE 1a (3S,6R,7S,8S,12E/Z,15S,16E)-6-Ethyl-7-hydroxy-8,12,16-trimethyl-17-(2-pyridyl)-4,4-trimethylene-1,3,15-tris -[[dimethyl(1,1-dimethylethyl)silyl]oxy]-heptadeca-12,16-dien-5-one (A) and (3S,6S,7R,8S,12E/Z,15S,16E)-6-ethyl-7-hydroxy -8,12,16-trimethyl-17-(2-pyridyl)-4,4-trimethylene-1,3,15-tris -[[dimethyl(1,1-dimethylethyl)silyl]oxy]-heptadeca-12,16-dien-5-one (B)

The solution of 0.38 ml of diisopropylamine in 12 ml of anhydrous tetrahydrofuran is cooled under an atmosphere of dry argon to −30° C., mixed with 1.13 ml of a 2.4 molar solution of n-butyllithium in n-hexane and stirred for 15 more minutes. At −78° C., the solution of 1.05 g (2.53 mmol) of (S)-1-(1,3-bis[[dimethyl(1,1-dimethylethyl)silyl]oxypropyl]-cyclobutyl)propan-1-one, which was produced according to the process described in DE 197 51 200.3, in 12 ml of tetrahydrofuran is added in drops, and it is allowed to react for 1 hour. Then, it is mixed with the solution of 964 mg (2.32 mmol) of (2S,6E/Z,9S,10E)-9-((dimethyl(1,1-dimethylethyl)silyl]oxy]-11-(2-pyridyl)-2,6,10-trimethyl-undeca-6,10-dienal, which was produced according to the process described in DE 197 51 200.3, in 12 ml of tetrahydrofuran, and it is poured into saturated ammonium chloride solution after 45 minutes. It is diluted with water, extracted several times with ethyl acetate, the combined organic extracts are washed with saturated sodium chloride solution, dried on sodium sulfate and concentrated by evaporation in a vacuum. After column chromatography on silica gel with a gradient system that consists of n-hexane and ethyl acetate, 1.17 g (1.41 mmol, 61%) of title compound A and 0.30 g (0.36 mmol, 16%) of a diastereomer B are obtained in addition to starting material.

$^1$H-NMR (CDCl$_3$) of A: δ=0.02–0.18 (18H), 0.80 (3H), 1.03 (3H), 1.61+1.69; (3H), 2.06 (3H), 0.83–2.11 (39H), 2.22–2.43 (5H), 3.27 (1H), 3.34 (1H), 3.54–3.65 (3H), 4.08–4.18 (2H), 5.18 (1H), 6.48 (1H), 0.7.08 (1H), 7.22 (1H), 7.62 (1H), 8.60 (1H) ppm.

EXAMPLE 1b (3S,6R,7S,8S,12E/Z,15S,16E)-6-Ethyl-17-(2-pyridyl) -8,12,16-trimethyl-4,4-trimethylene-1,3,7,15-tetrakis -[[dimethyl(1,1-dimethylethyl)silyl]oxy]-heptadeca-12,16-dien-5-one The solution of 1.17 g (1.41 mmol) of the compound, produced according to Example 1a, in 40 ml of anhydrous dichloromethane is cooled to −78° C. under an atmosphere of dry argon, mixed with 2.8 ml of 2,6-lutidine, 2.6 ml of trifluoromethanesulfonic acid-tert-butyldimethylsilyl ester and stirred for 16 hours. It is poured into saturated sodium bicarbonate solution and extracted several times with dichloromethane. The combined organic extracts are dried on sodium sulfate and concentrated by evaporation in a vacuum. After column chromatography on silica gel with a gradient system that consists of n-hexane and ethyl acetate, 1.30 g (1.38 mmol, 98%) of the title compound is isolated as a colorless oil.

$^1$H-NMR (CDCl$_3$): δ=−0.01–0.18 (24H), 0.83–0.98 (39H), 1.07 (3H), 1.10–2.10 (13H), 1.60+1.68 (3H), 2.06 (3H), 2.19–2.40 (4H), 3.09 (1H), 3.69 (2H), 3.78 (1H), 4.04–4.18 (2H), 5.17 (1H), 6.48 (1H), 7.08 (1H), 7.21 (1H), 7.61 (1H), 8.60 (1H) ppm.

EXAMPLE 1c (3S,6R,7S,8S,12E/Z,15S,16E)-6-Ethyl-1-hydroxy-8,12,16-trimethyl-4,4-trimethylene-17-(2-pyridyl)-3,7,15-tris -[[(dimethyl(1,1-dimethylethyl)silyl]oxy]-heptadeca-12,16-dien-5-one The solution of 1.30 g (1.38 mmol) of the compound, presented according to Example 1b, in a mixture that consists of 15 ml of dichloromethane and 15 ml of methanol is mixed at 23° C. under an atmosphere of dry argon with 320 mg of camphor-10-sulfonic acid, and it is stirred for 22 more hours. It is mixed with triethylamine, poured into a saturated sodium bicarbonate solution and extracted several times with dichloromethane. The combined organic extracts are dried on sodium sulfate and concentrated by evaporation in a vacuum. After column chromatography on fine silica gel with a gradient system that consists of n-hexane and ethyl acetate, 614 mg (739 mmol, 54%) of the title compound is isolated.

EXAMPLE 1d (3S,6R,7S,8S,12E/Z,15S,16E)-6-Ethyl-5-oxo-8,12,16-trimethyl-4,4-trimethylene-17-(2-pyridyl)-3,7,15-tris [[dimethyl(1,1-dimethylethyl)silyl]oxy]-heptadeca-12,16-dienal The solution of 0.16 ml of oxalyl chloride in 6 ml of anhydrous dichloromethane is cooled under an atmosphere of dry argon to −78° C., mixed with 0.26 ml of dimethyl sulfoxide, the solution of 610 mg (0.735 mmol) of the compound, presented according to Example 1c, in 6 ml of anhydrous dichloromethane, and it is stirred for 0.5 hour. Then, it is mixed with 0.75 ml of triethylamine, allowed to heat to 0° C. and mixed with n-hexane and saturated sodium bicarbonate solution. The organic phase is separated, the aqueous phase is extracted several more times with n-hexane, the combined organic extracts are washed with water and dried on magnesium sulfate. The residue that is obtained after filtration and removal of the solvent is further reacted without purification.

EXAMPLE 1e (3S,6R,7S,8S,12E,15S,16E)-6-Ethyl-5-oxo-8,12,16-trimethyl-4,4-trimethylene-17-(2-pyridyl)-3,7,15-tris -[[dimethyl(1,1-dimethylethyl)silyl]oxy]-heptadeca-12,16-dienoic acid (A) and (3S,6R,7S,8S,12Z,15S,16E)-6-ethyl-5-oxo-8,12,16-trimethyl-4,4-trimethylene-17-(2-pyridyl)-3,7,15-tris -[[dimethyl(1,1-dimethylethyl)silyl]oxy]-heptadeca-12,16-dienoic acid (B)

The solution of 651 mg (maximum 0.74 mmol) of the compound, presented according to Example 1d, in 16 ml of acetone is cooled to −30° C., mixed with 540 µl of a standardized 8N chromosulfuric acid solution and stirred for 1.5 hours. It is poured into a mixture that consists of water and diethyl ether, the organic phase is washed with saturated sodium chloride solution and dried on sodium sulfate. The residue that is obtained after filtration and removal of the solvent is purified by chromatography on about 300 ml of fine silica gel with a gradient system that consists of n-hexane and ethyl acetate. 190 mg (225 µmol, 30% relative to the educt in Example 1d) of title compound A and 280 mg (332 µmol, 45% relative to the educt in Example 1d) of title compound B in each case are isolated as colorless oils.

¹H-NMR (CDCl₃) of A: δ=0.03 (3H), 0.05 (3H), 0.09 (6H), 0.13 (3H), 0.20 (3H), 0.84–0.96 (30H), 1.02–1.50 (5H), 1.12 (3H), 1.57 (3H), 1.63–2.06 (4H), 1.93 (3H), 2.12–2.46 (8H), 3.07 (1H), 3.90 (1H), 4.13 (1H), 4.48 (1H), 5.12 (1H), 6.49 (1H), 7.17 (1H), 7.32 (1H), 7.70 (1H), 8.60 (1H) ppm.

¹H-NMR (CDCl₃) of B: δ=0.00 (3H), 0.04 (6H), 0.08 (3H), 0.11 (3H), 0.17 (3H), 0.84–0.97 (30H), 1.05–1.98 (8H), 1.12 (3H), 1.68 (3H), 1.91 (3H), 2.05–2.35 (8H), 2.42 (1H), 2.94 (1H), 3.92 (1H), 4.12 (1H), 4.53 (1H), 5.20 (1H), 6.60 (1H), 7.17 (1H, 7.32 (1H), 7.70 (1H), 8.59 (1H) ppm.

EXAMPLE 1f (3S,6R,7S,8S,12Z,15S,16E)-6-Ethyl-15-hydroxy-5-oxo -8,12,16-trimethyl-4,4-trimethylene-17-(2-pyridyl)-3,7-bis -[[dimethyl(1,1-dimethylethyl)silyl]oxy]-heptadeca-12,16-dienoic acid The solution of 280 mg (332 μmol) of compound B, produced according to Example 1e, in 13 ml of anhydrous tetrahydrofuran is mixed under an atmosphere of dry argon with 5 ml of a 1 molar solution of tetrabutylammonium fluoride in tetrahydrofuran, and it is stirred for 4 hours at 23° C. It is mixed with saturated sodium bicarbonate solution, extracted several times with ethyl acetate, washed with saturated sodium chloride solution and dried on sodium sulfate. The residue that is obtained after filtration and removal of the solvent (289 mg) is further-reacted without purification.

EXAMPLE 1g (4S,7R,8S,9S,13Z,16S(E))-4,8-Bis-[[dimethyl(1,1-dimethylethyl)silyl]oxy]-7-ethyl-16-(1-methyl-2-(2-pyridyl)ethenyl)-1-oxa-5,5-trimethylene-9,13-dimethyl -cyclohexadec-13-ene-2,6-dione The solution of 289 mg (maximum 332 mmol) of the compound, presented according to Example 1f, in a mixture that consists of 2.6 ml of anhydrous tetrahydrofuran and 30 ml of toluene is mixed under an atmosphere of dry argon with 276 μl of triethylamine, 260 μl of 2,4,6-trichlorobenzoyl chloride, and it is stirred for 20 minutes. This solution is added in drops within 3.5 hours to the solution of 422 mg of 4-dimethylaminopyridine in 130 ml of toluene, and it is stirred for 2 more hours at 23° C. It is concentrated by evaporation, taken up in a little dichloromethane and purified by chromatography on about 200 ml of fine silica gel with a gradient system that consists of n-hexane and ethyl acetate. 165 mg (232 μmol, 70%) of the title compound is isolated as a colorless oil.

¹H-NMR (CDCl₃): δ=−0.05 (3H), 0.02–0.19 (9H), 0.80 (9H), 0.85–1.94 (15H), 0.94 (3H), 0.99 (3H), 1.22 (3H), 1.68 (3H), 1.99–2.80 (8H), 2.16 (3H), 2.97 (1H), 3.93 (1H), 4.41 (1H), 5.08 (1H), 5.18 (1H), 6.58 (1H), 7.11 (1H), 7.27 (1H), 7.65 (1H), 8.60 (1H) ppm.

EXAMPLE 1

(4S,7R,8S,9S,13Z,16S(E))-4,8-Dihydroxy-7-ethyl-16-(1-methyl-2-(2-pyridyl)ethenyl)-1-oxa-5,5-trimethylene-9,13-dimethyl-cyclohexadec-13-ene-2,6-dione The solution of 165 mg (232 μmol) of the compound, presented according to Example 1g, in 1.8 ml of anhydrous dichloromethane is mixed at 0° C. under an atmosphere of dry argon in portions with a total of 1.4 ml of an approximately 20% trifluoroacetic acid, and it is stirred for 24 hours. It is poured into a saturated sodium bicarbonate solution, extracted with dichloromethane, and the organic phase is dried on sodium sulfate. After filtration and removal of the solvent, the residue is purified by chromatography on about 200 ml of fine silica gel with a gradient system that consists of n-hexane and ethyl acetate. 86 mg (178 μmol, 77%) of the title compound is isolated as a colorless oil.

¹H-NMR; (CDCl₃): δ=1.01 (3H), 1.18–2.55 (16H), 1.25 (3H), 1.68 (3H), 2.07 (3H), 2.63 (1H), 2.97–3.10 (2H), 3.72 (1H), 4.53 (1H), 4.54–4.83 (1H), 5.07–5.20 (2H), 6.63 (1H), 7.13 (1H), 7.31 (1H), 7.69 (1H), 8.56 (1H) ppm.

EXAMPLE 2

(1S,3S(E),7S,10R,11S,12S,16R)-7,11-Dihydroxy-10-ethyl -3-(1-methyl-2-(2-N-oxypyridyl)ethenyl)-8,8-trimethylene-12,16-dimethyl-4,17-dioxabicyclo[14.1.0]heptadecane-5,9-dione (A) and (1R,3S(E),7S,10R11S,12S,16S)-7,11-dihydroxy-10-ethyl-3-(1-methyl-2-(2-N-oxypyridyl)ethenyl)-8,8-trimethylene-12,16-dimethyl-4,17-dioxabicyclo[14.1.0]heptadecane-5,9-dione (B)

The solution of 20 mg (41 μmol) of the compound, presented according to Example 1, in 1 ml of acetonitrile is mixed with 264 μl of a 0.1 M solution of sodium ethylenediamine-tetraacetate, cooled to 0° C. and mixed with 400 μl of 1,1,1-trifluoroacetone as well as a mixture that consists of 37 mg of oxone and 35 mg of sodium bicarbonate. It is allowed to react for 5 hours, poured onto sodium thiosulfate solution and extracted several times with ethyl acetate. The combined organic extracts are washed with saturated sodium chloride solution, and the residue that is obtained after filtration and removal of the solvent is purified by chromatography on two analytical thin-layer plates. As a mobile solvent, a mixture that consists of dichloromethane and ethanol is used. 15 mg (29 μmol, 71%) of title compound A and 4 mg (8 μmol, 19%) of title compound B in each case are isolated as colorless oils.

¹H, —NMR (CDCl₃) of A: δ=0.97 (3H), 1.10–2.53 (18H), 1.20 (3H), 1.30 (3H), 2.13 (3H), 2.65–2.80 (2H), 2.98 (1H), 3.12 (1H), 3.68 (1H), 4.61 (1H), 5.37 (1H), 6.49 (1H), 6.94 (1H), 7.22 (1H), 7.33–7.46 (2H), 8.29 (1H) ppm.

¹H-NMR (CDCl₃) of B: δ=0.93 (3H), 1.15 (3H), 1.22–2.51 (16H), 1.30 (3H), 2.13 (3H), 2.64 (1H), 2.89 (1H), 3.18 (1H), 3.38 (1H), 3.80 (1H), 4.62 (1H), 5.42 (1H), 5.90 (1H), 7.03 (1H) 7.21 (1H), 7.36 (1H), 7.46 (1H), 8.30 (1H) ppm.

EXAMPLE 3

(1S,3S(E),7S,10R,11S,12S,16R)-7,11-Dihydroxy-10-ethyl -3-(1-methyl-2-(2-pyridyl)ethenyl)-8,8-trimethylene-12,16-dimethyl-4,17-dioxabicyclo[14.1.0]heptadecane-5,9-dione Under an atmosphere of dry argon, the solution of 15 mg (29 μmol) of compound A, presented according to Example 2, in 2 ml of trichloromethane, is mixed with 0.6 ml of 2-propanol, 5 mg of tetrapropylammonium perruthenate, molecular sieve (4 Å), and it is stirred for 2.5 days at 50° C. It is purified by chromatography on an analytical thin-layer plate. As mobile solvent and eluant, a mixture that consists of dichloromethane and: ethanol is used. 12 mg (24 μmol, 83%) of the title compound is isolated as a colorless foam.

$^1$H-NMR (CDCl$_3$): δ=0.98 (3H), 1.22 (3H), 1.20–2.62 (17H), 1.30 (3H), 2.07 (3H), 2.78 (1H), 2.85 (1H), 3.08 (1H), 3.71 (1H), 4.53 (1H), 5.33 (1H), 5.36 (1H), 6.62 (1H), 7.18 (1H), 7.31 (1H), 7.72 (1H), 8.54 (1H) ppm.

EXAMPLE 4

(1R,3S(E),7S,10R,11S,12S,16S)-7,11-Dihydroxy-10-ethyl -3-(1-methyl-2-(2-pyridyl)ethenyl)-8,8-trimethylene-12,16-dimethyl-4,17-dioxabicyclo [14.1.0]heptadecane-5,9-dione Analogously to Example 3, 4 mg (8 μmol) of compound B, presented according to Example 2, is reacted, and after working-up and purification, 2 mg (4 μmol, 50%) of the title compound is isolated as a colorless oil.

$^1$H-NMR (CDCl$_3$): δ=0.94 (3H), 1.19 (3H), 1.23–2.20 (13H), 1.30 (3H), 2.13 (3H), 2.27–2.60 (4H), 3.00 (1H), 3.11 (1H), 3.15 (1H), 3.81 (1H), 3.92 (1H), 4.41 (1H), 5.61 (1H), 6.67 (1H), 7.13 (1H), 7.28 (1H), 7.67 (1H), 8.59 (1H) ppm.

EXAMPLE 5

(4S,7R,8S,9S,13E,16S(E))-4,8-Dihydroxy-7-ethyl-16-(1-methyl-2-(2-pyridyl)ethenyl)-1-oxa-5,5-trimethylene-9,13-dimethyl -cyclohexadec-13-ene-2,6-dione and (4S,7R,8S,9S,13E,16S(E))-7-ethyl-4-hydroxy-16-(1-methyl-2-(2-pyridyl)ethenyl)-1-oxa-5,5-trimethylene-9,13-dimethyl-8-trifluoroacetoxy-cyclohexadec-13-ene-2,6-dione

EXAMPLE 5a (3S,6R,7S,8S,12E,15S,16E)-6-Ethyl-15-hydroxy-5-oxo -8,12,16-trimethyl-4,4-trimethylene-17-(2-pyridyl)-3,7-bis -[[dimethyl(1,1-dimethylethyl)silyl] oxy]-heptadeca-12,16-dienoic acid Analogously to Example 1f, 190 mg (225 μmol) of compound A, presented according to Example 1e, is reacted, and after working up, 198 mg of the title compound is isolated as a crude product, which is further reacted without purification.

EXAMPLE 5b (4S,7R,8S,9S,13E,16S(E))-4,8-Bis-((dimethyl(1,1-dimethylethyl)silyl]oxy]-7-ethyl-16-(1-methyl-2-(2-pyridyl)ethenyl)-1-oxa-5,5-trimethylene-9,13-dimethyl -cyclohexadec-13-ene-2,6-dione Analogously to Example 1g, 198 mg (maximum 225 μmol) of the compound, presented according to Example 5a, is reacted, and after working-up and purification, 116 mg (163 μmol, 72%) of the title compound is isolated as a colorless oil.

$^1$H-NMR (CDCl$_3$) δ=0.00 (3H), 0.03 (3H), 0.08 (3H), 0.12 (3H), 0.76–2.21° (12H), 0.83 (9H), 0.92 (12H), 1.22 (3H), 1.47 (3H), 2.17 (3H), 2.29–2.51 (4H), 2.82–2.99 (2H), 4.16*(1H), 4.67 (1H), 5.09 (1H), 5.31 (1H), 6.58 (1H), 7.10 (1H), 7.18 (1H), 7.62 (1H), 8.61 (1H) ppm.

EXAMPLE 5

(4S,7R,8S,9S,13E,16S(E))-4,8-Dihydroxy-7-ethyl-16-(1-methyl-2-(2-pyridyl)ethenyl)-1-oxa-5,5-trimethylene-9,13-dimethyl-cyclohexadec-13-ene-2,6-dione The solution of 116 mg (163 μmol) of the compound, presented according to Example 5b, in 10 ml of anhydrous tetrahydrofuran is mixed under an atmosphere of dry argon in portions with a total of 3.1 ml of HF-pyridine complex, and it is stirred for 3 days at 23° C. it is poured into saturated sodium bicarbonate solution, extracted several times with dichloromethane, and the combined organic extracts are dried on sodium sulfate. After filtration and removal of the solvent, the residue that is obtained is purified by chromatography on about 50 ml of fine silica gel with a mixture that consists of n-hexane and ethyl acetate. 63 mg (130 μmol, 80%) of the title compound is isolated as a colorless oil as well as 16 mg of monosilyl ether.

$^1$H-NMR (CDCl$_3$) δ=0.91–1.06 (1H), 0.99 (3H), 1.21 (3H), 1.29–1.45 (2H), 1.52–2.24 (9H), 1.56 (3H), 2.09 (3H), 2.34–2.71 (5H), 3.06 (1H), 3.59 (1H), 3.67 (1H), 3.90 (1H), 4.50 (1H), 5.10 (1H), 5.41 (1H), 6.60 (1H), 7.14 (1H), 7.37 (1H), 7.69 (1H), 8.55 (1H) ppm.

EXAMPLE 6

(1R,3S(E),7S,10R,11S,12S,16R)-7,11-Dihydroxy-10-ethyl -3-(1-methyl-2-(2-N-oxypyridyl)ethenyl)-8,8-trimethylene-12,16-dimethyl-4,17-dioxabicyclo [14.1.0]heptadecane-5,9-dione (A) and (1S,3S(E),7S,10R,11S,12S,16S)-7,11-dihydroxy-10-ethyl-3-(1-methyl-2-(2-N-oxypyridyl)ethenyl)-8,8-trimethylene-12,16-dimethyl-4,17-dioxabicyclo [14.1.0]heptadecane-5,9-dione (B)

Analogously to Example 2, 61 mg (126 μmol) of the compound, presented according to Example 5, is reacted, and after working-up and purification, 57 mg (111 μmol, 88%) of a mixture of title compounds A and B is isolated, which is further reacted without separation.

$^1$H-NMR (CDCl$_3$) of A and B: δ=0.90+0.93 (3H), 1.03–2.52 (23H), 2.70 (1H), 2.89+2.93 (1H), 3.10 (1H), 3.22+3.49 (1H), 3.54–3.78 (2H), 4.60+4.73 (1H), 5.46+5.65 (1H), 5.81+6.01 (1H), 7.09 (1H), 8.18–7.54 (4H), 8.30 (1H) ppm.

EXAMPLE 7

(1R,3S(E),7S,10R,11S,12S,16R)-7,11-Dihydroxy-10-ethyl -3-(1-methyl-2-(2-pyridyl)ethenyl)-8,8-trimethylene-12,16-dimethyl-4,17-dioxabicyclo [14.1.0]heptadecane-5,9-dione (A) and (1S,3S(E), 7S,10R,11S,12S,16S)-7,11-dihydroxy-10-ethyl-3-(1-methyl-2-(2-pyridyl)ethenyl)-8,8-trimethylene-12, 16-dimethyl -4,17-dioxabicyclo[141.0]heptadecane-5,9-dione (B)

Analogously to Example 3, 56 mg (109 μmol) of the mixture of compounds A and B, presented according to Example 6, is reacted, and after working-up, purification and chromatographic separation, 10 mg (20.0 μmol, 18k) of title compound A or B or 23 mg (46.0 μmol, 42%) of title compound B or A in each case is isolated as a colorless oil.

$^1$H-NMR (CDCl$_3$) of A or B: δ=0.89 (3H), 1.12–1.45 (5H), 1.20 (3H), 1.24 (3H), 1.68–2.61 (12H), 2.06 (3H), 2.90

(1H), 3.08 (1H), 3.18 (1H), 3.69 (1H), 4.35 (1H), 4.53 (1H), 5.43 (1H), 6.62 (1H), 7.14 (1H), 7.28 (1H), 7.69 (1H), 8.56 (1H) ppm.
$^1$H-NMR (CDCl$_3$) of B or A: δ=0.92 (3H), 1.02–1.62 (5H), 1.20 (3H), 1.22 (3H), 1.67–2.64 (12H), 2.08 (3H), 2.89 (1H), 3.11 (1H), 3.67 (2H), 4.47 (1H), 4.56 (1H), 5.53 (1H), 6.70 (1H), 7.16 (1H), 7.39 (1H), 7.71 (1H), 8.52 (1H) ppm.

EXAMPLE 8

(4S,7R,8S,9S,13(Z),16S(E))-4,8-Dihydroxy-16-(2-(2-methyl-4-thiazolyl)ethenyl)-1-oxa-5,5,7,9,13-pentamethyl-cyclohexadec-13-ene-2,6-dione Analogously to Example 1, 13.8 mg of the title compound is obtained from the phosphonium salt of Example 81 as a yellowish oil.
$^1$H-NMR (CDCl$_3$): =1.1 (3H), 1.04 (3H), 1.19 (3H), 1.38 (3H), 0.8–1.8 (8H), 1.66 (3H), 1.85–1.92 (1H), 2.21 (1H), 2.27–2.34 (1H), 2.44 (1H), 2.67 (1H), 2.92 (1H), 3.17 (1H), 3.5 (3H), 3.67 (1H), 4.35 (1H), 5.15 (1H), 5.45 (1H), 6.71 (1H), 7.08 (1H) ppm.

EXAMPLE 8a

2-Methylthiazole-4-carbaldehyde 476 ml of a 1.2 molar solution of DIBAH in toluene is slowly added in drops at −75° C. under nitrogen to a solution that consists of 60 g of 2-methylthiazole-4-carboxylic acid ethyl ester in 1070 ml of methylene chloride. It is stirred for 2 more hours. Then, 150 ml of isopropanol, and then 230 ml of water are slowly added in drops to it, the cold bath is removed and stirred vigorously at 25° C. for 2 more hours. The precipitate that is produced is suctioned off and rewashed with ethyl acetate. The filtrate is concentrated by evaporation in a vacuum, and the residue that is thus obtained is purified by chromatography on silica gel. 35.6 g of the title compound is obtained with hexane/ether 1:1 as a colorless oil.
$^1$H-NMR (CDCl$_3$): δ=2.8 (3H), 8.05 (1H), 10.0 (1H) ppm.

EXAMPLE 8b (2E)-3-(2-Methylthiazol-4-yl)-2-propenoic acid methyl ester 51 g of methyl-(triphenylphosphoranylidene)-acetate is added to a solution that consists of 16.9 g of previously produced aldehyde in 260 ml of toluene, and it is refluxed under nitrogen for 3 hours. After the reaction solution is cooled, it is concentrated by evaporation in a vacuum. The residue that is thus obtained is purified by chromatography on silica gel. With hexane/ethyl acetate 1:1, 19.9 g of the title compound is obtained as colorless crystals.
Flash point: 103–105° C.
$^1$H-NMR (CDCl$_3$): δ=2.75 (3H), 3.8 (3H), 6.72 (1H), 7.58 (1H) ppm.

EXAMPLE 8c (2E)-3-(2-Methylthiazol-4-yl)-2-propen-1-ol 50 ml of a 1.2 molar solution of DIBAH in toluene is added in drops at −70° C. under nitrogen to a solution that consists of 5.5 g of previously produced ester in 100 ml of toluene/methylene chloride 1:1. After one hour, 15 ml of isopropanol and then 25 ml of water are slowly added in drops to it, and it is stirred vigorously for 2 more hours. The precipitate that is produced is suctioned off and washed well with ethyl acetate. The filtrate is concentrated by evaporation in a vacuum, and the residue that is thus obtained is purified by chromatography on silica gel. 4.2 g of the title compound is obtained as a colorless oil with hexane/ethyl acetate 0–60%.
$^1$H-NMR (CDCl$_3$) δ=1.91–1.98 (1H), 2.71 (3H), 4.30–4.38 (2H), 6.55–6.75 (2H), 6.93 (1H) ppm.

EXAMPLE 8d (2E)-3-(2-Methylthiazol-4-yl)-2-propenal

A total of 8 g of manganese dioxide is added in portions to a solution that consists of 1 g of previously produced alcohol in 30 ml of toluene, and it is stirred vigorously under nitrogen for 4 more hours. Manganese dioxide is suctioned off on Celite, washed well with ethyl acetate, and the filtrate is concentrated by evaporation in a vacuum. 850 mg of the title compound is obtained as light-colored crystals.
Flash point: 89–90° C.
$^1$H-NMR (CDCl$_3$): δ=2.75 (3H), 6.88–7.0 (1H), 7.39 (1H), 9.7 (1H) ppm.

EXAMPLE 8e (3S,4E)-5-(2-Methylthiazol-4-yl)-1-[(4S,5R)-4-methyl-5-phenyl-oxazolidin-2-on-3-yl]-3-hydroxy-4-penten-1-one 5 g of anhydrous chromium(II) chloride in 60 ml of THF is introduced under argon and mixed with 218 mg of lithium iodide. Then, a solution that consists of 2.49 g of previously produced aldehyde and 5.34 g of (4S,5R)-3-(bromoacetyl)-4-methyl-5-phenyloxazolidin-2-one in 10 ml of THF is added in drops. It is stirred for 3 more hours. 40 ml of saturated sodium chloride solution is added to it, it is stirred for 30 minutes, and the phases are separated. The aqueous phase is extracted twice with 100 ml of ethyl acetate each, the combined organic phases are extracted once with water, and once with saturated sodium chloride solution. The organic phase is dried on sodium sulfate, filtered off, and the filtrate is concentrated by evaporation in a vacuum. The residue that is thus obtained is purified by chromatography on silica gel. With hexane/ethyl acetate 0–60%, 1.92 g of the title compound and 2.5 g of the corresponding diastereomeric title compound are obtained as light-colored oils.
$^1$H-NMR (CDCl$_3$): δ=0.93 (3H), 2.71 (3H), 3.16 (1H), 3.2–3.4 (2H), 4.75–4.9 (2H), 5.7 (1H), 6.58–6.76 (2H), 6.94 (1H), 7.38–7.5 (5H) ppm.

EXAMPLE 8f (3S,4E)-5-(2-Methylthiazol-4-yl)-1-[(4S,5R)-4-methyl-5-phenyl-oxazolidin-2-on-3-yl]-3-(tert-butyl-dimethylsilyloxy)-4-penten-1-one 0.62 ml of lutidine is added in drops at −70° C. under nitrogen to a solution that consists of 1.42 g of previously produced title compound in 12 ml of methylene chloride, and it is stirred for 5 more minutes. Then, 1.14 ml of tert-butyldimethylsilyl trifluoromethanesulfonate is slowly added in drops. After one hour, it is mixed with 4 ml of saturated ammonium chloride solution, and the reaction mixture is allowed to heat to 25° C. It is diluted with 70 ml of ether, washed once with water and once with saturated sodium chloride solution. The organic phase is dried on sodium sulfate and concentrated by evaporation in a vacuum. The thus obtained residue is purified by chromatography on silica gel. With hexane/ether 1:1, 1.52 g of the title compound is obtained as light-colored crystals.

Flash point: 110–112° C.

$^1$H-NMR (CDCl$_3$): δ=0.1 (6h), 0.9 (12H), 2.72 (3H), 3.13–3.4 (2H), 4.58–4.71 (1H), 4.86–4.97 (1H), 5.62 (1H), 6.59 (2H), 6.91 (1H), 7.23–7.49 (5H) ppm.

EXAMPLE 8g (3S,4E)-5-(2-Methylthiazol-4-yl)-3-(tert-butyl-dimethylsilyloxy) -4-pentenoic acid ethyl ester 0.27 ml of titanium(IV)ethylate is added to a solution that consists of 1.37 g of previously produced title compound in 7 ml of ethanol, and it is refluxed for 4 hours under nitrogen. The reaction solution is concentrated by evaporation in a vacuum, the residue is taken up in 5 ml of ethyl acetate, mixed with 4 drops of water and stirred for 20 minutes. Titanium oxide is suctioned off, washed well with ethyl acetate, and the filtrate is concentrated by evaporation in a vacuum. The residue is mixed with hexane, the crystals are suctioned off and washed twice with hexane. The filtrate is concentrated by evaporation in a vacuum. The thus obtained residue is purified by chromatography on silica gel. With hexane/ether 30%, 910 mg of the title compound is obtained as a light-colored oil.

$^1$H-NMR (CDCl$_3$): δ=0.08 (6H), 0.89 (9H), 1.36 (3H), 2.46–2.64 (2H), 2.7 (3H), 4.05–4.22 (2H), 4.73–4.81 (1H), 6.46–6.6 (2H), 6.9 (1H) ppm.

EXAMPLE 8h (3S,4E)-5-(2-Methylthiazol-[4-yl)-3-(tert-butyl-dimethylsilyloxy) -4-pentenal 45 ml of a 1.2 molar solution of DIBAH in toluene is slowly added in drops under nitrogen at −70° C. to a solution that consists of 8.8 g of previously produced title compound in 100 ml of toluene, and it is stirred for one hour. 10 ml of isopropanol is slowly added in drops to it, then 22 ml of water, and it is stirred vigorously at 25° C. for 2 more hours. The precipitate is suctioned off, washed well with ethyl acetate, and the filtrate is concentrated by evaporation in a vacuum. The thus obtained residue is purified by chromatography on silica gel. With hexane/ether 0–80%, 7.7 g of the title compound is obtained as a yellow oil.

$^1$H-NMR (CDCl$_3$): δ=0.1 (6H), 0.9 (9H), 2.55–2.75 (2H), 2.72 (3H), 4.8–4.9 (1H), 6.58 (2H), 6.91 (1H), 9.8 (1H) ppm.

EXAMPLE 8i (3S,4E)-S-(2-Methylthiazol-4-yl)-3-(tert-butyl-dimethylsilyloxy) -4-penten-1-ol 7.7 g of previously produced title compound is dissolved in 100 ml of methanol and mixed at −60° C. with 1.38 g of CeCl$_3$; it is stirred under nitrogen for 30 minutes. 1.8 g of sodium borohydride is added to it, it is allowed to come to −40° C., and it is stirred for one hour. It is mixed with 20 ml of acetone, stirred for 15 minutes, the cold bath is removed, and pH 7 is set with acetic acid. The solution is concentrated by evaporation in a vacuum, and the residue is taken up in water/ether. The aqueous phase is extracted three times with 100 ml of ether each, the combined organic phases are washed once with water and once with saturated sodium chloride solution, then dried on sodium sulfate and concentrated by evaporation in a vacuum. The thus obtained residue is purified by chromatography on silica gel. With hexane/ether 0–80%, 7.6 g of the title compound is obtained as a yellow oil.

[α]$_D$: −62.3° (c=0.995, CHCl$_3$)

$^1$H-NMR (CDCl$_3$): δ=0.08 (6h), 0.91 (9H), 1.7–2.0 (2H), 2.46 (1H), 2.7 (3H), 3.65–3.9 (2H), 4.57–4.65 (1H), 6.52 (2H), 6.88 (1H) ppm.

EXAMPLE 8k (3S,4E)-5-(2-Methylthiazol-4-yl)-3-(tert-butyl-dimethylsilyloxy) -1-iodo-4-pentene 2 g of imidazole is added to a solution that consists of 7.73 g of triphenylphosphine in 110 ml of methylene chloride. 7.48 g of iodine is added to this solution, allowed to stir for 10 minutes, and then a solution that consists of 7.7 g of previously produced title compound in 30 ml of methylene chloride is added in drops, and it is stirred for 30 minutes. It is filtered off, washed well with ether, and the filtrate is concentrated by evaporation in a vacuum. The thus obtained residue is purified by chromatography on silica gel. With hexane/ether 0–30%, 9.23 g of the title compound is obtained as a yellow oil.

[α]$_D$: +3.8° (c=0.7, CHCl$_3$)

$^1$H-NMR (CDCl$_3$): δ=0.1 (6H), 0.91 (9H), 2.0–2.2 (2H), 2.71 (3H), 3.15–3.32 (2H), 4.32–4.44 (1H), 6.4–6.6 (2H), 6.9 (1H) ppm,

EXAMPLE 8l (3S,4E)-5-(2-Methylthiazol-4-yl)-3-(tert-butyl-dimethylsilyloxy) -4-pentene-triphenylphosphonium iodide 9 g of previously produced title compound is mixed with 6.13 g of triphenylphosphine, and it is stirred under nitrogen at 100° C. for 2 hours. After cooling, the solid residue is pulverized twice with ether and a little ethyl acetate, whereby the supernatant solution is pipetted off. Then, the residue is dissolved in methanol and concentrated by evaporation in a vacuum. The solid foam is again dissolved in a little methanol, mixed with toluene and concentrated by evaporation again in a vacuum. This process is repeated twice, then the residue is dried under high vacuum. 14.1 g of the title compound is obtained as a foam.

$^1$H-NMR (CDCl$_3$): δ=0.12 (6H), 0.89 (9H), 1.75–2.1 (2H), 2.69 (3H), 3.4–3.6 (1H), 0.3.72–4.04 (1H), 4.76–4.89 (1H), 6.4–6.5 (1H), 6.66–6.76 (1H), 7.09 (1H), 7.53–7.9 (1H) ppm.

EXAMPLE 9

(4S,7R,8S,9S,13(E),16S(E))-4,8-Dihydroxy-16-(-2-(2-methyl-4-thiazolyl)ethenyl)-1-oxa-5,5,7,9,13-pentamethyl-cyclohexadec-13-ene-2,6-dione Analogously to Example 1, 15.6 mg of the title compound is obtained from the phosphonium salt of Example 8l as a pale yellow-colored oil.

$^1$H-NMR (CDCl$_3$): δ=0.98 (3H), 1.04 (3H), 1.17 (3H); 0.9–2.0 (5H), 1.38 (3H), 1.58 (3H), 1.68–1.73 (1H), 2.01

(1H), 2.05–2.3 (4H), 2.4–2.66 (3H), 2.94 (3H), 3.22 (1H), 3.61 (1H), 4.3–4.4 (1H), 5.2 (1H), 5.16 (1H); 5.64 (1H), 6.75 (1H), 7.11 (1H) ppm.

EXAMPLE 10

(1R,3S(E),7S,10R,11S,12S,16S)-7,11-Dihydroxy-3-(2-(2-methyl-4-thiazolyl)ethenyl)-8,8,10,12,16-pentamethyl-4,17-dioxabicyclo[14.1.0]heptadecane-5,9-dione (A) and (1S,3S(E),7S,10R,11S,12S,16R)-7,11-dihydroxy-3-(2-(2-methyl-4-thiazolyl)ethenyl)-8,8,10,12,16-pentamethyl-4,17-dioxabicyclo[14.1.0]heptadecane-5,9-dione (B)

0.52 ml of EDTA and 0.87 ml of 1,1,1-trifluoroacetone, then a mixture that consists of 106.2 mg of oxone and 61 mg of sodium bicarbonate are added at 0° C. under nitrogen to 44 mg of the title compound, produced in Example 8, in 0.92 ml of acetonitrile. It is stirred for 2 hours at 0° C. It is mixed with 2 ml of sodium thiosulfate solution, stirred for 5 minutes and extracted three times with 10 ml of ethyl acetate each. The organic phase is washed once with saturated sodium chloride solution, dried on sodium sulfate and concentrated by evaporation in a vacuum. The thus obtained residue is purified by preparative thick-layer chromatography. With methylene chloride/ethyl acetate 30%, run twice, 5.5 mg of title compound A is obtained as a nonpolar component, and 27 mg of title compound B is obtained as a polar component as colorless oils.

$^1$H-NMR (CDCl$_3$) of A: δ=0.94 (3H), 1.05 (3H), 1.11 (3H), 1.1–1.60 (5H), 1.28 (3H), 1.35 (3H), 1.77 (2H), 1.89 (1H), 2.11 (1H), 2.41 (1H), 2.50 (1H), 2.74 (3H), 2.82 (1H), 3.08 (1H), 3.33 (1H), 3.79 (1H), 4.04 (1H), 4.14 (1H), 5.88 (1H), 6.58 (1H), 6.60 (1H), 6.96 (1H) ppm.

$^1$H-NMR (CDCl$_3$) of B: δ=1.00 (3H), 1.08 (3H), 1.1–1.60 (5H), 1.18 (3H), 1.29 (3H), 1.35 (3H), 1.64–1.75 (2H), 1.95 (1H), 2.07 (1H), 2.39 (1H), 2.42 (1H), 2.56 (1H), 2.73 (3H), 2.91 (1H), 3.35 (1H), 3.78 (1H), 3.85 (1H), 4.10 (1H), 5.70 (1H), 6.57 (1H), 6.67 (1H), 6.97 (1H) ppm.

EXAMPLE 11

(1R,3S(E),7S,10R,11S,12S,16R)-7,11-Dihydroxy-3-(2-(2-methyl-4-thiazolyl)ethenyl)-8,8,10,12,16-pentamethyl-4,17-dioxabicyclo(14.1.0]heptadecane-5,9-dione (A) and (1S,3S(E),7S,10R,11S,12S,16S)-7,11-dihydroxy-3-(2-(2-methyl-4-thiazolyl)ethenyl)-8,8,10,12,16-pentamethyl-4,17-dioxabicyclo[14.1.0]heptadecane-5,9-dione (B)

Analogously to Example 10, 2.7 mg of title compound A is obtained as a nonpolar component and 5.5 mg of title compound B is obtained as a polar component as colorless oils from 10 mg of the title compound that is produced in Example 9.

$^1$H-NMR (CDCl$_3$) of A: δ=0.94 (3H), 1.09 (3H), 1.0–2.1 (8H), 1.11 (3H), 1.31 (3H), 1.43 (3H), 2.26 (1H), 2.39 (1H), 2.51 (1H), 2.69 (3H), 3.00 (1H), 3.12 (1H), 3.21 (1H), 3.37 (1H), 3.66 (1H), 4.16 (1H), 5.63 (1H), 6.57 (1H), 6.58 (1H), 6.95 (1H) ppm.

$^1$H-NMR (CDCl$_3$) of B: δ=0.95 (3H), 1.04 (3H), 1.0–1.9 (5H), 1.14 (3H), 1.28 (3H), 1.44 (3H), 1.71 (1H), 1.93 (1H), 2.00 (1H), 2.10 (1H), 2.30 (1H), 2.44 (1H), 2.52 (1H), 2.71 (3H), 2.93 (1H), 3.29 (1H), 3.68 (1H), 3.74 (1H), 0.4.19 (1H), 5.69 (1H), 6.56 (1H), 6.63 (1H), 6.97 (1H) ppm.

EXAMPLE 12

(4S,7R,8S,9S,13Z,16S(E))-4,8-Dihydroxy-16-(1-methyl-2-(2-pyridyl)ethenyl)-1-oxa-7-propyl-5,5,9,13-tetramethyl cyclohexadec-13-ene-2,6-dione

EXAMPLE 12a (4S(4R,5S,6S,10E/Z,13S,14E))-4-(13-[[(1,1-Dimethylethyl)dimethyl-silyl]oxy]-4-propyl-15-(2-pyridyl)-3-oxo-5-hydroxy-2,6,10,14-tetramethyl-pentadeca-10,14-dien-2-yl)-2,2-dimethyl-[1,3]dioxane (A) and (4S(4S,5R,6S,10E/Z,13S,14E))-4-(13-[[(1,1-dimethylethyl)dimethylsilyl]oxy]-4-propyl-15-(2-pyridyl)-3-oxo-5-hydroxy-2,6,10,14-tetramethyl-pentadeca-10,14-dien-2-yl)-2,2-dimethyl-[1,3]dioxane (B)

Analogously to Example 1a, 1.2 g (4.95 mmol) of (4S)-4-(2-methyl-3-oxo-hept-2-yl)-2,2-dimethyl-[1,3]dioxane, which was produced according to the process described in DE 197 51 200.3, is reacted with 1.45 g (3.49 mmol) of (2S,6E/Z,9S,10E)-9-[[dimethyl(1,1-dimethylethyl)silyl]oxy]-11-(2-pyridyl)-2,6,10-trimethyl-undeca-6,10-dienal, which was produced according to the process described in DE 197 51 200.3, and after working-up and chromatographic separation, 1.14 g (1.73 mmol, 50%) of title compound A and 6.87 mg (1.04 mmol, 30%) of title compound B are isolated in each case as a colorless oil.

$^1$H-NMR (CDCl$_3$) of A: δ=0.01 (3H), 0.06 (3H), 0.82 (3H), 0.89 (12H), 0.99 (3H); 1.12–1.85 (11H), 1.24 (3H), 1.31 (3H), 1.37 (3H), 1.59+1.68 (3H), 1.89–2.10 (2H), 2.03 (3H), 2.28 (2H), 2.85 ((1H), 3.25 (1H), 3.43 (1H), 3.87 (1H), 3.98 (1H), 4.11 (1H), 4.18 (1H), 5.16 (1H), 6.47 (1H), 7.08 (1H), 7.22 (1H), 7.62 (1H), 8.59 (1H) ppm.

$^1$H-NMR (CDCl$_3$) of B: δ=0.02 (3H), 0.07 (3H), 0.81–1.02 (15H), 1.02–1.76 (11H), 1.07 (3H), 1.19 (3H), 1.29 (3H), 1.39 (3H), 1.61+1.69 (3H), 1.90–2.10 (2H), 2.05 (3H), 2.29 (2H), 2.83+3.02 (1H), 3.26 (1H), 3.48 (1H), 3.84 (1H), 3.96 (1H), 4.06–4.21 (2H), 5.19 (1H), 6.48 (1H), 7.08 (1H), 7.23 (1H), 7.62 (1H), 8.59 (1H) ppm.

EXAMPLE 12b (3S,6R,7S,8S,12E/Z,15S,16E)-15-[[(1,1-Dimethylethyl)dimethyl-silyl]oxy]-6-propyl-17-(2-pyridyl)-5-oxo-4,4,8,12,16-pentamethyl-heptadeca-12,16-diene-1,3,7-triol The solution of 1.79 g (2.72 mmol) of the compound, presented according to Example 12a, in 70 ml of anhydrous ethanol is mixed under an atmosphere of dry argon with 1.29 g of p-toluenesulfonic acid-monohydrate, and it is stirred for 2.5 hours at 23° C. It is mixed with a saturated sodium bicarbonate solution, diluted with water, extracted several times with dichloromethane, and the combined organic extracts are dried on sodium sulfate. The residue that is obtained after filtration and removal of the solvent is purified by chromatography on about 400 ml of fine silica gel with a mobile solvent mixture that consists of n-hexane and ethyl acetate. 1.6 g (2.20 mmol, 81%) of the title compound is isolated as a colorless oil.

$^1$H-NMR (CDCl$_3$): δ=0.02(3H), 0.08 (3H), 0.80–0.96 (15H), 1.01–2.35 (15H), 1.05+1.08 (3H), 1.23+1.27 (3H), 1.61+1.68 (3H), 1.99+2.01 (3H), 2.78–3.12 (2H), 3.27 (1H), 3.38+3.48 (1H), 3.85 (2H), 4.04–4.21 (3H), 5.11+5.23 (1H), 6.42 (1H), 7.10-(1H), 7.28 (1H), 7.63 (1H), 8.60 (1H) ppm.

EXAMPLE 12c (3S,6R,7S,8S,12E/Z,15S,16E)-6-Propyl-17-(2-pyridyl)-4,4,8,12,16-pentamethyl-1,3,7,15-tetrakis-[(dimethyl(1,1-dimethylethyl)silyl]oxy]-heptadeca-12,16-dien-5-one Analogously to Example 1b, 1.36 g (2.20 mmol) of the compound that is presented according to Example 12b is reacted, and after working-up and purification, 2.06 g (2.14 mmol, 97%) of the title compound is isolated as a colorless oil.

$^1$H-NMR. (CDCl$_{31}$: δ=–0.02–0.12 (24H), 0.80–0.96 (42H), 1.00–1.71 (11H), 1.04 (3H), 1.20 (3H), 1.60–1.68 (3H), 1.89–2.09 (2H), 2.05 (3H), 2.28 (2H), 3.03 (1H), 3.58 (1H), 3.69 (1H), 3.80 (1H), 3.92 (1H), 4.12 (1H), 5.18 (1H), 6.47 (1H), 7.07 (1H), 7.21 (1H), 7.62 (1H), 8.60 (1H) ppm.

EXAMPLE 12d (3S,6R,7S,8S,12E/Z,15S,16E)-1-Hydroxy-17-(2-pyridyl)-4,4,8,12,16-pentamethyl-6-propyl-3,7,15-tris-[[dimethyl(1,1-dimethylethyl)silyl]oxy]-heptadeca-12,16-dien-5-one Analogously to Example 1c, 2.05 g (21.13 mmol) of the compound that is presented according to Example 12c is reacted, and after working-up and purification, 1.69 g (2.00 mmol, 94%) of the title compound is isolated as a colorless oil.

$^1$H-NMR (CDCl$_3$): δ=0.00–0.16 (18H), 0.81–0.99 (33H), 1.09 (3H), 1.03–1.72 (15H), 1.19 (3H), 1.90–2.10 (2H), 2.06 (3H), 2.28 (2H), 3.03 (1H), 3.68 (2H), 3.81 (1H), 4.03–4.18 (2H), 5.19 (1H), 6.48 (1H), 7.08 (1H), 7.22 (1H), 7.61 (1H), 8.60 (1H) ppm.

EXAMPLE 12e (3S,6R,7S,8S,12E/Z,15S,16E)-6-Propyl-3,7,15-tris-[[dimethyl(1,1-dimethylethyl)silyl]oxy]-4,4,8,12,16-pentamethyl-17-(2-pyridyl) -5-oxo-heptadeca-12,16-dienal Analogously to Example 1d, 1.69 g (2.0 mmol) of the compound that is presented according to Example 12d is reacted, and after working-up, 1.76 g of the title compound is isolated as a crude product, which is further reacted without purification.

EXAMPLE 12f (3S,6R,7S,8S,12Z,15S,16E)-6-Propyl-3,7,15-tris-[[dimethyl(1,1-dimethylethyl)silyl]oxy]-4,4,8,12,16-pentamethyl-17-(2-pyridyl) -5-oxo-heptadeca-12,16-dienoic acid (A) and (3S,6R,7S,8S,12E,15S,16E)-6-propyl-3,7,15-tris-[(dimethyl(1,1-dimethylethyl) silyl]oxy]-4,4,8,12,16-pentamethyl-17-(2-pyridyl) 5-oxo-heptadeca-12,16-dienoic acid (B)

Analogously to Example 1e, 1.76 g (maximum 2.00 mmol) of the compound that is presented according to Example 12e is reacted, and after working-up and purification, 672 mg (0.78 mmol, 29%) of title compound A and 527 mg (0.61 mmol, 31%) of title compound B are isolated in each case as a colorless oil.

$^1$H-NMR (CDCl$_3$) of A: δ=–0.04–0.16 (18H), 0.78–0.96 (33H), 1.01–1.74 (10H), 1.11 (3H), 1.20 (3H), 1.70 (3H), 1.84 (1H), 1.92 (3H), 2.14–2.40 (4H), 2.55 (1H), 3.02 (1H), 3.78 (1H), 4.16 (1H), 4.40 (1H), 5.22 (1H), 6.63 (1H), 7.18 (1H), 7.33 (1H), 7.71 (1H), 8.62 (1H) ppm.

$^1$H-NMR (CDCl$_3$) of B: δ=–0.02–0.18 (18H), 0.78–0.96 (33H), 0.96–1.62 (10H), 1.12-(3H), 1.22 (3H), 1.57 (3H), 1.81–2.08 (2H), 1.94 (3H), 2.23–2.42 (3H), 2.64 (1H), 3.09 (1H), 3.83 (1H), 4.13 (1H), 4.35 (1H), 5.11 (1H), 6.49 (1H), 7.18 (1H), 7.37 (1H), 7.71 (1H), 8.62 (1H) ppm.

EXAMPLE 12g (3S,6R,7S,8S,12Z,15S,16E)-15-Hydroxy-6-propyl-3,7-bis -[[dimethyl(1,1-dimethylethyl)silyl]oxy]-4,4, 8,12,16-pentamethyl -17-(2-pyridyl)-S-oxo-heptadeca-12,16-dienoic acid Analogously to Example 1f, 672 mg (0.78 mmol) of compound A that is presented according to Example 12f is reacted, and after working-up, 642 mg (maximum 0.78 mmol) of the title compound is isolated as a crude product, which is further reacted without purification.

EXAMPLE 12h (4S,7R,8S,9S,13Z,16S(E))-4,8-Bis-([dimethyl(1,1-dimethylethyl)silyl]oxy]-7-propyl-16-(1-methyl-2-(2-pyridyl)ethenyl)-1-oxa-5,5,9,13-tetramethyl-cyclohexadec-13-ene -2,6-dione Analogously to Example 1g, 642 mg (maximum 0.78 mmol) of the compound that is presented according to Example 12g is reacted, and after working-up and purification, 427 mg (586 μmol, 75%) of the title compound is isolated as a colorless oil.

$^1$H-NMR (CDCl$_3$) δ=–0.08 (3H), 0.09–0.12 (9H), 0.79–1.82 (10H), 0.83 (3H), 0.86 (9H), 0.94 (9H), 0.99 (3H), 1.13 (3H), 1.19 (3H), 1.69 (3H), 2.08–2.21 (1H), 2.15 (3H), 2.44 (1H), 2.54–2.82 (3H), 3.03 (1H), 3.99 (1H), 4.06 (1H), 5.02 (1H), 5.18 (1H), 6.58 (1H), 7.10 (1H), 7.25 (1H), 7.63 (1H), 8.60 (1H) ppm.

EXAMPLE 12

(4S,7R,8S,9S,13Z,16S(E))-4,8-Dihydroxy-16-(1-methyl-2-(2-pyridy)ethenyl)-1-oxa-7-propyl-5,5,9,13-tetramethyl-cyclohexadec -13-ene-2,6-dione Analogously to Example 1, 425 mg (584 μmol) of the compound that is presented according to Example 12h is reacted, and after working-up and purification, 204 mg (408 μmol, 70%) of the title compound is isolated as a colorless oil.

$^1$H-NMR (CDCl$_3$): =0.89 (3H), 1.03 (3H), 1.07 (3H), 1.16–1.47 (4H), 1.36 (3H), 1.47–1.88 (6H), 1.72 (3H), 2.04 (3H), 2.21–2.39 (3H), 2.47 (1H), 2.64 (1H), 2.81 (1H), 3.28 (1H), 3.67 (1H), 4.37 (1H), 4.67 (1H), 5.11 (1H), 5.19 (1H), 6.61 (1H), 7.13 (1H), LT 7.29 (1H), 7.69 (1H), 8.52 (1H) ppm.

EXAMPLE 13

(1S,3S(E),7S,10R,11S,12S,16R)-10-Propyl-7,11-dihydroxy-3-(1-methyl-2-(2-N-oxidopyridyl)ethenyl)-8,8,12,16-tetramethyl-4,17-dioxabicyclo[14.1.0]heptadeca-5,9-dione (A) and (1R,3S(E),7S,10R,11S,12S,16S)-10-propyl-7,11-dihydroxy-3-(1-methyl-2-(2-N-oxidopyridyl)ethenyl)-8,8,12,16-tetramethyl-4,17-dioxabicyclo(14.1.0]heptadeca-5,9-dione (B)

Analogously to Example 2, 30 mg (60 μmol) of the compound that is presented according to Example 12 isreacted, and after working-up and purification, 23 mg (43 μmol, 72%) of title compound A and 5 mg (9.4 μmol, 16%) of title compound B are isolated in each case as a colorless oil.

$^1$H-NMR (CDCl$_3$) of A: δ=0.88 (3H), 0.99 (3H), 1.03 (3H), 1.08–2.03 (12H), 1.30 (3H), 1.41 (3H), 2.10 (3H), 2.23 (2H), 2.53 (1H), 2.73 (1H), 2.80 (1H), 3.38 (1H), 3.60 (1H), 4.52 (1H), 5.41 (1H), 6.15 (1H), 6.93 (1H), 7.21 (1H), 7.36 (1H), 7.42 (1H), 8.27 (1H) ppm.

$^1$H-NMR (CDCl$_3$) of B: δ=0.90 (3H), 0.94 (3H), 1.01–1.98 (12H), 1.08 (3H), 1.30 (3H), 1.45 (3H), —2.03 (1H), 2.12 (3H), 2.41–2.57 (2H), 2.84 (1H), 3.30 (1H), 3.37 (1H), 3.85 (1H), 4.51 (1H), 5.39 (1H), 5.53 (1H), 7.02 (1H), 7.19 (1H), 7.32 (1H), 7.44 (1H), 8.29 (1H) ppm.

EXAMPLE 14

(1S,3S(E),7S,10R,11S,12S,16R)-10-Propyl-7,11-dihydroxy-3-(1-methyl-2-(2-pyridyl)ethenyl)-8,8,12,16-tetramethyl-4,17-dioxabicyclo[14.1.0]heptadeca-5,9-dione Analogously to Example 3, 23 mg (43 μmol) of compound A that is presented according to Example 13 is reacted, and after working-up and purification, 11 mg (21 μmol, 93%) of the title compound is isolated as a colorless oil.

$^1$H-NMR (CDCl$_3$) δ=0.89 (3H), 0.98 (3H), 1.06 (3H), 1.13–2.03 (12H), 1.28 (3H), 1.39 (3H), 2.09 (3H), 2.14 (1H), 2.36 (1H), 2.53 (1H), 2.80 (1H), 2.96 (1H), 3.39 (1H), 3.61 (1H), 4.38 (1H), 5.28 (1H), 5.43 (1H), 6.60 (1H), 7.14 (1H), 7.29 (1H), 7.69 (1H), 8.53 (1H) ppm.

EXAMPLE 15

(1R,3S(E),7S,10R,11S,12S,16S)-10-Propyl-7,11-dihydroxy-3-(1-methyl-2-(2-pyridyl)ethenyl)-8,8,12,16-tetramethyl-4,17-dioxabicyclo[14.1.0]heptadecane-5,9-dione Analogously to Example 3, 5 mg (9.3 μmol) of compound B that is presented according to Example 13 is reacted, and after working-up and purification, 1.5 mg (2.9 μmol, 31%) of the title compound is isolated as a colorless oil.

$^1$H-NMR (CDCl$_3$) δ=0.89 (3H), 0.95 (3H), 1.01–1.92 (12H), 1.04 (3H), 1.29 (3H), 1.37 (3H), 2.09 (1H), 2.11 (3H), 2.48 (1H), 2.58 (1H), 2.98 (1H), 3.08 (1H), 3.29 (1H), 3.51 (1H), 3.92 (1H), 4.34 (1H), 5.58 (1H), 6.64 (1H), 7.12 (1H), 7.28 (1H), 7.66 (1H), 8.59 (1H) ppm.

EXAMPLE 16

(4S,7R,8S,9S,13E,16S(E))-4,8-Dihydroxy-16-(1-methyl-2-(2-pyridyl)ethenyl)-1-oxa-7-propyl-5,5,9,13-tetramethyl-cyclohexadec-13-ene-2,6-dione

EXAMPLE 16a (3S,6R,7S,8S,12E,15S,16E)-15-Hydroxy-6-propyl-3,7-bis -[[dimethyl(1,1-dimethylethyl)silyl]oxy]-4,4,8,12,16-pentamethyl -17-(2-pyridyl)-5-oxo-heptadeca-12,16-dienoic acid Analogously to Example 1f, 527 mg (0.61 mmol) of compound B that is presented according to Example 12f is reacted, and after working-up, 508 mg (maximum 0.61 mmol) of the title compound is isolated as crude product, which is further reacted without purification.

EXAMPLE 16b (4S,7R,8S,9S,13E,16S(E))-4,8-Bis-[[dimethyl(1,1-dimethylethyl)silyl]oxy]-7-propyl-16-(1-methyl-2-(2-pyridyl)ethenyl)-1-oxa-5,5,9,13-tetramethyl-cyclohexadec-13-ene -2,6-dione Analogously to Example 1 g, 508 mg (maximum 0.61 mmol) of the compound that is presented according to Example 16a is reacted, and after working-up and purification, 358 mg (492 μmol, 80%) of the title compound is isolated as a colorless oil.

$^1$H-NMR (CDCl$_3$): δ=0.02–0.16 (12H), 0.79–1.72 (33H), 1.11 (3H), 1.19 (3H), 1.59 (3H), 1.86 (1H), 2.07–2.20 (1H), 2.13 (3H), 2.38 (1H), 2.48–2.66 (3H), 2.97 (1H), 3.89 (1H), 4.39 (1H), 5.22 (1H), 5.29 (1H), 6.56 (1H), 7.08 (1H), 7.18 (1H), 7.61 (1H), 8.59 (1H) ppm.

EXAMPLE 16

(4S,7R,8S,9S,13E,16S(E))-4,8-Dihydroxy-16-(1-methyl-2-(2-pyridyl)ethenyl)-1-oxa-7-propyl-5,5,9,13-tetramethyl cyclohexadec-13-ene-2,6-dione Analogously to Example 1, 356 mg (489 μmol) of the compound that is presented according to Example 16b is reacted, and after working-up and purification, 201 mg (402 μmol, 82%) of the title compound is isolated as a colorless oil.

$^1$H-NMR (CDCl$_3$): δ=0.82–2.23 (12H), 0.87 (3H), 0.98 (3H), 1.01 (3H), 1.30 (3H), 1.62 (3H), 2.08 (3H), 2.37–2.67 (4H), 3.41 (1H), 3.68 (1H), 4.20 (2H), 5.08 (1H), 5.39 (1H), 6.58 (1H), 7.12 (1H), 7.34 (1H), 7.68 (1H), 8.53 (1H) ppm.

EXAMPLE 17

(1R,3S(E),7S,10R,11S,12S,16R)-10-Propyl-7,11-dihydroxy-3-(1-methyl-2-(2-N-oxidopyridyl)ethenyl)-8,8,12,16-tetramethyl-4,17-dioxabicyclo[14.1.0]heptadeca-5,9-dione (A) and (1S,3S(E),7S,10R,11S,12S,16S)-10-propyl-7,11-dihydroxy-3-(1-methyl-2-(2-N-oxidopyridyl)ethenyl)-8,8,12,16-tetramethyl-4,17-dioxabicyclo[14.1.0]heptadeca-5,9-dione (B)

Analogously to Example 2, 191 mg (382 μmol) of the compound that is presented according to Example 16 is reacted, and after working-up and purification, 188 mg (354 μmol, 93%) of a mixture of the two title compounds A and B are isolated as a colorless oil.

$^1$H-NMR (CDCl$_3$) of A and B: δ=0.82–0.94 (6H), 1.05 (3H), 1.12–1.29 (6H), 1.32–2.24 (10H), 1.38+1.42 (3H), 2.03+2.10 (3H), 2.31–2.62 (2H), 2.87–2.99 (1H), 3.31–3.77 (3H), 4.56 (1H), 5.11+5.57 (1H), 5.42+5.60 (1H), 6.98+7.03 (1H), 7.21 (1H), 7.33 (1H), 7.43 (1H), 8.24–8.32 (1H) ppm.

EXAMPLE 18

(1R,3S(E),7S,10R,11S,12S,16R)-10-Propyl-7,11-dihydroxy-3-(1-methyl-2-(2-pyridyl)ethenyl)-8,8,12,16-tetramethyl-4,17-dioxabicyclo[14.1.0]heptadeca-5,9-dione (A) and (1S,3S(E),7S,10R,11S,12S,16S)-10-propyl-7,11-dihydroxy-3-(1-methyl-2-(2-pyridyl)ethenyl)-8,8,12,16-tetramethyl-4,17-dioxabicyclo[14.1.0]heptadeca-5,9-dione (B)

Analogously to Example 3, 187 mg (352 μmol) of the compounds that are presented according to Example 17 is reacted, and after working-up and purification, 64 mg (124 μmol, 35%) of title compound A or B and 13 mg (25 μmol, 7%) of title compound B or A in each case are isolated as a colorless oil.

$^1$H-NMR (CDCl$_3$) of A or B: δ=0.88 (3H), 0.92 (3H), 1.03 (3H), 1.10–1.89 (11H), 1.29 (3H), 1.38 (3H), 2.06 (2H), 2.11 (3H), 2.52 (2H), 2.88 (1H), 3.11 (1H), 3.38 (1H), 3.74 (1H), 4.38 (2H), 5.50 (1H), 6.65 (1H), 7.12 (1H), 7.31 (1H), 7.68 (1H), 8.57 (1H) ppm.

$^1$H-NMR (CDCl$_3$) of B or A: δ=0.89 (3H), 0.90 (3H), 1.04–1.90 (11H), 1.08-(3H), 1.23 (3H), 1.37 (3H), 1.99–2.16 (2H), 2.09 (3H), 2.55 (2H), 2.94 (2H), 3.31 (1H), 3.67 (1H), 4.03 (1H), 4.31 (1H), 5.44 (1H), 6.62 (1H), 7.13 (1H), 7.28 (1H), 7.67 (1H), 8.55 (1H) ppm.

What is claimed is:

1. An epothilone compound of formula I,

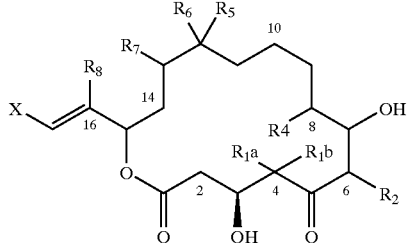

in which
R$^4$ means hydrogen, C$_1$–C$_{10}$ alkyl, aryl, C$_7$–C$_{20}$ aralkyl,
R$^5$ means hydrogen, C$_1$–C$_{10}$ alkyl, aryl, C$_7$–C$_{20}$ aralkyl,
wherein, for R$^4$ and R$^5$, aryl is phenyl, wherein said phenyl is optionally substituted in one or more places by halogen, OH, O-alkyl, CO$_2$H; CO$_2$-alkyl, —NH$_2$, —NO$_2$, —N$_3$, —CN, C$_1$–C$_{20}$ alkyl, C$_1$–C$_{20}$ acyl and/or C$_1$–C$_{20}$ acyloxy groups, and
wherein, for R$^4$ and R$^5$, aralkyl is benzyl or phenylethyl, wherein said benzyl or phenylethyl is optionally substituted in one or more places by halogen, OH, O-alkyl, CO$_2$H, CO$_2$-alkyl, —NO$_2$, —N$_3$, —CN, C$_1$–C$_{20}$ alkyl, C$_1$–C$_{20}$ acyl and/or C$_1$–C$_{20}$ acyloxy groups,
R$^6$, R$^7$ each mean a hydrogen atom, or together mean an additional bond to result in a double bond on the ring between their two positions or together mean an oxygen atom to provide an epoxide ring,
R$^8$ means a methyl group or hydrogen,
and at the same time, R$^{1a}$ and R$^{1b}$ together stand for a trimethylene group, R$^2$ stands for a phenyl or benzyl radical, and X stands for a 2-methyl-4-thiazolyl or 2-methyl-4-oxazolyl radical or
at the same time R$^{1a}$ and R$^{1b}$ together stand for a trimethylene group, R$^2$ stands for a methyl, ethyl or propyl group and X stands for a 2-methyl-4-thiazolyl or 2-methyl-4-oxazolyl radical or at the same time R$^{1a}$ and R$^{1b}$ in each case stand for a methyl group, R$^2$ stands for a methyl, ethyl or propyl radical, and X stands for a 2-methyl-4-thiazolyl or 2-methyl-4-oxazolyl radical,
wherein the nitrogen atom and/or the sulfur atom in X can be present in oxidized form, and
wherein, R$^2$ and R$^8$ each are simultaneously not a methyl radical, or a stereoisomer thereof.

2. A compound according to claim 1, in which R$^8$ is a hydrogen atom.

3. A compound according to claim 1, in which R$^8$ is a methyl group.

4. A compound according to claim 1, in which R$^2$ is an ethyl group.

5. A compound according to claim 1, in which R$^2$ is a propyl group.

6. A compound according to claim 2, in which R$^2$ is a propyl group.

7. A compound according to claim 1, in which R$^5$ is a methyl group.

8. A compound according to claim 1, in which X is 2-methyl-4-thiazolyl.

9. A compound according to claim 1, in which X is 2-methyl-4-oxazolyl radical.

10. A compound according to claim 1, in which R$^{1a}$ and R$^{1b}$ in each case stand for a methyl group.

11. A compound according to claim 1, in which R$^{1a}$ and R$^{1b}$ together stand for a trimethylene group.

12. A compound according to claim 1, in which R$^6$ and R$^7$ together mean an oxygen atom to provide an epoxide ring.

13. A compound according to claim 8, in which R$^6$ and R$^7$ together mean an oxygen atom to provide an epoxide ring.

14. A compound according to claim 9, in which R$^6$ and R$^7$ together mean an oxygen atom to provide an epoxide ring.

15. A compound according to claim 10, in which R$^6$ and R$^7$ together mean an oxygen atom to provide an epoxide ring.

16. A compound according to claim 11, in which R$^6$ and R$^7$ together mean an oxygen atom to provide an epoxide ring.

17. A compound of formula I of claim 1, which is:
(4S,7R,8S,9S,13(E or Z), 16S(E))-4,8-Dihydroxy-16-(2-(2-methyl-4-thiazolyl)ethenyl)-1-oxa-5,5,7,9,13-pentamethyl-cyclohexadec-13-ene-2,6-dione,
(1S or R),3S(E),7S,10R,11S,12S,16R)-7,11-Dihydroxy-3-(2-(2-methyl-4-thiazolyl)ethenyl)-8,8,10,12,16-pentamethyl-4,17-dioxabicyclo[14.1.0]heptadeca-5,9-dione,
(1R or S),3S(E),7S,10R,11S,12S,16S)-7,11-Dihydroxy-3-(2-(2-methyl-4-thiazolyl)ethenyl)-8,8,10,12,16-pentamethyl-4,17-dioxabicyclo[14.1.0]heptadeca-5,9-dione,
(4S,7R,8S,9S,13(E or Z), 16S(E))-4,8-Dihydroxy-7-ethyl-16-(2-(2-methyl-4-thiazolyl)ethenyl) 1-oxa-5,5,9,13-tetramethyl-cyclohexadec-13-ene-2,6-dione,
(1S or R),3S(E),7S,10R, 11S,12S,16R)-7,11-Dihydroxy-10-ethyl-3-(2-(2-methyl-4-thiazolyl)ethenyl)-8,8,12,16-tetramethyl-4,17-dioxabicyclo[14.1.0]heptadeca-5,9-dione,
(1R or S),3S(E),7S,10R,11S,12S,16S)-7,11-Dihydroxy-10-ethyl-3-(2-(2-methyl-4-thiazolyl)ethenyl)-8,8,12,16-tetramethyl-4,17-dioxabicyclo[14.1.0]heptadeca-5,9-dione,
(4S,7R,8S,9S,13(E or Z), 16S(E))-4,8-Dihydroxy-16-(2-(2-methyl-4-thiazolyl)ethenyl) 1-oxa-5,5-(1,3-trimethylene)-7,9,13-trimethyl-cyclohexadec-13-ene-2,6-dione, (1(S or R),3S(E),7S,10R,11S,12S,16R)-7,11-Dihydroxy-3-(2-(2-methyl-4-thiazolyl)ethenyl)-8,8-(1,3-trimethylene)-10,12,16-trimethyl-4,17-dioxabicyclo[14.1.0]heptadeca-5,9-dione, (1(R or S),3S(E),7S,10R,11S,12S,16S)-7,11-Dihydroxy-3-(2-(2-methyl-4-thiazolyl)ethenyl)-8,8-(1,3-trimethylene)-10,12,16-trimethyl-4,17-dioxabicyclo[14.1.0]heptadeca-5,9-dione, (4S,7R,8S,9S,13(E or Z), 16S(E))-4,8-Dihydroxy-7-ethyl-16-(2-(2-methyl-4-thiazolyl)ethenyl)-1-oxa-5,5-(1,3-trimethylene)-9,13-dimethyl-cyclohexadec-13-ene-2,6-dione, (1(S or R),3S(E),7S,10R,11S,12S,16R)-7,11-Dihydroxy-10-ethyl-3-(2-(2-methyl-4-thiazolyl)ethenyl)-8,8-(1,3-trimethylene)-12,16-dimethyl-4,17-dioxabicyclo[14.1.0]heptadeca-5,9-dione, or (1(R or S),3S(E),7S,10R,11S,12S,16S)-7,11-Dihydroxy-10-ethyl-3-(2-(2-methyl-4-thiazolyl)ethenyl)-8,8-(1,3-trimethylene)-12,16-dimethyl-4,17-dioxabicyclo[14.1.0]heptadeca-5,9-dione.

18. A pharmaceutical composition comprising a therapeutically effective amount of at least one compound of formula I according to claim 1 and a pharmaceutically compatible vehicle.

19. A pharmaceutical composition comprising a therapeutically effective amount of a compound of claim 17 and a pharmaceutically compatible vehicle.

20. A method for preparing a pharmaceutical composition comprising bringing together a pharmaceutically acceptable carrier and a compound of formula I according to claim 1.

* * * * *

UNITED STATES PATENT AND TRADEMARK OFFICE
CERTIFICATE OF CORRECTION

PATENT NO. : 7,001,916 B1  
APPLICATION NO. : 09/913163  
DATED : February 21, 2006  
INVENTOR(S) : Ulrich Klar et al.

Page 1 of 1

It is certified that error appears in the above-identified patent and that said Letters Patent is hereby corrected as shown below:

On the Title page, item [75] Inventors: line 1, reads "Belin" should read -- Berlin --  
Column 95, line 47, reads "$CO_2H$;" should read -- $CO_2H$, --  
Column 96, line 56, reads "ethenyl) 1-oxa" should read -- ethenyl)-1-oxa --  
Column 96, line 66, reads "ethenyl) 1-oxa" should read -- ethenyl)-1-oxa --

Signed and Sealed this

Twentieth Day of February, 2007

JON W. DUDAS  
*Director of the United States Patent and Trademark Office*